US012763164B2

(12) United States Patent
Fang et al.

(10) Patent No.: US 12,763,164 B2
(45) Date of Patent: Oct. 13, 2026

(54) METHODS FOR HIGH-RESOLUTION MICROBIOME ANALYSIS

(71) Applicant: ICAHN SCHOOL OF MEDICINE AT MOUNT SINAI, New York, NY (US)

(72) Inventors: Gang Fang, New York, NY (US); John Beaulaurier, New York, NY (US)

(73) Assignee: Icahn School of Medicine at Mount Sinai, Bronx, NY (US)

( * ) Notice: Subject to any disclaimer, the term of this patent is extended or adjusted under 35 U.S.C. 154(b) by 1190 days.

(21) Appl. No.: 16/626,671

(22) PCT Filed: Jun. 27, 2018

(86) PCT No.: PCT/US2018/039678

§ 371 (c)(1),
(2) Date: Dec. 26, 2019

(87) PCT Pub. No.: WO2019/005913

PCT Pub. Date: Jan. 3, 2019

(65) Prior Publication Data

US 2020/0160936 A1 May 21, 2020

Related U.S. Application Data

(60) Provisional application No. 62/525,908, filed on Jun. 28, 2017.

(51) Int. Cl.
*G16B 20/20* (2019.01)
*C12Q 1/6869* (2018.01)
(Continued)

(52) U.S. Cl.
CPC .......... *G16B 20/20* (2019.02); *C12Q 1/6869* (2013.01); *G16B 30/10* (2019.02); *G16B 30/20* (2019.02)

(58) Field of Classification Search
None
See application file for complete search history.

(56) References Cited

U.S. PATENT DOCUMENTS

2014/0179553 A1 6/2014 Parks et al.
2015/0242565 A1 8/2015 Li et al.
(Continued)

FOREIGN PATENT DOCUMENTS

CN 103088433 A 5/2013
WO 2018/071841 A1 4/2018
WO 2018195091 A1 10/2018

OTHER PUBLICATIONS

Marbouty M. Science Advances 3: e1602105, pp. 1-11. (Year: 2017).*

(Continued)

*Primary Examiner* — Olivia M. Wise
*Assistant Examiner* — Robert J. Kallal

(57) ABSTRACT

Methods are presented for binning metagenomic sequences that leverage long reads from a single-molecule long-read sequencing technology and utilize DNA methylation signatures inferred from these reads to resolve individual reads and assembled contigs into species- and strain-level clusters. Methods for deconvoluting prokaryotic organisms in a microbiome sample are presented. Methods for mapping mobile genetic elements to their host organisms in a microbiome sample are also presented.

15 Claims, 37 Drawing Sheets

Specification includes a Sequence Listing.

(51) Int. Cl.
*G16B 30/10* (2019.01)
*G16B 30/20* (2019.01)

(56) References Cited

U.S. PATENT DOCUMENTS

| | | | |
|---|---|---|---|
| 2016/0130646 | A1 | 5/2016 | Korlach et al. |
| 2016/0239602 | A1 | 8/2016 | Shendure et al. |

OTHER PUBLICATIONS

Rhoads A. PacBio Sequencing and its applications. Genomics Proteomics Bioinformatics 13: 278-289. (Year: 2015).*

Alneberg J. Binning metagenomic contigs by coverage and composition. Nature Methods 11(11): 1144-1146. (Year: 2014).*

Beaulaurier J. Single molecule-level detection and long read-based phasing of epigenetic variations in bacterial methylomes. Nature Communications 6(7438): pp. 12. (Year: 2015).*

Oliveira PH. The interplay of restriction-modification systems with mobile genetic elements and their prokaryotic hosts. Nucleic Acids Research 42(16): 10618-10631. (Year: 2014).*

Beaulaurier J. Single molecule-level detection and long read-based phasing of epigenetic variations in bacterial methylomes. Nature Communications 6(7438): pp. 31 (with supplementary information). (Year: 2015).*

Abdul Sater Mr. DNA Methylation Assessed by SMRT Sequencing Is Linked to Mutations in Neisseria meningitidis Isolates. Plos One 10(12): e0144612. (Year: 2015).*

Partial European Search Report issued in European Patent Application No. 18824159.0 dated Feb. 12, 2021.

Abdul Sater et al., "DNA Methylation Assessed by SMRT Sequencing Is Linked to Mutations in Neisseria meningitidis Isolates", PLOS ONE, vol. 10, No. 12, 2015, p. e0144612, 19 pages.

Beaulaurier et al., "Single molecule-level detection and long read-based phasing of epigenetic variations in bacterial methylomes", Nature Communications, vol. 6, Article No. 7438, 2015, pp. 1-12.

Droge et al., "Taxonomic binning of metagenome samples generated by next-generation sequencing technologies," Briefings in Bioinformatics, vol. 13, No. 6, 2012, pp. 646-655.

Mazumdar-Leighton et al., "Metagenomics at grass roots", Resonance—Journal of Science Education, Indian Academy of Sciences, vol. 22, No. 3, 2017, pp. 291-301.

Beaulaurier, et al., "Metagenomic Binning and Association of Plasmids with Bacterial Host Genomes using DNA Methylation", Nature Biotechnology, vol. 36, No. 1, pp. 1-28, Dec. 11, 2017.

International Search Report and Written Opinion mailed on Oct. 2, 2018, issued in corresponding PCT/Application No. PCT/US2018/039678.

Office Action issued in CN 201880055371.6 dated Mar. 31, 2023.

Abdul Sater, Mohamad R. et al., DNA Methylation Assesssed by SMRT Sequencing is linked to mutations in Meisseria meningitidis Isolates, PLOS ONE, vol. 10, No. 12, Dec. 11, 2015.

Beaulaurier, John et al., Single molecule-level detection and long read-based phasing of epigenetic variations in bacterial methylomes, Nature Communications, vol. 6, No. 1, Jun. 15, 2015.

Droge, J. et al., Taxonomic binning of metagenome samples generated by next-generation sequencing technologies, Briefing in Bioinformatics, vol. 13, No. 6, Jul. 31, 2012.

Sudeshna, Mazumdar-Leighton et al., Metagenomics at grass roots, RESONANCE—Journal of Science Eduction, Indian Academy of Sciences, India, vol. 22, No. 3, May 27, 2017.

Oliveira, Pedro H. et al., The interplay of restriction-modification systems with mobile genetic elements and their prokaryotic hosts, Nucleic Acids Research, vol. 42, No. 16, Aug. 12, 2014.

Extended European Search Report for European application No. 25151718.1 dated Jun. 3, 2025.

* cited by examiner

| Percent | Phylum / Class / Order / Family |
|---|---|
| 59.55% | Bacteroidetes / Bacteroidia / Bacteroidales / S24-7 |
| 13.38% | Verrucomicrobia / Verrucomicrobiae / Verrucomicrobiales / Verrucomicrobiaceae |
| 5.21% | Firmicutes / Erysipelotrichi / Erysipelotrichales / Erysipelotrichaceae |
| 4.52% | Firmicutes / Clostridia / Clostridiales / Lachnospiraceae |
| 3.96% | Firmicutes / Bacilli / Lactobacillales / Lactobacillaceae |
| 2.75% | Actinobacteria / Coriobacteriia / Coriobacteriales / Coriobacteriaceae |
| 2.42% | Firmicutes / Clostridia / Clostridiales / Ruminococcaceae |
| 2.12% | Bacteroidetes / Bacteroidia / Bacteroidales / Rikenellaceae |
| 2.07% | Proteobacteria / Betaproteobacteria / Burkholderiales / Alcaligenaceae |
| 1.36% | Firmicutes / Clostridia / Clostridiales / Unknown |
| 0.63% | Firmicutes / Clostridia / Clostridiales / Clostridiaceae |
| 0.52% | Proteobacteria / Deltaproteobacteria / Desulfovibrionales / Desulfovibrionaceae |
| 0.44% | Cyanobacteria / 4C0d-2 / YS2 / Unknown |
| 0.25% | Tenericutes / Mollicutes / RF39 / Unknown |
| 0.20% | Firmicutes / Clostridia / Clostridiales / Other |
| 0.16% | Proteobacteria / Alphaproteobacteria / RF32 / Unknown |
| 0.11% | Firmicutes / Clostridia / Clostridiales / Christensenellaceae |
| 0.07% | Firmicutes / Clostridia / Clostridiales / Peptococcaceae |
| 0.06% | Other / Other / Other / Other |
| 0.21% | All Other Categories |

Figure 2D

| bin | Bacillales | Bacteroidales | Burkholderiales | Clostridiales | Cytophagales | Eggerthellales | Enterobacterales | Erysipelotrichales | Flavobacteriales | Lactobacillales | Rhizobiales | Unlabeled | Verrucomicrobiales |
|---|---|---|---|---|---|---|---|---|---|---|---|---|---|
| 0 | 0.00 | 0.00 | 0.00 | 0.06 | 0.00 | 0.00 | 0.00 | 0.01 | 0.00 | 0.00 | 0.00 | 0.15 | 0.00 |
| 1 | 0.00 | 0.00 | 0.00 | 0.00 | 0.00 | 0.00 | 0.00 | 0.00 | 0.00 | 0.00 | 0.00 | 0.00 | 0.00 |
| 2 | 0.02 | 0.76 | 0.32 | 0.00 | 0.03 | 0.00 | 0.01 | 0.54 | 0.02 | 1.69 | 0.02 | 0.28 | 0.00 |
| 3 | 0.01 | 0.16 | 1.98 | 0.01 | 0.01 | 0.00 | 0.00 | 0.00 | 0.00 | 0.05 | 0.00 | 0.65 | 0.00 |
| 4 | 0.00 | 0.00 | 0.00 | 0.00 | 0.00 | 0.00 | 0.00 | 0.00 | 0.00 | 1.83 | 0.00 | 0.00 | 0.00 |
| 5 | 0.00 | 0.39 | 0.00 | 0.00 | 0.00 | 0.00 | 0.01 | 0.00 | 0.00 | 0.00 | 0.00 | 0.04 | 0.01 |
| 6 | 0.01 | 0.00 | 0.00 | 0.00 | 0.00 | 0.11 | 0.00 | 0.00 | 0.00 | 0.00 | 0.00 | 0.02 | 0.00 |
| 7 | 0.00 | 0.00 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.00 | 0.00 | 0.00 | 0.00 | 0.00 | 0.00 | 0.00 |
| 9 | 0.00 | 0.00 | 0.00 | 0.00 | 0.00 | 0.00 | 0.00 | 0.00 | 0.00 | 0.00 | 0.00 | 0.00 | 0.00 |
| 10 | 0.00 | 1.26 | 0.01 | 0.01 | 0.06 | 0.03 | 0.01 | 0.00 | 0.02 | 0.00 | 0.05 | 0.48 | 0.00 |
| 11 | 0.00 | 0.64 | 0.00 | 0.00 | 0.02 | 0.00 | 0.01 | 0.00 | 0.00 | 0.00 | 0.00 | 0.05 | 0.00 |
| 12 | 0.00 | 0.00 | 0.00 | 0.00 | 0.00 | 0.00 | 0.00 | 0.00 | 0.00 | 0.00 | 0.00 | 0.00 | 0.00 |
| 13 | 0.00 | 27.71 | 0.03 | 0.00 | 0.00 | 0.00 | 0.00 | 0.00 | 0.00 | 0.00 | 0.00 | 0.20 | 0.00 |
| 14 | 0.00 | 0.00 | 0.00 | 0.00 | 0.00 | 0.00 | 0.00 | 0.00 | 0.00 | 0.00 | 0.00 | 0.00 | 0.00 |
| 15 | 0.00 | 0.00 | 0.00 | 0.00 | 0.00 | 0.00 | 0.00 | 0.00 | 0.00 | 0.01 | 0.00 | 0.00 | 0.00 |
| 16 | 0.00 | 0.35 | 0.10 | 0.00 | 0.00 | 0.00 | 0.01 | 0.00 | 0.00 | 0.00 | 0.02 | 0.39 | 0.00 |
| 17 | 0.00 | 0.01 | 0.00 | 0.02 | 0.00 | 0.00 | 0.01 | 0.01 | 0.00 | 0.00 | 0.00 | 0.11 | 0.00 |
| 18 | 0.00 | 0.03 | 0.00 | 0.00 | 0.00 | 0.00 | 0.00 | 0.00 | 0.00 | 0.00 | 0.00 | 0.02 | 0.00 |
| 19 | 0.05 | 0.01 | 0.00 | 0.26 | 0.00 | 0.00 | 0.00 | 0.00 | 0.01 | 0.07 | 0.00 | 0.29 | 0.00 |
| 20 | 0.00 | 0.00 | 0.00 | 2.02 | 0.00 | 0.00 | 0.00 | 0.00 | 0.00 | 0.00 | 0.00 | 0.09 | 0.00 |
| 21 | 0.04 | 0.00 | 0.00 | 0.14 | 0.00 | 0.00 | 0.00 | 0.01 | 0.00 | 0.01 | 0.00 | 0.14 | 0.00 |
| 22 | 0.00 | 0.00 | 0.01 | 0.03 | 0.00 | 0.00 | 0.00 | 0.00 | 0.00 | 0.01 | 0.00 | 0.22 | 0.00 |
| 23 | 0.00 | 0.00 | 0.00 | 0.78 | 0.00 | 0.00 | 0.00 | 0.03 | 0.00 | 0.09 | 0.00 | 0.09 | 0.00 |
| 24 | 0.00 | 0.00 | 0.00 | 0.00 | 0.00 | 0.00 | 0.00 | 0.00 | 0.00 | 0.00 | 0.00 | 0.00 | 0.00 |
| 25 | 0.01 | 2.72 | 0.04 | 0.00 | 0.02 | 0.00 | 0.01 | 0.00 | 0.02 | 0.00 | 0.02 | 0.54 | 0.00 |
| 26 | 0.02 | 0.01 | 0.00 | 0.02 | 0.00 | 0.00 | 0.00 | 0.00 | 0.00 | 1.15 | 0.00 | 0.18 | 0.00 |
| 27 | 0.00 | 0.45 | 0.03 | 0.00 | 0.00 | 0.00 | 0.00 | 0.00 | 0.00 | 0.00 | 0.00 | 0.12 | 2.73 |
| 28 | 0.00 | 0.00 | 0.00 | 0.00 | 0.00 | 0.00 | 0.00 | 0.00 | 0.00 | 0.23 | 0.00 | 0.00 | 0.00 |

Figure 10

METHODS FOR HIGH-RESOLUTION MICROBIOME ANALYSIS

CROSS REFERENCE TO RELATED APPLICATIONS

This patent application is a U.S. National Phase of International Patent Application No. PCT/US2018/039678, filed Jun. 27, 2018, which claims priority pursuant to 35 U.S.C. § 119(e) to U.S. Provisional Patent Application No. 62/525,908, filed Jun. 28, 2017, which is hereby incorporated by reference in its entirety.

STATEMENT REGARDING FEDERALLY SPONSORED RESEARCH

This invention was made with government support GM114472 awarded by the National Institute of Health. The government has certain rights to this invention.

REFERENCE TO A SEQUENCE LISTING

The instant application contains a Sequence Listing, which has been submitted electronically in ASCII format and is hereby incorporated by reference in its entirety. Said ASCII copy, created on Dec. 17, 2025, is named SeqList-084284-00332.txt and is 23,109 bytes in size.

FIELD OF THE INVENTION

The present subject matter relates, in general, to the field of genomics and metagenomics and, in particular, to metagenomic binning using DNA methylation and single-molecule long reads.

BACKGROUND

There is growing appreciation for the profound ways in which the human microbiome can impact our health, but the comprehensive characterization of these microbial populations remains difficult. Amplicon sequencing of the 16S rRNA gene provides a culture-free means of identifying many of the taxa present in a metagenomic sample, but the phylogenetic resolution of this technique is limited and the microbial genomic architecture outside of this single gene is left unexamined or only inferred indirectly. Whole metagenome shotgun sequencing provides access to all the genomic features of the constituent organisms, including bacterial and archaeal chromosomes, plasmids, transposons, and even bacteriophages with a phylogenetic resolution extending up to the strain level. However, multiple technical challenges hinder the interpretation of metagenomic sequencing data collected by short read next-generation sequencing (NGS) methods.

NGS data typically consists of millions of reads that are <200 bp in length, providing considerable depth of sequencing but limited ability to resolve both complex repeats and similar sequences that exist in multiple genomes. This presents significant challenges for de novo metagenomic assembly and interpretation of the resulting thousands of small assembled sequences (called contigs), which relies heavily on either reference-based annotation methods or segregation into putative taxa through a process known as metagenomic binning. Unsupervised (reference-free) methods have the potential to identify novel species, unlike supervised binning methods that require existing references to train classification algorithms. Several reference-free methods attempt to bin metagenomic reads prior to de novo assembly by using k-mer frequency metrics to assess sequence composition profiles or by tracking k-mer covariance across multiple samples. These methods do not depend on the results of a de novo assembly, but the binning resolution is limited by the information content found in short reads from standard NGS technologies.

Owing to the limited information content in short reads, most reference-free binning methods instead utilize the longer sequences of assembled contigs. Composition-based contig binning approaches not only rely on a successful de novo assembly, but also often fail to segregate sequences when the sample contains multiple high-similarity bacterial genomes. Differential coverage (or coverage covariance) methods, which partition sequences based on their similar abundance profiles across multiple samples, provide a powerful means of binning sequences in projects studying a large number of complex samples. However, they sometimes fail to untangle genomes of organisms that share similar abundances across samples and cannot effectively bin independently replicating mobile genetic elements (MGE), such as plasmids, transposons, bacteriophages, and Group I and II introns, which can have dramatically different abundance levels from their host chromosome(s). An alternative approach involves using Hi-C chromosomal interaction maps to link assembled contigs, including MGEs, but these methods are also limited by difficulties in distinguishing between closely related organisms due to high sequence similarity and uneven Hi-C link densities.

The information content of DNA is not limited to the primary nucleotide sequence (A, C, G and T), but is also conveyed by chemical modifications of individual nucleotides, including DNA methylation. In the bacterial (and archaeal) kingdom, DNA methylation is catalyzed by DNA methyltransferases (MTases) that apply methyl groups to DNA bases in a highly sequence-specific manner, causing certain sequence motifs to be nearly 100% methylated while the other motifs remain non-methylated. Single-molecule, real-time (SMRT) sequencing of native (amplification-free) DNA makes it possible to detect methylated bases and motifs in prokaryotic genomes. A recent survey of 230 diverse bacterial and archaeal genomes found DNA methylation in 93% of genomes across a wide diversity of methylated motifs (834 distinct motifs; averaging three motifs per organism). Importantly, the genetic contents of a cell (chromosomes and extrachromosomal DNA elements) all share the same set of methylation motifs, yet these motifs often differ dramatically across species and strains. The primary reason for such widespread diversity of methylated motifs is horizontal gene transfer (HGT) by mobile genetic elements. Since MTases are often shuttled by HGT, the process plays a crucial role in reconfiguring the bacterial methylomes. Additionally, mutation events can occur in the target recognition domain of MTase genes and thereby modify the sequence motif targeted for methylation, providing a route to further diversification of bacterial methylomes.

This raises the possibility of using SMRT sequencing to access DNA methylation in these communities, which essentially provides an orthogonal data dimension (endogenous epigenetic barcode) that can be leveraged for genome segregation in support of complementary features like coverage and sequence composition.

Whole metagenome shotgun sequencing is a comprehensive approach for characterizing complex microbial communities. However, significant challenges arise in the analysis of metagenomic sequences, often stemming from the presence of highly similar bacterial strains with varying relative abundances. Although a number of metagenomic binning methods have been developed that use features capturing sequence composition, organism abundance, and chromosome organization, many applications still suffer from insufficient discriminative power to distinguish among closely related species and strains with high sequence similarity. Single-molecule long-read sequencing technologies enabled the comprehensive detection of DNA methylation events in bacteria, a rich dimension of discriminative features beyond DNA sequences that have not yet been exploited in metagenomic analyses.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

A novel approach is presented for binning metagenomic sequences that leverages long reads from a single-molecule long-read sequencing technology and, for the first time, utilizes the DNA methylation signatures inferred from these reads to resolve individual reads and assembled contigs into species- and even strain-level clusters. This novel methylation-based binning approach also enables the mapping of mobile genetic elements (e.g., plasmids, transposons, including retrotransposons, DNA transposons, and insertion sequences, bacteriophages, group I introns, and group II introns) to their host species directly in a microbiome sample.

A novel approach is described to identify the DNA methylation patterns present in metagenomic data using read-level polymerase kinetics of SMRT reads and demonstrate how to exploit this data to derive a sequence-independent, endogenous epigenetic barcode that improves the resolution of metagenomic binning. Because the methylated motifs often differ even between closely-related species and strains, the methylation patterns (sets of motifs) present in SMRT reads and their assembled contigs offer a means for better differentiating sequences from taxonomical groups with high sequence similarity.

In one embodiment, an approach for organizing assembled contigs into taxon-specific clusters using DNA methylation profiles is described, and its complementarity with existing binning approaches that rely on sequence composition and coverage-covariance features is demonstrated.

In another embodiment, this approach is extended to discover the mappings between MGEs (e.g. plasmids) and their host organisms in a microbiome sample.

To complement contig-level DNA methylation-based binning, an approach has been developed and applied to leverage the long read lengths of SMRT sequencing to directly bin individual single-molecule reads using sequence composition and DNA methylation profiles, facilitating the detection of low-abundance organisms and resolving multi-strain de novo assemblies into isolated single-strain assemblies.

In one aspect of the invention, a method of deconvoluting genomes of prokaryotic organisms in a microbiome sample is provided, said method comprising the steps of:

a) obtaining a microbiome sample comprising a plurality of prokaryotic organisms;
b) sequencing nucleic acids of the prokaryotic organisms using single-molecule long reads sequencing technology, wherein the sequencing comprises the step of identifying methylated nucleotides, and at least one of the steps of:
   i. sequencing single molecule reads of nucleic acids;
   ii. assembling contigs from single molecule reads of the nucleic acids; and
c) assigning a methylation score reflecting the extent of methylation for sequence motifs of the nucleic acids on the assembled contig and/or the single molecule read;
d) applying motif filtering to identify sequence motifs with methylation scores indicating methylation on the assembled contigs and/or the single molecule reads;
e) determining nucleic acid methylation profiles of the assembled contigs or the single molecule reads in the microbiome sample based on motifs identified in step (d);
f) separating the assembled contigs and/or the single molecule reads into bins corresponding to distinct prokaryotic organisms based on the methylation profiles of step (e);
g) assembling the bins of step (f), thereby obtaining assembled genomes of the distinct bacterial organisms in the microbiome sample, thereby deconvoluting genomes of the prokaryotic organisms in a microbiome sample.

In some embodiments, two or more of the prokaryotic organisms in the microbiome sample have high sequence similarity. In some embodiments, two or more of the prokaryotic organisms in the microbiome sample have an average nucleotide identity of greater than about 75%, than about 80%, than about 85%, than about 90%, than about 95%, than about 97%, than about 98%, or than about 99%.

In another aspect, a method of mapping a mobile genetic element to a prokaryotic host organism in a microbiome sample comprising a plurality of prokaryotic organisms is provided, said method comprising the steps of:

a) obtaining a microbiome sample comprising a plurality of prokaryotic organisms;
b) sequencing nucleic acids of the prokaryotic organisms using single-molecule long reads sequencing technology, wherein the sequencing comprises the step of identifying methylated nucleotides and at least one of the steps of
   i. sequencing single molecule reads of nucleic acids; and
   ii. assembling contigs from single molecule reads of the nucleic acids;
c) assigning a methylation score reflecting the extent of methylation for sequence motifs of the nucleic acids on the assembled contig and/or the single molecule read;
d) applying motif filtering to identify motifs with methylation scores indicating methylation on the assembled contigs and/or the single molecule reads;
e) determining nucleic acid methylation profiles of the assembled contigs or the single molecule reads of at least one prokaryotic host organism and at least one mobile genetic element in the microbiome sample based on motifs identified in step (d);
f) comparing the nucleic acid methylation profiles of the at least one prokaryotic host organism in the microbiome sample and the at least one mobile genetic element in the microbiome sample and determining whether a match exists between said methylation profiles, and g) repeating steps (e) and (f) until a match between the mobile genetic element and the prokaryotic host organism is identified;

thereby mapping the mobile genetic element to the prokaryotic host organism.

In some embodiments of the above method, the nucleic acid methylation profile is a DNA methylation profile.

In one embodiment, the mobile genetic element is a plasmid, or a transposon, or a bacteriophage, or an intron.

Mobile genetic elements of any size can be mapped using the methods of the present invention. In some embodiments, the mobile genetic element is greater than about 1 kbp in length, or greater than about 2 kbp, or greater than about 5 kbp, or greater than about 10 kbp, or greater than about 20 kbp, or greater than about 30 kbp. In one non-limiting embodiment, the mobile genetic element is greater than 10 kbp in length.

In some embodiments the mobile genetic element confers certain properties to the host organism. By way of example, in one embodiment the mobile genetic element confers antibiotic resistance to the prokaryotic host organism. In another embodiment the mobile genetic element encodes a virulence factor in the prokaryotic host organism. In yet another embodiment the mobile genetic element provides a metabolic function to the prokaryotic host organism.

Microbiome samples of any size or complexity are within the scope to be analyzed by the methods of the present invention. In one embodiment, the microbiome sample analyzed by the methods of the present invention comprises greater than 3, or greater than 5, or greater than 10, or greater than 20, or greater than 50, or greater than 75, or greater than 100, or greater than 200, or greater than 300, or greater than 400, or greater than 500, or greater than 700, or greater than 1000, or greater than 2000, or greater than 5000, or greater than 10,000 prokaryotic host organisms.

In one embodiment the methylated nucleotides are selected from $N^6$-methyladenine, $N^4$-methylcytosine, and 5-methylcytosine and combinations thereof.

Any prokaryotic organisms known to those skilled in the art are within the scope of the present invention. In one non-limiting embodiment, the prokaryotic organisms are bacterial organisms, archaeal organisms, and combinations thereof. In some non-limiting embodiments, the prokaryotic organisms are bacterial organisms, bacterial species, or strains of bacterial species. In other non-limiting embodiments, the prokaryotic organisms are archaeal organisms, archaeal species, or strains of archaeal species.

In some non-limiting embodiments, the bacterial organisms comprise organisms of bacterial orders Bacteroidales, Bacillales, Bifidobacteriales, Burkholderiales, Clostridiales, Cytophagales, Eggerthallales, Enterobacterales, Erysipelotrichales, Flavobacteriales, Lactobacillales, Rhizobiales, or Verrucomicrobiales, and combinations thereof.

In some non-limiting embodiments, the bacterial organisms are strains of *Bacteroides dorei, Bacteroides fragilis, Bacteroides thetaiotaomicron, Bifidobacterium breve, Bifidobacterium longum, Alistipes finegoldii*, or *Alistipes shahii.*

Microbiome samples analyzed by the methods of the invention can be obtained from any source known to those skilled in the art. In one non-limiting embodiment, the microbiome sample is obtained from soil, air, water (including, without limitation, marine water, fresh water, and rain water), sediment, oil, and combinations thereof. In another non-limiting embodiment, the microbiome sample is obtained from a subject selected from a protozoa, an animal (e.g., a mammal, e.g., human), or a plant. The subject (e.g., a mammal, e.g., a human) can be of any age (e.g., infant, child, adolescent, adult, or elderly.

In some embodiments, the subject is at a genetic risk for development a disease, e.g. diabetes mellitus, e.g., type I diabetes mellitus. In other embodiments, the subject may be at a risk of having, or have a bacterial infection, e.g., pneumonia infection.

Any single-molecule sequencing technology can be used in the methods of the present invention. In some embodiments, sequencing nucleic acids of the prokaryotic organisms is accomplished using a single-molecule real time (SMRT) technology or nanopore (e.g., Oxford Nanopore) sequencing technology.

In some embodiments of the above method, the nucleic acid methylation profile is a DNA methylation profile.

In some embodiments, the method described above comprises further steps. In one embodiment, the method described above further comprises the step of combining the methylation profiles of step (e) with other sequence features of the nucleic acids of the prokaryotic organisms in the microbiome sample prior to separating the assembled contigs and/or the single molecule reads into bins.

In one embodiment, the method described above comprises other sequence features, such as k-mer frequency profiles and coverage profiles across multiple samples.

In another embodiment, the method described above further comprises the step of combining contig binning assignments from other tools, such as cross-coverage and composition-based binning tools, with methylation scores in each bin, resulting in detection of methylated motifs in each bin and assignment of bin-level methylation scores in the microbiome sample.

In another embodiment, the method described above further comprises the step of aligning the single molecule reads to the contigs assembled from single molecule reads of the nucleic acids of step b) prior to the step of assigning a methylation score.

BRIEF DESCRIPTION OF THE DRAWINGS

FIGS. 2A-2F depict metagenomic binning by methylation profiles. FIG. 2A shows a receiver operating characteristic (ROC) curve illustrating the power to classify a contig as methylated or non-methylated regarding a specific sequence motif, as a function of the number IPD values available for the motif sites on the contig (see Examples). FIG. 2B shows a heatmap of contig-level methylation scores for fourteen motifs on a set of contigs from a metagenomic assembly of eight bacterial species. Contigs from each species possess distinct methylation profiles across the selected motifs. FIG. 2B discloses SEQ ID NOS 59-64, respectively, in order of appearance. FIG. 2C shows contig-level methylation scores for fourteen selected motifs are subject to t-SNE dimensionality reduction and plotted to show highly species-specific clusters of assembled contigs. FIG. 2D shows family-level annotation of 16S reads from an adult mouse gut microbiome by QIIME85. FIG. 2E shows a t-SNE projection of metagenomic contigs assembled from SMRT reads of an adult mouse gut microbiome, organized according to differing methylation profiles across 38 sequence motifs in the sample. Labeled bins denote genome-scale assemblies with distinct methylation profiles (see Table 5). FIG. 2F shows coverage values for contigs (>100 kp to exclude small MGEs) in each of the nine bins identified by methylation binning.

FIG. 3A is a histogram of sequence-based Euclidian distance between 5-mer frequency vectors of plasmid and chromosome sequences, showing the distance between plasmids and their host chromosome (based on 2,278 bacterial plasmids and their known hosts), as well as the distance between plasmid and randomly sampled chromosomes from other species ( ). FIG. 3B shows a heatmap showing methylation profiles for the pHel3 plasmid and its three hosts: *E. coli* CFT073, *E. coli* DH5α, and *H. pylori* JP26. The methylation profile of pHel3 across twenty motifs matches the host from which it was isolated. FIG. 3B discloses SEQ ID NOS 35-36, respectively, in order of appearance. FIG. 3C shows a simulation analysis using 878 SMRT sequenced bacterial genomes in the REBASE database showing expected number of genomes with a unique 6 mA methylome as a function of community size and presence of multi-strain species in the community. FIG. 3D shows a simulation analysis using 155 SMRT sequenced genomes with known plasmids in the REBASE database showing expected number of genomes with a unique 6 mA methylome as a function of community size and presence of multi-strain species in the community. FIG. 3E shows a simulation analysis using 878 SMRT sequenced genomes in the REBASE database showing the expected sequence lengths required to capture at least one instance of the methylation motifs in a genome. As expected, capturing at least one instance of some, but not all, of the methylation motifs reduces the required sequence length.

FIG. 4A shows 5-mer frequency-based binning of assembled contigs and raw reads (length >15 kb) from the HMP mock community, where only the unaligned reads are labeled. Reads from the low-abundance species *R. sphaeroides* form a distinct cluster near the coordinates (−8,−22). FIG. 4B shows the 2D histogram of contigs and unaligned reads, corresponding to FIG. 4A; this 2D histogram includes many highly species-specific subpopulations. FIG. 4C shows combined assembly of a synthetic mixture of reads from *H. pylori* strains J99 and 26995 results in one small contig containing mostly reads from strain 26695 and one large, highly chimeric contig. FIG. 4D shows read-level methylation profiles for unaligned reads from the synthetic mixture, separated by principal component analysis (PCA) into discrete, strain-specific clusters. FIG. 4E shows separate assembly of reads that were segregated using methylation profiles resulting in large, highly strain-specific contigs. FIG. 4F shows combined assembly of a synthetic mixture of reads from *E. coli* strains BAA-2196 O26:H11, BAA-2215 O103:H11, and BAA-2440 O111 resulting in many chimeric contigs that contain reads from all three strains. FIG. 4G shows reads from the synthetic mixture, aligned to the *E. coli* K12 MG1655 reference in order to correct raw SMRT sequence errors and the read-level methylation profiles separated by PCA into strain-specific clusters. FIG. 4H shows separate assembly of reads segregated by methylation profiles as demonstrated in FIG. 4G resulting in a dramatic reduction of chimerism in the assembled reads.

FIG. 5A shows Human Microbiome Project Mock Community B members in decreasing order of GC content in genome. The percentage of the reference positions covered by synthetic long reads (SLRs) is consistently lower than the percentage covered by abundance-matched SMRT reads. FIG. 5B shows uneven coverage by synthetic long reads in a 40 kbp region of the *S. agalactiae* genome; FIG. 5C shows uneven coverage by synthetic long reads in a 40 kbp region of the *S. aureus* genome, and FIG. 5D shows uneven coverage by synthetic long reads in a 50 kbp region of the *P. aeruginosa* genome.

FIG. 10 depicts taxonomic composition of the 29 bins identified by CONCOCT in the mouse gut metagenomic assembly. Taxonomy is based on contig-level annotations by Kraken.

FIG. 23 discloses SEQ ID NOS 37-41, 8, 42-44, 1 and 45-47, respectively, in order of appearance.

FIG. 24 discloses SEQ ID NOS 48-53, 1 and 54-58, respectively, in order of appearance.

DETAILED DESCRIPTION

Figure 1:
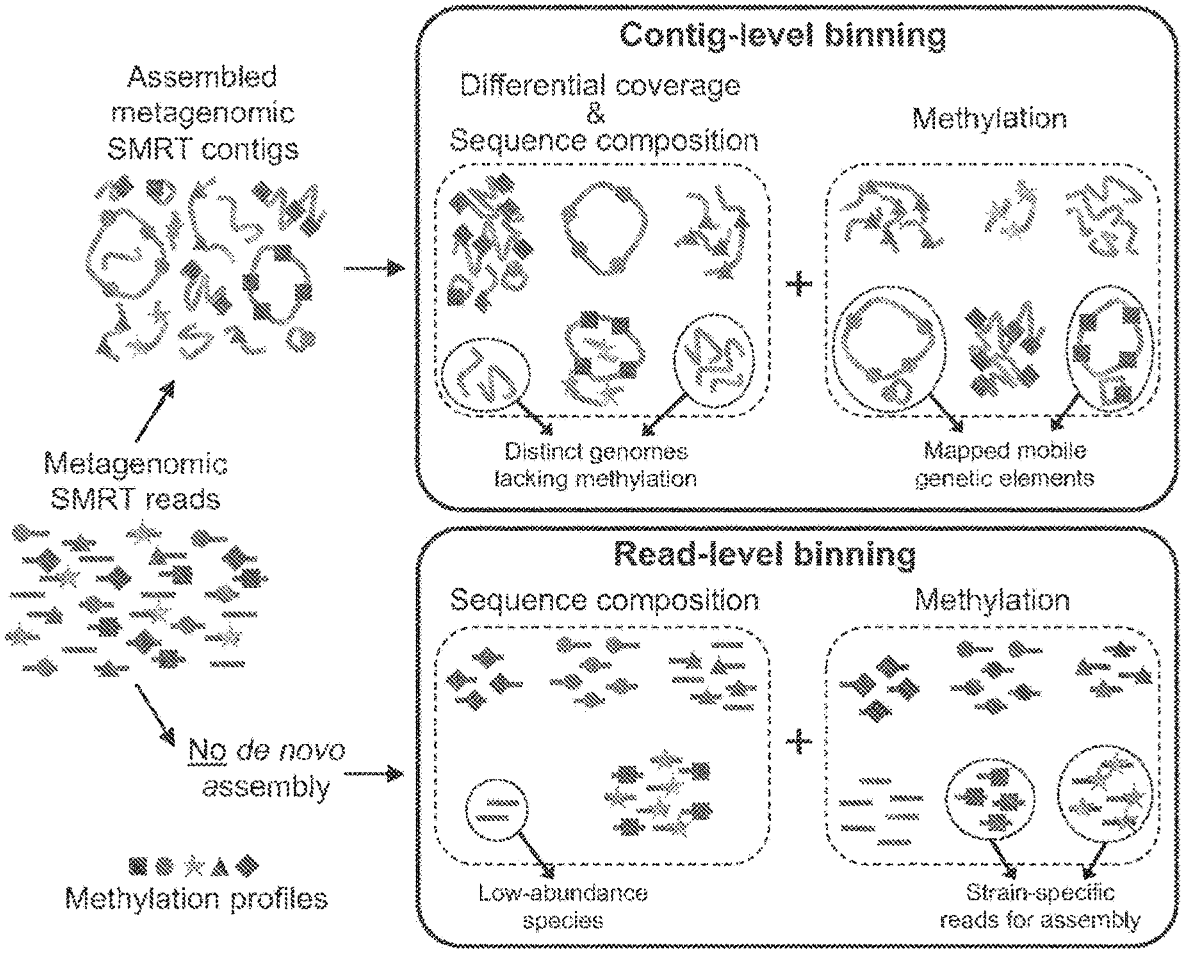
FIG. 1 depicts an overview of the metagenomic binning approaches based on DNA methylation and single molecule long reads. Given a set of metagenomic shotgun SMRT sequencing reads, one can either assemble them into contigs for contig-level binning or can directly perform read-level binning without de novo assembly. A widely used approach for unsupervised binning of metagenomic contigs uses coverage (and its covariance across multiple samples) and sequence composition profiles, but these can be complemented by methylation profiles to better segregate contigs with similar sequence composition and coverage covariance, as well as to map mobile genetic elements to contigs from their host bacterium in the microbiome sample. Read-level binning by sequence composition can isolate reads from low abundance species that do not assemble into contigs, while read binning by methylation profiles can segregate reads from multiple strains for the purpose of separate, strain-specific de novo genome assemblies. These four different binning methods can also be combined to take advantage of the strengths of each.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Definitions

Unless defined otherwise, all technical and scientific terms used herein have the same meaning as commonly understood by one of ordinary skill in the art to which this invention belongs.

As used in this specification and the appended claims, the singular forms “a”, “an”, and “the” include plural references unless the context clearly dictates otherwise. Thus, for example, a reference to “a method” includes one or more methods, and/or steps of the type described herein and/or which will become apparent to those persons skilled in the art upon reading this disclosure.

The terms “treat” or “treatment” of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

In one aspect of the invention, a methodology is provided that enables DNA methylation signatures in unamplified prokaryotic genomes to be profiled by SMRT sequencing and serve as endogenous epigenetic barcodes that present a rich, yet unexplored, dimension of discriminative features capable of providing high resolution metagenomic analyses.

In another aspect of the invention, methylation profiles are exploited as a general discriminative feature to segregate assembled contigs, and this methodology is superior to existing methods based on sequence composition profiles and coverage covariance.

In yet another aspect, methylation profiles are used to map MGEs (e.g., plasmids) to their bacterial host species in a microbiome sample, an advance that makes it possible to identify extra-chromosomal genes that can dramatically affect the pathogenicity and antibiotic susceptibility of their host bacterium directly via metagenomic sequencing.

Furthermore, in yet another embodiment, it is disclosed how the proposed single molecule read-level binning of long SMRT reads can be used to address multiple challenges in metagenomic de novo assembly, such as assisting in the identification of low-abundance organisms and simplifying de novo metagenome assembly of multiple co-existing strains with high sequence similarity.

Sequence binning by DNA methylation profiles enables multiple other applications. First, methylation profiling can be a tool to track the transmission of plasmids and bacteriophages across geographical locations, time points or conditions, such as antibiotic treatment. Because the methylation signature of a plasmid or phage reflects the most recent bacterial host in which it replicated, transmission events can be detected by comparing the methylation profile of a specific plasmid or phage (and the bacterial community) between two conditions. Second, aside from serving as endogenous epigenetic barcodes for metagenomic binning, bacterial DNA methylation events also plays an important role in the regulation of gene expression and pathogenicity. While existing methods require a clonal sample for methylation analysis, the proposed approach opens up the study of DNA methylations dynamics and epigenetic regulation to the vast research space of uncultured bacteria. Finally, de novo detection of methylation motifs in a metagenomic community also holds promise for the discovery of novel MTases and restriction enzymes, expanding the repertoire of enzymes available for use in biomedical research.

This study focuses on one of the three forms of DNA methylations 6 mA ($N^6$-methyladenine) because it is the most abundant DNA methylation in prokaryotes and it has strong signal-to-noise ratio in SMRT polymerase kinetics. Other less prevalent types of DNA methylation in bacteria, such as $N^4$-methylcytosine (4mC, medium-to-high signal) and 5-methylcytosine (5mC, low-to-medium signal) are also within the scope of the present invention. As single-molecule long-read sequencing technologies continue to mature, generating larger yields and longer reads, the longer read lengths will provide more robust composition and methylation signatures that can be leveraged to more effectively segregate metagenomic reads, while also leading to even longer contigs with higher quality.

Though the present embodiments focus on SMRT sequencing, the binning framework of the invention applies generally to other third-generation technology, for example Oxford Nanopore. By integrating the features of second- and third-generation sequencing with complementary approaches, like Hi-C intrachromosomal maps, contig coverage covariance or single cell techniques, practitioners in the microbiome and metagenomics arts will gain a much more complete understanding of both the genomic and epigenomic landscape of complex microbial communities.

In one aspect of the invention, a method of deconvoluting genomes of prokaryotic organisms in a microbiome sample is provided, said method comprising the steps of:

a) obtaining a microbiome sample comprising a plurality of prokaryotic organisms;
b) sequencing nucleic acids of the prokaryotic organisms using single-molecule long reads sequencing technology, wherein the sequencing comprises the step of identifying methylated nucleotides, and at least one of the steps of:
    i. sequencing single molecule reads of nucleic acids;
    ii. assembling contigs from single molecule reads of the nucleic acids; and
c) assigning a methylation score reflecting the extent of methylation for sequence motifs of the nucleic acids on the assembled contig and/or the single molecule read;
d) applying motif filtering to identify sequence motifs with methylation scores indicating methylation on the assembled contigs and/or the single molecule reads;
e) determining nucleic acid methylation profiles of the assembled contigs or the single molecule reads in the microbiome sample based on motifs identified in step (d);
f) separating the assembled contigs and/or the single molecule reads into bins corresponding to distinct prokaryotic organisms based on the methylation profiles of step (e);
g) assembling the bins of step (f), thereby obtaining assembled genomes of the distinct bacterial organisms in the microbiome sample, thereby deconvoluting genomes of the prokaryotic organisms in a microbiome sample.

In some embodiments of the above method, the nucleic acid methylation profile is a DNA methylation profile.

In some embodiments, the prokaryotic organisms in the microbiome sample do not have high sequence similarity. In some embodiments, two or more of the prokaryotic organisms in the microbiome sample have high sequence similarity. In some embodiments, two or more of the prokaryotic organisms in the microbiome sample have an average nucleotide identity of greater than about 75%, than about 80%, than about 85%, than about 90%, than about 95%, than about 97%, than about 98%, or than about 99%.

In another aspect, a method of mapping a mobile genetic element to a prokaryotic host organism in a microbiome sample comprising a plurality of prokaryotic organisms is provided, said method comprising the steps of:

a) obtaining a microbiome sample comprising a plurality of prokaryotic organisms;
b) sequencing nucleic acids of the prokaryotic organisms using single-molecule long reads sequencing technology, wherein the sequencing comprises the step of identifying methylated nucleotides and at least one of the steps of
    i. sequencing single molecule reads of nucleic acids; and
    ii assembling contigs from single molecule reads of the nucleic acids;
c) assigning a methylation score reflecting the extent of methylation for sequence motifs of the nucleic acids on the assembled contig and/or the single molecule read;
d) applying motif filtering to identify motifs with methylation scores indicating methylation on the assembled contigs and/or the single molecule reads;
e) determining nucleic acid methylation profiles of the assembled contigs or the single molecule reads of at least one prokaryotic host organism and at least one mobile genetic element in the microbiome sample based on motifs identified in step (d);
f) comparing the nucleic acid methylation profiles of the at least one prokaryotic host organism in the microbiome sample and the at least one mobile genetic element in the microbiome sample and determining whether a match exists between said methylation profiles, and
g) repeating steps (e) and (f) until a match between the mobile genetic element and the prokaryotic host organism is identified;

thereby mapping the mobile genetic element to the prokaryotic host organism.

In some embodiments of the above method, the nucleic acid methylation profile is a DNA methylation profile.

In one embodiment, the mobile genetic element is a plasmid, or a transposon, or a bacteriophage, or an intron.

Mobile genetic elements of any size can be mapped using the methods of the present invention. In some embodiments, the mobile genetic element is greater than about 1 kbp in length, or greater than about 2 kbp, or greater than about 5 kbp, or greater than about 10 kbp, or greater than about 20 kbp, or greater than about 30 kbp. In one non-limiting embodiment, the mobile genetic element is greater than 10 kbp in length.

In some embodiments the mobile genetic element confers certain properties to the host organism. By way of example, in one embodiment the mobile genetic element confers antibiotic resistance to the prokaryotic host organism. In another embodiment the mobile genetic element encodes a virulence factor in the prokaryotic host organism. In yet another embodiment the mobile genetic element provides a metabolic function to the prokaryotic host organism, e.g. an ability to survive under conditions that would otherwise be hostile, such as in an extreme environment.

Microbiome samples of any size or complexity are within the scope to be analyzed by the methods of the present invention. In one embodiment, the microbiome sample analyzed by the methods of the present invention comprises greater than 3, or greater than 5, or greater than 10, or greater than 20, or greater than 50, or greater than 75, or greater than 100, or greater than 200, or greater than 300, or greater than 400, or greater than 500, or greater than 700, or greater than 1000, or greater than 2000, or greater than 5000, or greater than 10,000 prokaryotic host organisms.

Any methylated nucleotides are within the scope of the methods of the present invention. In one embodiment the methylated nucleotides are selected from, without limitation, $N^6$-methyladenine, $N^4$-methylcytosine, and 5-methylcytosine and combinations thereof.

Any single-molecule sequencing technology can be used in the methods of the present invention. In some embodiments, sequencing nucleic acids of the prokaryotic organisms is accomplished using a single-molecule real time (SMRT) technology or nanopore (e.g., Oxford Nanopore) sequencing technology.

In some embodiments of the above method, the nucleic acid methylation profile is a DNA methylation profile.

In some embodiments, the method described above comprises further steps. In one embodiment, the method described above further comprises the step of combining the methylation profiles of step (e) with other sequence features of the nucleic acids of the prokaryotic organisms in the microbiome sample prior to separating the assembled contigs and/or the single molecule reads into bins.

In one embodiment, the method described above comprises other sequence features, such as k-mer frequency profiles and coverage profiles across multiple samples.

In another embodiment, the method described above further comprises the step of combining contig binning assignments from other tools, such as cross-coverage and composition-based binning tools, with methylation scores in each bin, resulting in detection of methylated motifs in each bin and assignment of bin-level methylation scores in the microbiome sample.

In another embodiment, the method described above further comprises the step of aligning the single molecule reads to the contigs assembled from single molecule reads of the nucleic acids of step b) prior to the step of assigning a methylation score.

Microbiome samples for use with the methods provided herein can be of any type that includes a microbial community comprising prokaryotic organisms. Prokaryotic organisms include, without limitation, bacterial organisms and archaeal organisms. The sample can include microorganisms from one or more domains. For example, in one embodiment, the sample comprises a heterogeneous population of bacteria and/or archaea.

Any prokaryotic organisms known to those skilled in the art are within the scope of the present invention. In one non-limiting embodiment, the prokaryotic organisms are bacterial organisms, archaeal organisms, and combinations thereof. In some non-limiting embodiments, the prokaryotic organisms are bacterial organisms, bacterial species, or strains of bacterial species. In other non-limiting embodiments, the prokaryotic organisms are archaeal organisms, archaeal species, or strains of archaeal species.

In some non-limiting embodiments, the bacterial organisms comprise organisms of bacterial orders Bacteroidales, Bacillales, Bifidobacteriales, Burkholderiales, Clostridiales, Cytophagales, Eggerthallales, Enterobacterales, Erysipelotrichales, Flavobacteriales, Lactobacillales, Rhizobiales, or Verrucomicrobiales, and combinations thereof.

In some non-limiting embodiments, the bacterial organisms are strains of *Bacteroides dorei, Bacteroides fragilis, Bacteroides thetaiotaomicron, Bifidobacterium breve, Bifidobacterium longum, Alistipes finegoldii*, or *Alistipes shahii.*

In one implementation, microbiome samples for use with the methods provided herein encompass, without limitation, samples obtained from the environment, including soil (e.g., rhizosphere), air, water (e.g., marine water, fresh water, rain water, wastewater sludge), sediment, oil, an extreme environmental sample (e.g., acid mine drainage, hydrothermal systems) and combinations thereof. In the case of marine or freshwater samples, the sample can be from the surface of the body of water, or any depth of the body of water, e.g., a deep sea sample. In one embodiment, the water sample is an ocean, a sea, a river, or a lake sample.

In one embodiment, the sample is a soil sample (e.g., bulk soil or rhizosphere sample). It has been estimated that 1 gram of soil contains tens of thousands of bacterial taxa, and up to 1 billion bacteria cells as well as about 200 million fungal hyphae (Wagg et al. (2010). Proc Natl. Acad. Sci. USA 111, pp. 5266-5270). Bacteria, archaea, actinomycetes, fungi, algae, protozoa and viruses are all found in soil. Soil microorganism community diversity has been implicated in the structure and fertility of the soil microenvironment, nutrient acquisition by plants, plant diversity and growth, as well as the cycling of resources between above- and below-ground communities. Accordingly, assessing the microbial contents of a soil sample over time provides insight into microorganisms associated with an environmental metadata parameter such as nutrient acquisition and/or plant diversity.

The soil sample in one embodiment is a rhizosphere sample, i.e., the narrow region of soil that is directly influenced by root secretions and associated soil microorganisms. As plants secrete many compounds into the rhizosphere, analysis of the organism types in the rhizosphere may be useful in determining features of the plants which grow therein.

In another embodiment, the sample is a marine or fresh water sample. Ocean water contains up to one million microorganisms per milliliter and several thousand microbial types. These numbers may be an order of magnitude higher in coastal waters with their higher productivity and higher load of organic matter and nutrients. Marine microorganisms are crucial for the functioning of marine ecosystems; maintaining the balance between produced and fixed carbon dioxide; production of more than 50% of the oxygen on Earth through marine phototrophic microorganisms such as Cyanobacteria, diatoms and pico- and nanophytoplankton; providing novel bioactive compounds and metabolic pathways; ensuring a sustainable supply of seafood products by occupying the critical bottom trophic level in marine foodwebs. Organisms found in the marine environment include viruses, bacteria, archaea and some eukarya. Marine bacteria are important as a food source for other small microorganisms as well as being producers of organic matter. Archaea found throughout the water column in the ocean are pelagic Archaea and their abundance rivals that of marine bacteria.

In another embodiment, the sample comprises a sample from an extreme environment, i.e., an environment that harbors conditions that are detrimental to most life on Earth. Organisms that thrive in extreme environments are called extremophiles. Though the domain Archaea contains well-known examples of extremophiles, the domain bacteria can also have representatives of these microorganisms. Extremophiles include: acidophiles which grow at pH levels of 3 or below; alkaliphiles which grow at pH levels of 9 or above; anaerobes such as Spinoloricus Cinzia which does not require oxygen for growth; cryptoendoliths which live in microscopic spaces within rocks, fissures, aquifers and faults filled with groundwater in the deep subsurface; halophiles which grow in about at least 0.2M concentration of salt; hyperthermophiles which thrive at high temperatures (about 80-122° C.) such as found in hydrothermal systems; hypoliths which live underneath rocks in cold deserts; lithoautotrophs such as *Nitrosomonas europaea* which derive energy from reduced mineral compounds like pyrites and are active in geochemical cycling; metallotolerant organisms which tolerate high levels of dissolved heavy metals such as copper, cadmium, arsenic and zinc; oligotrophs which grow in nutritionally limited environments; osmophiles which grow in environments with a high sugar concentration; piezophiles (or barophiles) which thrive at high pressures such as found deep in the ocean or underground; psychrophiles/cryophiles which survive, grow and/or reproduce at temperatures of about −15° C. or lower; radioresistant organisms which are resistant to high levels of ionizing radiation; thermophiles which thrive at temperatures between 45-122° C.; xerophiles which can grow in extremely dry conditions. Polyextremophiles are organisms that qualify as extremophiles under more than one category and include thermoacidophiles (prefer temperatures of 70-80° C. and pH between 2 and 3). The Crenarchaeota group of Archaea includes the thermoacidophiles.

In another implementation, microbiome samples for use with the methods provided herein encompass, without limitation, samples obtained from a subject, e.g., an animal subject, a protozoa subject, or a plant subject. The subject can be, for example, a human, mammal, primate, bovine, porcine, canine, feline, rodent (e.g., mouse or rat), or bird. In one embodiment, the animal subject is a mammal, e.g. a human. In one embodiment, the human subject is an adult, a child, an adolescent, an adult, or an elderly person.

In some embodiments, the subject is at a genetic risk for development a disease, e.g. diabetes mellitus, e.g., type I diabetes mellitus. In other embodiments, the subject may be at a risk of having, or have a bacterial infection, e.g., pneumonia infection.

In one embodiment the sample obtained from an animal subject is a body fluid. In another embodiment, the sample obtained from an animal subject is a tissue sample. Non-limiting samples obtained from an animal subject include tooth, perspiration, fingernail, skin, hair, feces, urine, semen, mucus, saliva, and gastrointestinal tract samples. The human microbiome comprises the collection of microorganisms found on the surface and deep layers of skin, in mammary glands, saliva, oral mucosa, conjunctiva and gastrointestinal tract. The microorganisms found in the microbiome include bacteria, fungi, protozoa, viruses and archaea. Different parts of the body exhibit varying diversity of microorganisms. The quantity and type of microorganisms may signal a healthy or diseased state for an individual. The number of bacteria taxa are in the thousands, and viruses may be as abundant. The bacterial composition for a given site on a body varies from person to person, not only in type, but also in abundance or quantity.

In the methods provided herein the one or more prokaryotic organisms can be of any type. For example, the one or more prokaryotic organisms can be from the domain Bacteria, Archaea, a combination thereof. Bacteria and Archaea are prokaryotic, having a very simple cell structure with no internal organelles. Bacteria can be classified into gram positive/no outer membrane, gram negative/outer membrane present and ungrouped phyla. Archaea constitute a domain or kingdom of single-celled microorganisms. Although visually similar to bacteria, archaea possess genes and several metabolic pathways that are more closely related to those of eukaryotes, notably the enzymes involved in transcription and translation. Other aspects of archaeal biochemistry are unique, such as the presence of ether lipids in their cell membranes. The Archaea are divided into four recognized phyla: Thaumarchaeota, Aigarchaeota, Crenarchaeota and Korarchaeota.

Binning Assembled Contigs Using Methylation Profiles

DNA methylation profiles inferred from SMRT sequencing provide an informative orthogonal epigenomic feature that can improve contig clustering. The DNA methylation profile is analogous to the sequence composition profile and the differential coverage profile, where normalized k-mer frequencies across k-mers and normalized coverage values across samples provide features for discriminative binning, respectively.

In the case of contig methylation profiles, each contig has a feature set consisting of contig-level DNA methylation scores across sequence motifs (see Examples).

Figure 2A:
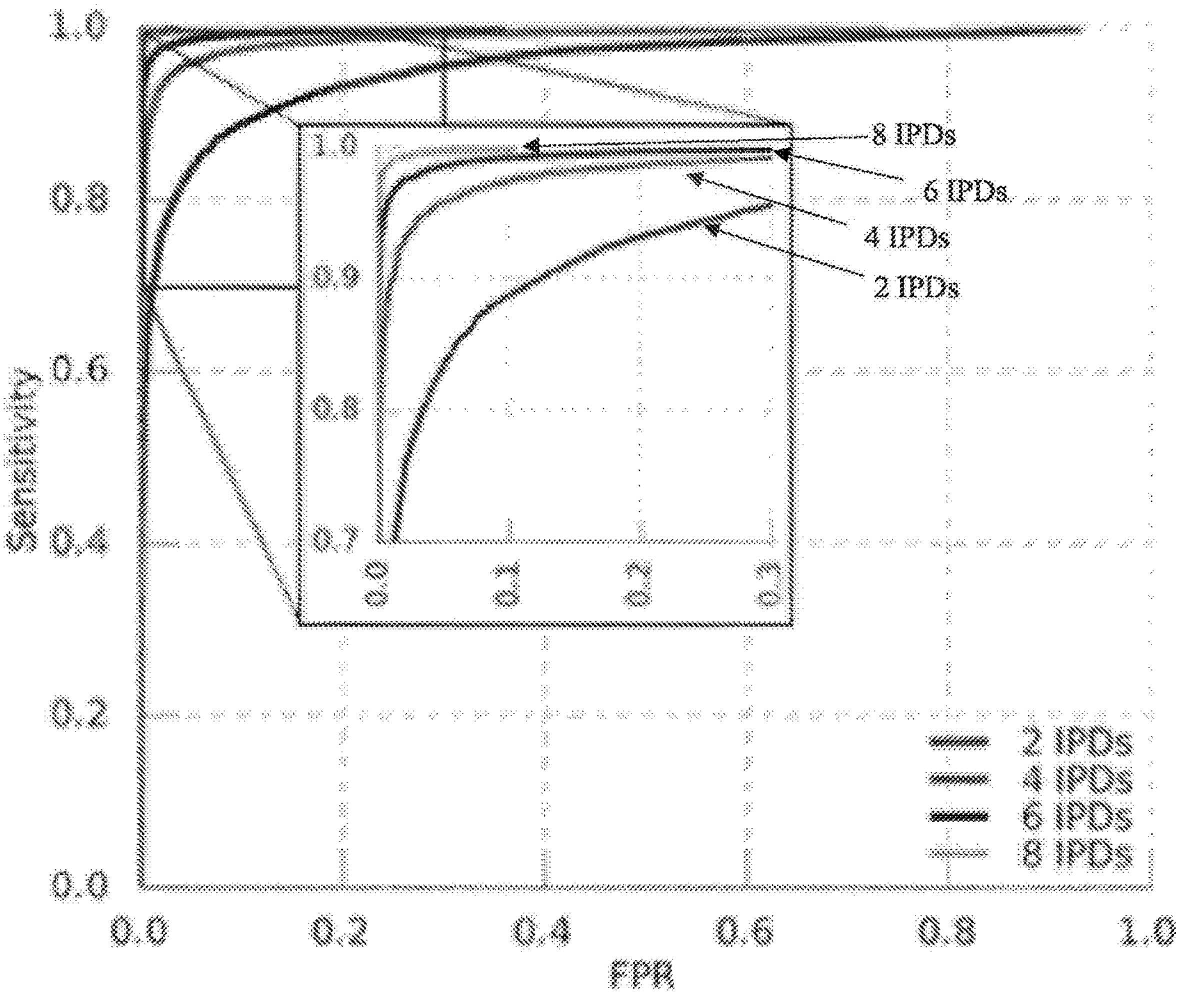

The methylation score for a given motif on a contig reflects the extent to which all instances of that motif on the contig are methylated. It is calculated using inter-pulse duration (IPD) values, which records the time it takes a DNA polymerase to translocate from one nucleotide to the next during real-time DNA synthesis, often referred to as the polymerase kinetics. The methylation score for a motif on a contig becomes more reliable for predicting DNA methylation with an increase in two values: (1) the number of motif sites on the contig, which is generally larger for shorter motifs, and (2) the number of reads aligning to the contig, as each read contributes independent IPD measurements of methylation likelihood at the motif site. Evaluation based on methylation data from a bacterium with a set of well-characterized $N^6$-methyladenine (6 mA) motifs suggests that the specificity and sensitivity of methylation scores for detecting methylated motifs improve dramatically with an increase in the number of individual IPD values used to calculate them (FIG. 2A; see Examples).

A critical first step in using methylation profiles for binning is to identify the methylated motifs in the metagenomic assembly, as only those motifs that are methylated on one or more contig will contribute to the discriminative power of the binning. Therefore, a motif filtering method was designed to identify the relatively small number of motifs with scores suggesting likely methylation, excluding from the downstream analysis the vast majority of motifs that lack evidence of methylation on any contigs in the assembly (see Examples). In the Examples presented below, motif filtering simplifies the motif feature space from over 204,000 to between 7-38 motifs in metagenomic assemblies.

The precise number of motifs that remain after filtering is often not critically important as long as the set of remaining motifs jointly captures the most significant differences between contig methylation profiles. This property contrasts with existing methods for methylation motif discovery that attempt to rigorously identify the single most parsimonious version of a motif. The proposed motif filtering is more robust to noise and different threshold choices, making it more effective and flexible for leveraging SMRT sequencing polymerase kinetics in a metagenomic setting.

To evaluate the ability of this procedure to segregate contigs based solely on DNA methylation profiles, a synthetic metagenomic mixture was created consisting of SMRT sequencing reads from eight separately sequenced bacterial species (Table 1, below), four of which belong to the genus *Bacteroides* (see Examples).

TABLE 1

SMRT sequencing details of the eight bacterial species from which the synthetic mixture was generated

| Species | NCBI reference sequence | # SMRT cells | # sequenced bases | # reads | Avg. read length (bp) | Genome coverage |
|---|---|---|---|---|---|---|
| *Bacteroides caccae* | GCA_000169015 | 1 | 1029981117 | 161221 | 6389 | 225 |
| *Bacteroides ovatus* | NZ_CP012938 | 1 | 819300070 | 98153 | 8347 | 122 |
| *Bacteroides thetaiotaomicron* | NC_004663 | 1 | 731132994 | 92674 | 7889 | 113 |
| *Bacteroides vulgatus* | NC_009614.1 | 1 | 680423977 | 90645 | 7506 | 125 |
| *Collinsella aerofaciens* | GCA_000169035 | 1 | 826741878 | 98462 | 8397 | 288 |
| *Clostridium bolteae* | GCA_000154365 | 1 | 591186370 | 95268 | 6206 | 89 |
| *Escherichia coli* | NC_000913 | 1 | 1018941198 | 96631 | 10545 | 219 |
| *Ruminococcus gnavus* | GCA_000169475 | 1 | 532400509 | 92738 | 5741 | 149 |
| Total | N/A | 8 | 6230108113 | 825792 | 7544 | N/A |

Figure 2B:
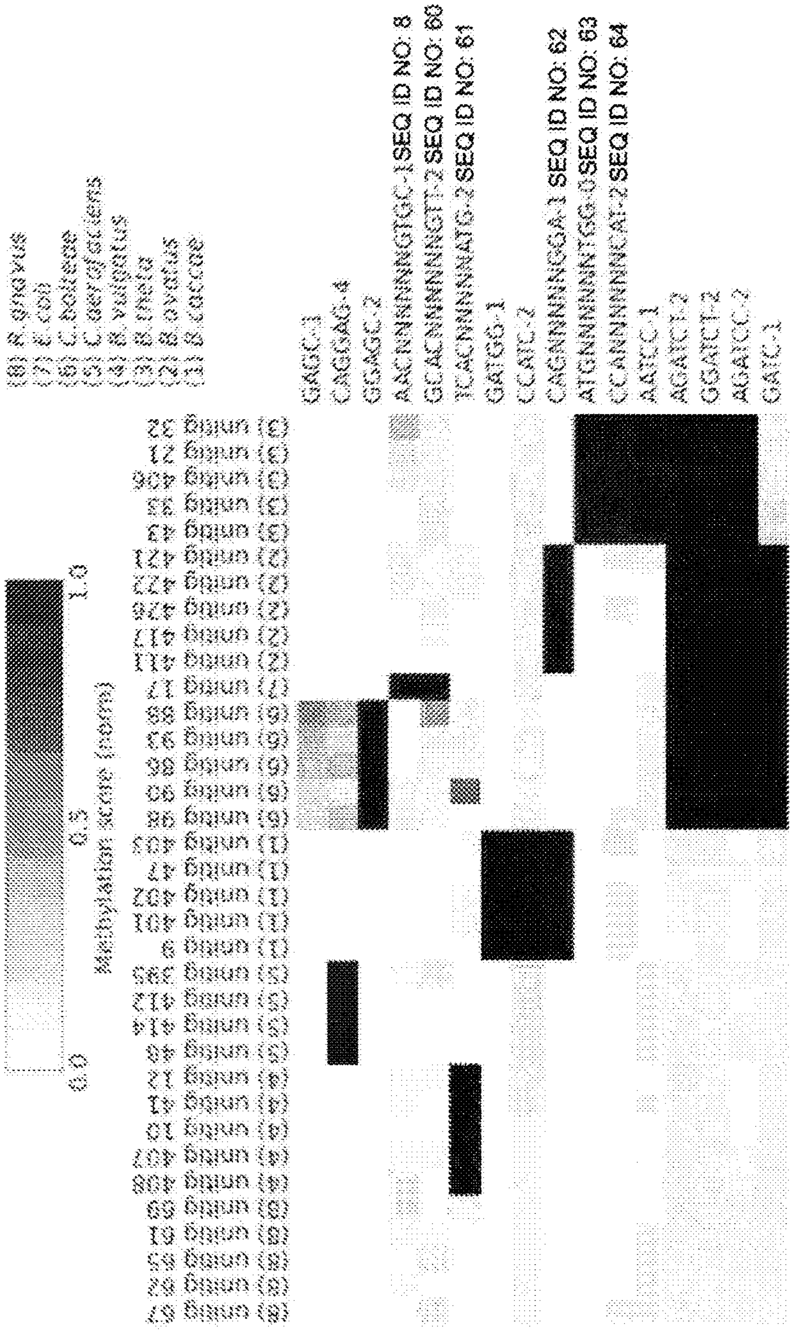

The reads were combined and de novo assembly was done using the hierarchical genome-assembly process (HGAP3). The motif filtering procedure of the invention de novo identified 16 motifs from the metagenomic contigs, 14 (87.5%) of which are exact matches to the true methylated motifs (as determined by separate methylation analysis for each species independent from the creation or analyses of the synthetic mixture; (Table 2, below). The remaining two motifs are closely related to and provide similar methylation signals to the true motifs. Hierarchical clustering of the largest contigs from each species and their motif methylations scores shows that among the 16 motifs selected by motif filtering, each species in the mixture has a unique methylation profile (FIG. 2B).

TABLE 2

Motifs from mixture of eight bacterial species that were identified using the motif filtering procedure based on contig-wide methylation profiles. Fourteen of the sixteen motifs identified are confirmed by SMRT Portal methylome analysis and the two remaining motifs are partial versions of two confirmed motifs.

| Motif ID'd by SCp filtering | Confirmed by SMRT Portal | Species |
|---|---|---|
| GATC | Yes | *B. ovatus, E. coli* |
| AGATCC | Yes | *B. thetaiotaomicron* |
| GGATCT | Yes | *B. thetaiotaomicron* |
| AGATCT | Yes | *B. thetaiotaomicron* |
| AATCC | Yes | *B. thetaiotaomicron* |
| CCANNNNNNCAT (SEQ ID NO: 2) | Yes | *B. thetaiotaomicron* |

TABLE 2-continued

Motifs from mixture of eight bacterial species that were identified using the motif filtering procedure based on contig-wide methylation profiles. Fourteen of the sixteen motifs identified are confirmed by SMRT Portal methylome analysis and the two remaining motifs are partial versions of two confirmed motifs.

| Motif ID'd by SCp filtering | Confirmed by SMRT Portal | Species |
|---|---|---|
| ATGNNNNNNTGG (SEQ ID NO: 3) | Yes | *B. thetaiotaomicron* |
| CAGNNNNNGGA (SEQ ID NO: 4) | Yes | *B. caccae, B. ovatus* |
| CCATC | Yes | *B. caccae* |
| GATGG | Yes | *B. caccae* |
| TCACNNNNNATG (SEQ ID NO: 5) | No (but related to CACNNNNNATG (SEQ ID NO: 6)) | *B. vulgatus* |
| GCACNNNNNNGTT (SEQ ID NO: 7) | Yes | *E. coli* |
| AACNNNNNNGTGC (SEQ ID NO: 8) | Yes | *E. coli* |
| GGAGC | Yes | *C. bolteae* |
| CAGGAG | Yes | *C. aerofaciens* |
| GAGC | No (but related to GGAGC) | *C. bolteae* |

To ease visualization and interpretation of high-dimensional features of many metagenomic contigs, dimensionality reduction was used to reduce the feature space to two dimensions that are amenable to plotting. The dimensionality reduction algorithm primarily used in this study is the Barnes-Hut approximation of t-distributed stochastic neighbor embedding (t-SNE) (see Examples), which has already been demonstrated to be effective at segregating metagenomic contigs based on k-mer frequency. Because t-SNE is a non-linear dimensionality reduction algorithm that is designed to preserve local pairwise distances, it differs from linear methods, such as principal components analysis (PCA) that captures global variance, making t-SNE well suited for complex microbiome communities with subpopulation structures that are not effectively captured by PCA.

Figure 2C:
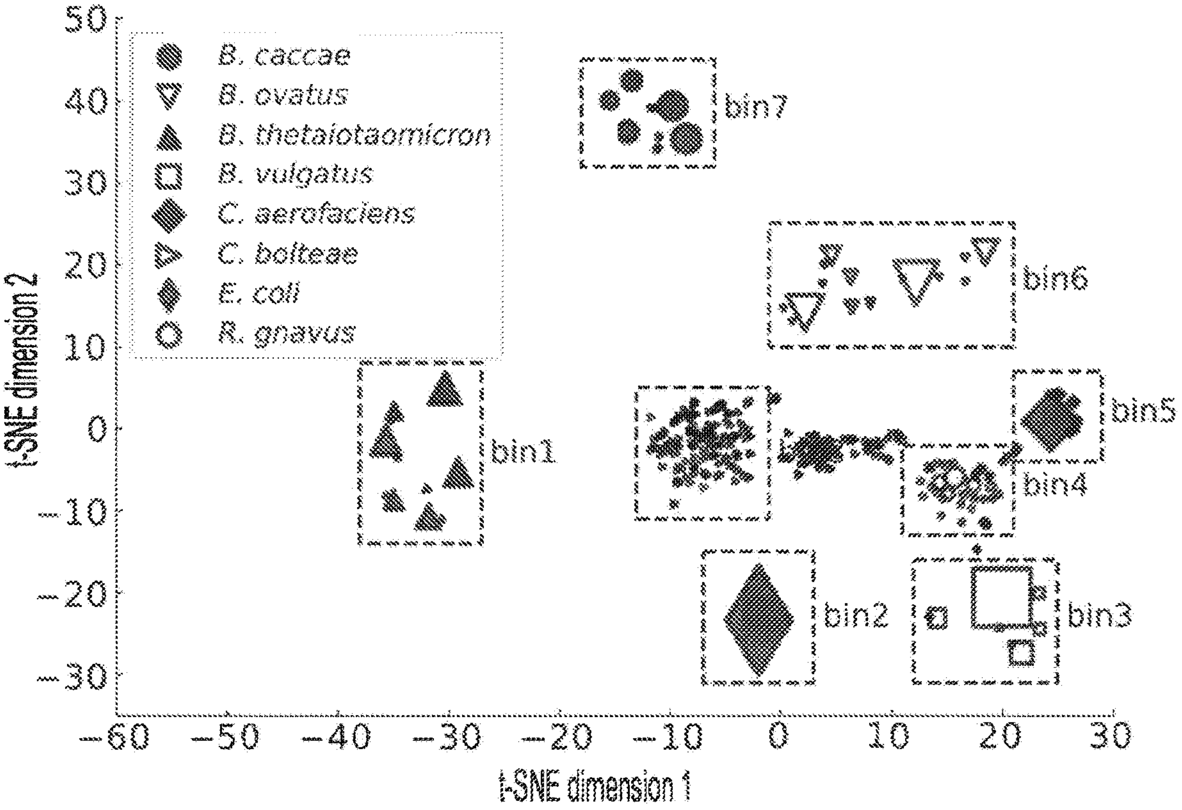
Figure 6:
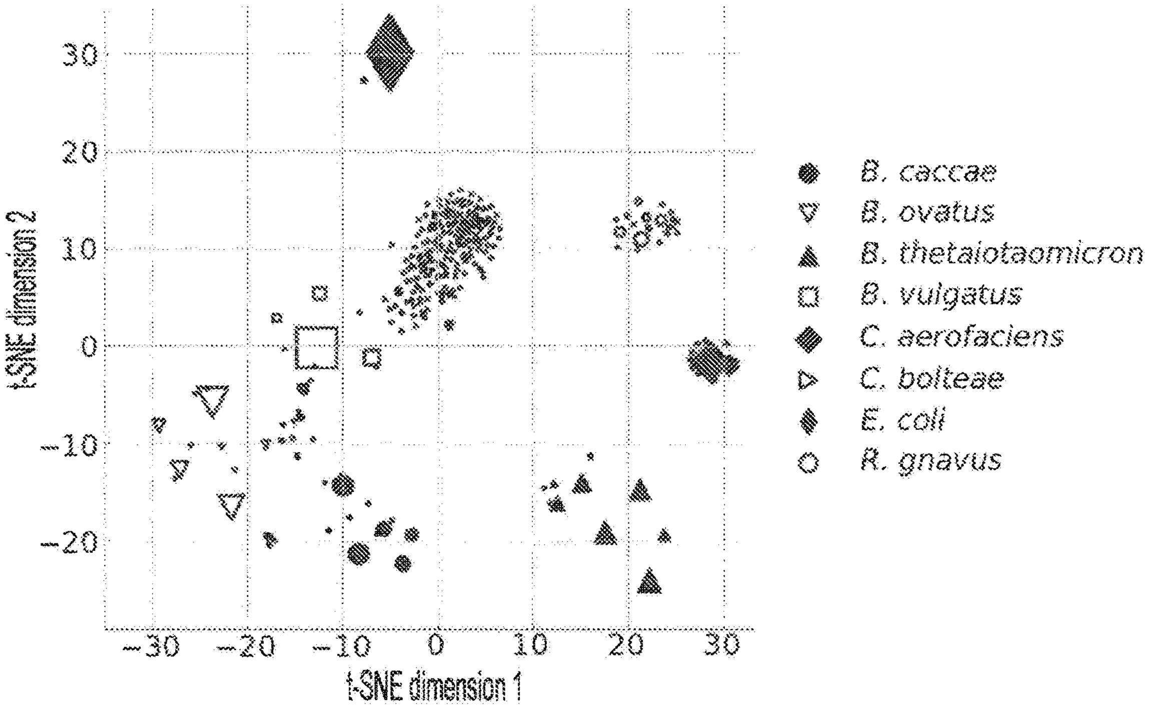
FIG. 6 depicts a t-SNE scatter plot of 5-mer composition profiles for contigs from eight-species mock community.
Figure 7:
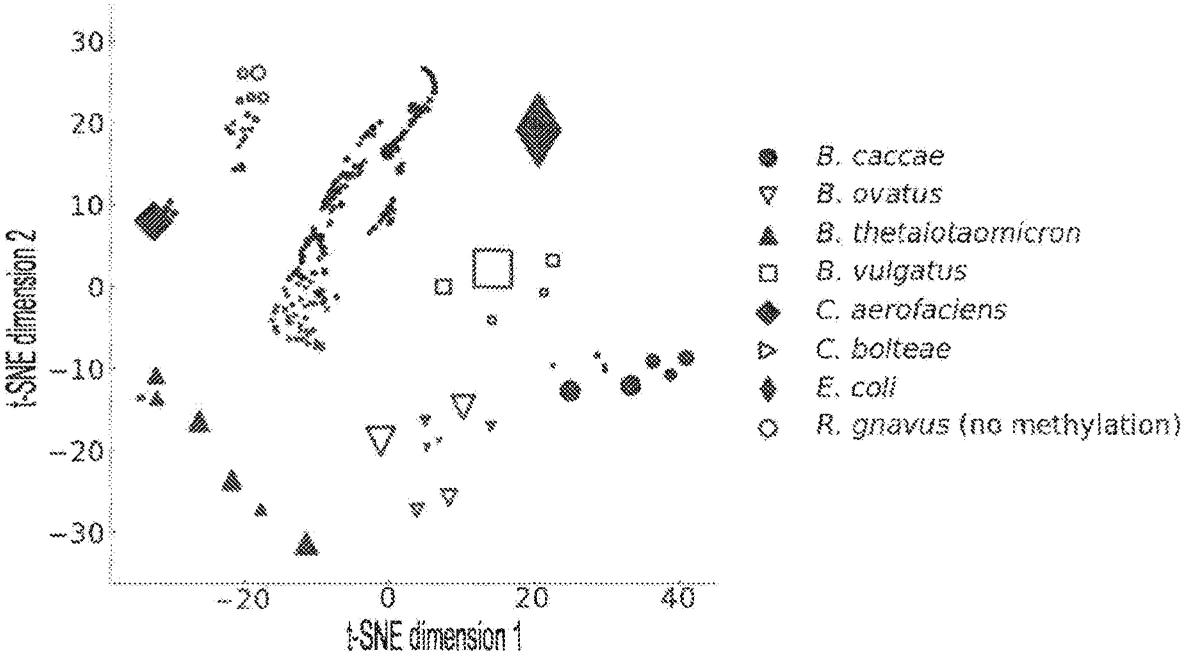
FIG. 7 depicts t-SNE scatter plot of 5-mer composition and contig coverage profiles for contigs from eight-species mock community.

The 2D map generated by applying t-SNE to the matrix of methylation profiles (16 motifs for each contig) reveals contigs that are generally well separated based on their known species (FIG. 2C). Specifically, the four species from the *Bacteroides* genus show remarkably clear separation from each other, despite the fact that the genomes share significant sequence similarity (Table 3, below). This separation of the four *Bacteroides* species is clearer than is possible using composition methods alone (FIG. 6) and cleaner than when the contig coverage values are included with composition (FIG. 7). The methylation-based map results in a cluster silhouette coefficient, which ranges between-1 (significant mixing) and 1 (complete separation), of 0.53, while the composition-based clustering results in a 0.14 silhouette coefficient.

TABLE 3

Average nucleotide identities (ANI) for the members of the eight bacteria mixture. The minimum detectable identity is 75%.

| Organism | NCBI reference sequence | *Bacteroides caccae* | *Bacteroides ovatus* | *Bacteroides thetaiotaomicron* | *Bacteroides vulgatus* | *Collinsella aerofaciens* | *Clostridium bolteae* | *Escherichia coli* | *Ruminococcus gnavus* |
|---|---|---|---|---|---|---|---|---|---|
| *Bacteroides caccae* | GCA_000169015 | 1 | | | | | | | |
| *Bacteroides ovatus* | NZ_CP012938 | 83.82% | 1 | | | | | | |
| *Bacteroides thetaiotaomicron* | NC_004663 | 82.59% | 82.63% | 1 | | | | | |
| *Bacteroides vulgatus* | NC_009614 | 80.98% | 78.52% | 83.16% | 1 | | | | |
| *Collinsella aerofaciens* | GCA_000169035 | <75% | <75% | <75% | <75% | 1 | | | |
| *Clostridium bolteae* | GCA_000154365 | <75% | <75% | <75% | <75% | <75% | 1 | | |
| *Escherichia coli* | NC_000913 | <75% | <75% | <75% | <75% | <75% | <75% | 1 | |
| *Ruminococcus gnavus* | GCA_000169475 | <75% | <75% | <75% | <75% | <75% | <75% | <75% | 1 |

Figure 8:
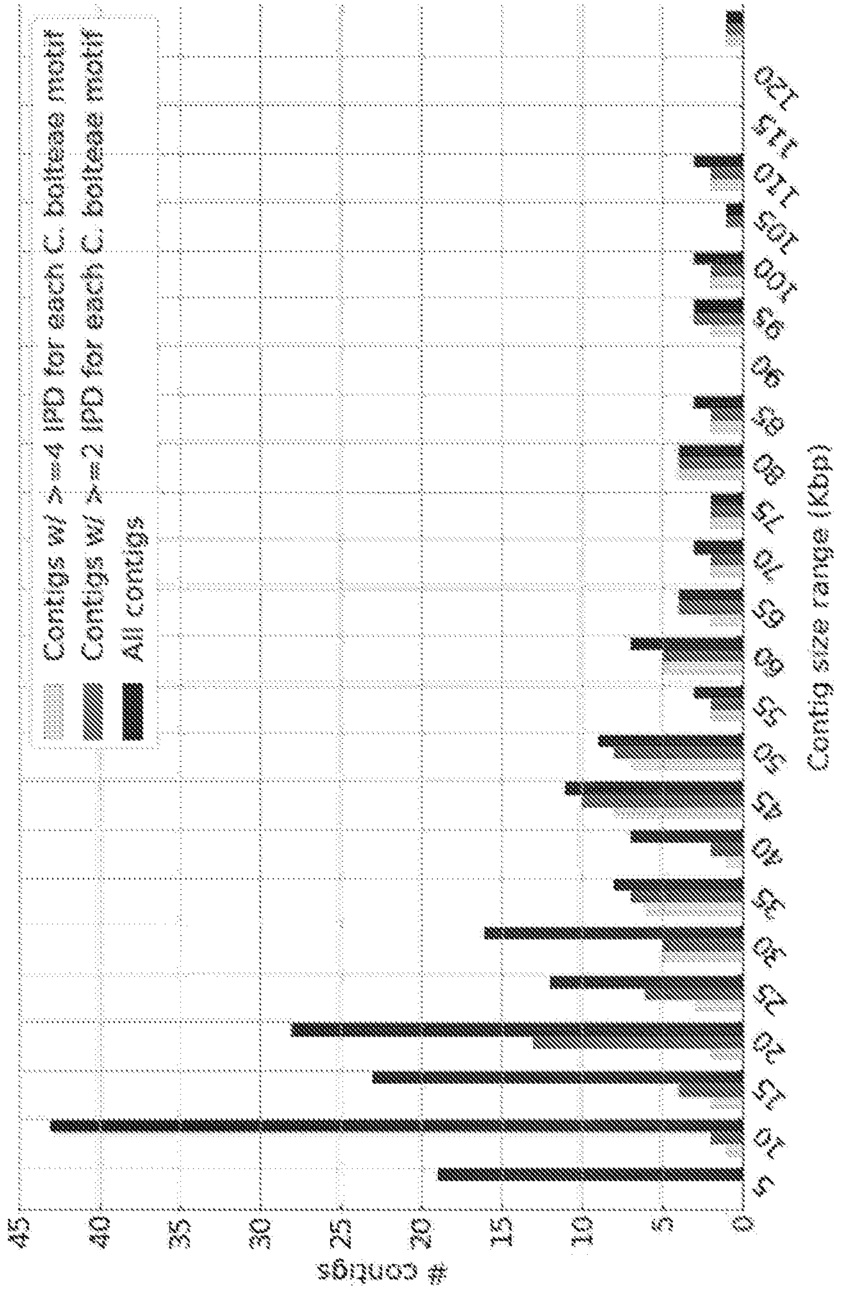
FIG. 8 depicts isolated contigs belonging to *C. bolteae* after de novo assembly of reads from eight bacterial species. As the contig length decreases, it becomes less common for the contig to contain IPD values from the full diversity of motif sites that are methylated in *C. bolteae*, making it increasingly difficult to segregate smaller contigs based on contig methylation patterns alone.

Interestingly, there is some mixing of small contigs that are likely too short to contain IPD values from the full set of methylated motifs for a species. This is supported by the observation that several contigs belonging to *Clostridium bolteae*, which are too small to contain the full diversity of *C. bolteae* methylated motifs (FIG. 8), cluster more closely with *Ruminococcus gnavus*, a species without any detectable methylation motifs. While some organisms will be, like *R. gnavus*, absent any detectable methylation, these are relatively rare.

Methylation Binning Complements Existing Methods in Complex Microbiome

Having demonstrated how methylation profiles can be used for contig binning in a mock metagenomic community, next the approach was applied to examine a microbial community sampled from an adult mouse gut. 16S rRNA sequencing (see Examples) indicated that the sample was complex and dominated by an undefined number of organisms from the S24-7 family of the order Bacteroidales (FIG. 2D). SMRT sequencing reads were assembled using the HGAP3 assembler (Table 4).

TABLE 4

SMRT sequencing details of adult mouse gut microbiome and metagenomic assembly statistics

| | Sequency statistic | | | | | Assembly statistics | | | |
|---|---|---|---|---|---|---|---|---|---|
| Sample | # SMRT cells | # sequenced bases | # reads | Avg. read length (bp) | Avg. subread length (bp) | Num. contigs | Assembly size (bp) | Largest contig (bp) | Contig N50 (bp) |
| Adult mouse gut microbiome | 5 | 6,692,306,779 | 478,273 | 13,992 | 6,768 | 3,847 | 59,087,950 | 2,712,836 | 410,528 |

Figure 2E:
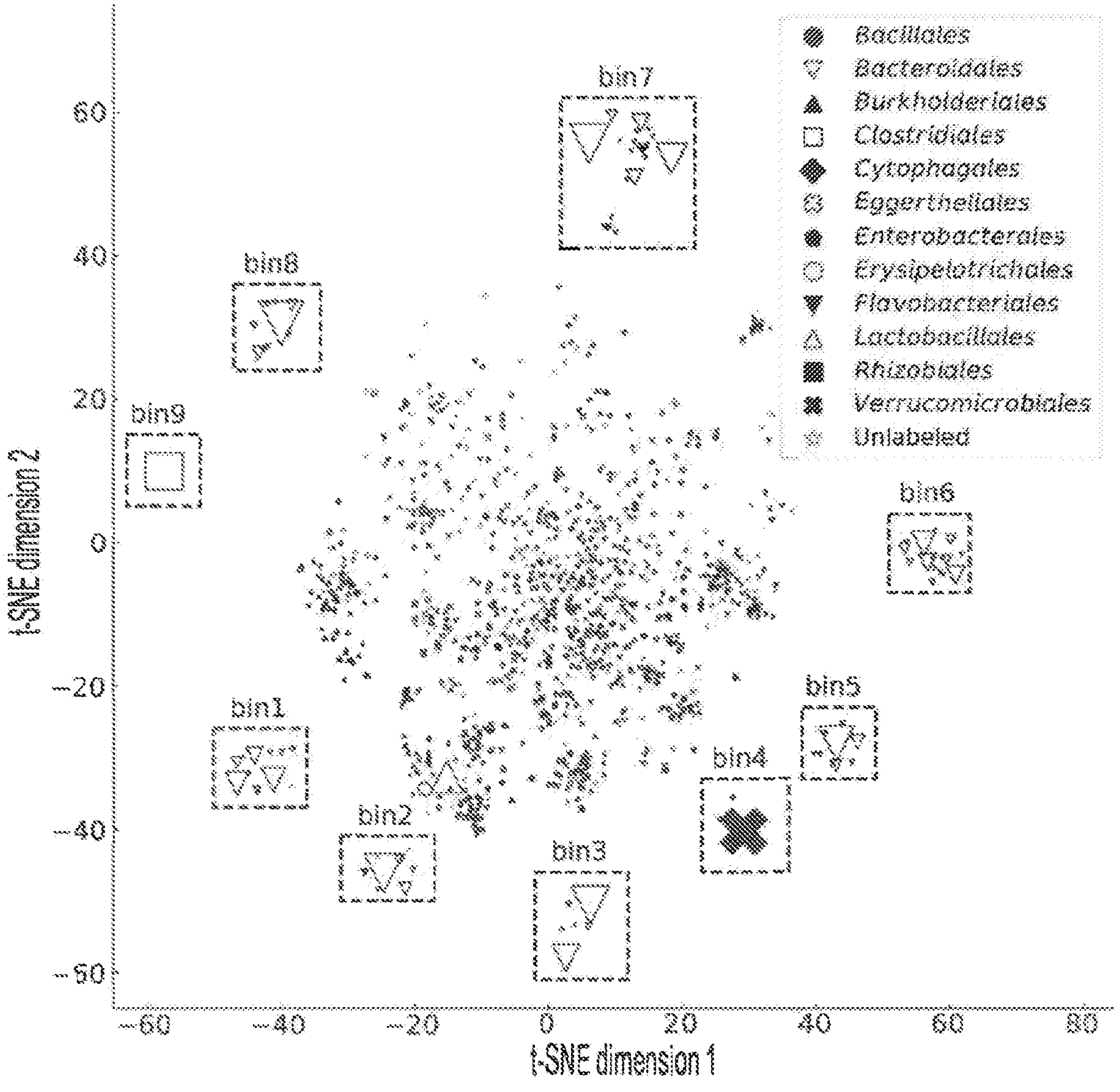
Figure 2F:
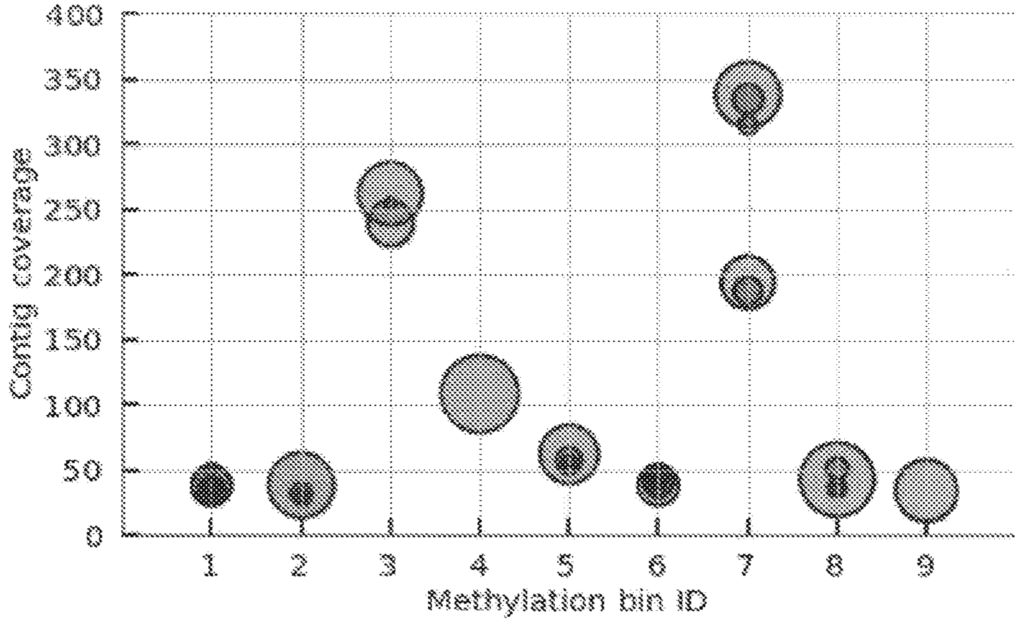

38 methylated motifs were detected from the assembled contigs and visualized the methylation landscape of the sample by using t-SNE to reduce the 38 dimensions to a 2D scatter plot (FIG. 2E). The resulting scatter plot reveals nine distinct bins of contigs with consistent methylation profiles. In eight of the nine bins, the uniform contig coverage values within each bin support that the contigs correspond to eight single organisms, while the split coverage values in bin7 suggest that it may contain contigs from two different genomes (FIG. 2F).

Next, CheckM was used to assess the genome completeness and contamination of each bin based on single-copy gene counts. Eight of the nine bins have >97% completeness and only bin7 has significant contamination, likely from the second genome in the bin (Table 5, below).

TABLE 5

Nine distinct bins discovered from the adult mouse gut microbiome using DNA methylation profiles. Assembly validation was done using CheckM [Parks et al., Genome Research. 2015] and reflected the presence or absence of a set of single-copy marker genes that is selected based on the detected taxonomic annotation. Significant motifs are those with a mean methylation score across binned contigs greater than 1.6. Mapped mobile genetic elements (MGE) are those with matching methylation profiles to the specified methylation bin (see Examples).

| | Binning statistics | | | | Bin validation | | | Methylation summary | | |
|---|---|---|---|---|---|---|---|---|---|---|
| Bin | Num. contigs | Total bases (bp) | Largest contig (bp) | Contig N50 (bp) | Taxonomic annotation (level) | Completeness (%) | Contamination (%) | Significant motifs | Mean contig-level methylation score | Mapped MGEs |
| 1 | 14 | 4027504 | 1128400 | 1089244 | *Bacteroidales* (order) | 98.68 | 2.26 | ACCG**A**G | 1.85 | 12.7 kb plasmid, 19.1 kb conjugative transposon |
| | | | | | | | | CC**A**SNNNNNNATGT (SEQ ID: NO: 9) | 2.01 | |
| 2 | 9 | 3496584 | 2164130 | 2164130 | *Bacteroidales* (order) | 77.48 | 2.01 | CTGC**A**G | 2.43 | None found |
| 3 | 7 | 3853295 | 2087314 | 2087314 | *Bacteroidales* (order) | 99.43 | 1.13 | TC**A**GNNNNNCCTC (SEQ ID NO: 10) | 1.62 | None found |
| | | | | | | | | CC**A**GNNNNNNVTGG | 2.22 | |

TABLE 5-continued

Nine distinct bins discovered from the adult mouse gut microbiome using DNA methylation profiles. Assembly validation was done using CheckM [Parks et al., Genome Research. 2015] and reflected the presence or absence of a set of single-copy marker genes that is selected based on the detected taxonomic annotation. Significant motifs are those with a mean methylation score across binned contigs greater than 1.6. Mapped mobile genetic elements (MGE) are those with matching methylation profiles to the specified methylation bin (see Examples).

| | Binning statistics | | | | Bin validation | | | Methylation summary | | |
|---|---|---|---|---|---|---|---|---|---|---|
| Bin | Num. contigs | Total bases (bp) | Largest contig (bp) | Contig N50 (bp) | Taxonomic annotation (level) | Completeness (%) | Contamination (%) | Significant motifs | Mean contig-level methylation score | Mapped MGEs |
| | | | | | | | | (SEQ ID NO: 11) | | |
| | | | | | | | | CCAGNNNNNNRTGG (SEQ ID NO: 12) | 2.50 | |
| 4 | 5 | 2759439 | 2712836 | 2712836 | *Actinobacteria* (phylum) | 97.96 | 0.68 | GATTNNNNNCAGT (SEQ ID NO: 13) | 3.11 | None found |
| | | | | | | | | GATTNNNNNNAGT (SEQ ID NO: 14) | 2.93 | |
| 5 | 10 | 3378404 | 1873721 | 1873721 | *Bacteroidales* (order) | 97.55 | 1.76 | AGCANNNNNNRTC (SEQ ID NO: 15) | 1.98 | None found |
| | | | | | | | | GACNNNNNNTGCT (SEQ ID NO: 16) | 2.27 | |
| 6 | 16 | 4441324 | 1159367 | 764722 | *Bacteroidales* (order) | 98.36 | 1.26 | ATGCAT | 1.76 | None found |
| | | | | | | | | CCANNNNNTCG (SEQ ID NO: 17) | 1.93 | |
| | | | | | | | | AACAGC | 2.80 | |
| 7 | 22 | 6207805 | 2165375 | 1643203 | *Bacteroidales* (order) | 98.24 | 21.52 | GGCAGC | 2.22 | 24.7 kb plasmid, 14.7 kb plasmid, 23.2 kb conjugative transposon |
| | | | | | | | | GTGATG | 2.00 | |
| 8 | 14 | 3913657 | 2565370 | 2565370 | *Bacteroidales* (order) | 97.22 | 2.77 | AGATGA | 2.21 | 14.3 kb plasmid, 15.8 kb plasmid, 21.1 kb conjugative transposon |
| | | | | | | | | AGATG | 1.94 | |
| | | | | | | | | GATGGY | 1.94 | |
| | | | | | | | | AGATGT | 1.72 | |
| | | | | | | | | KAGATG | 2.08 | |
| | | | | | | | | TAGATG | 1.96 | |
| | | | | | | | | TGATGG | 1.71 | |
| | | | | | | | | GATGG | 1.81 | |
| 9 | 1 | 2021078 | 2021078 | 2021078 | *Bacteria* (kingdom) | 99.19 | 0.00 | CGAAG | 2.46 | None found |
| | | | | | | | | GAAGNNNNNACGT (SEQ ID NO: 18) | 2.18 | |
| | | | | | | | | TGMAGG | 2.48 | |
| | | | | | | | | CGAGNNNNNNCCTT (SEQ ID NO: 19) | 1.69 | |
| | | | | | | | | ACCATC | 2.20 | |

Figure 9:
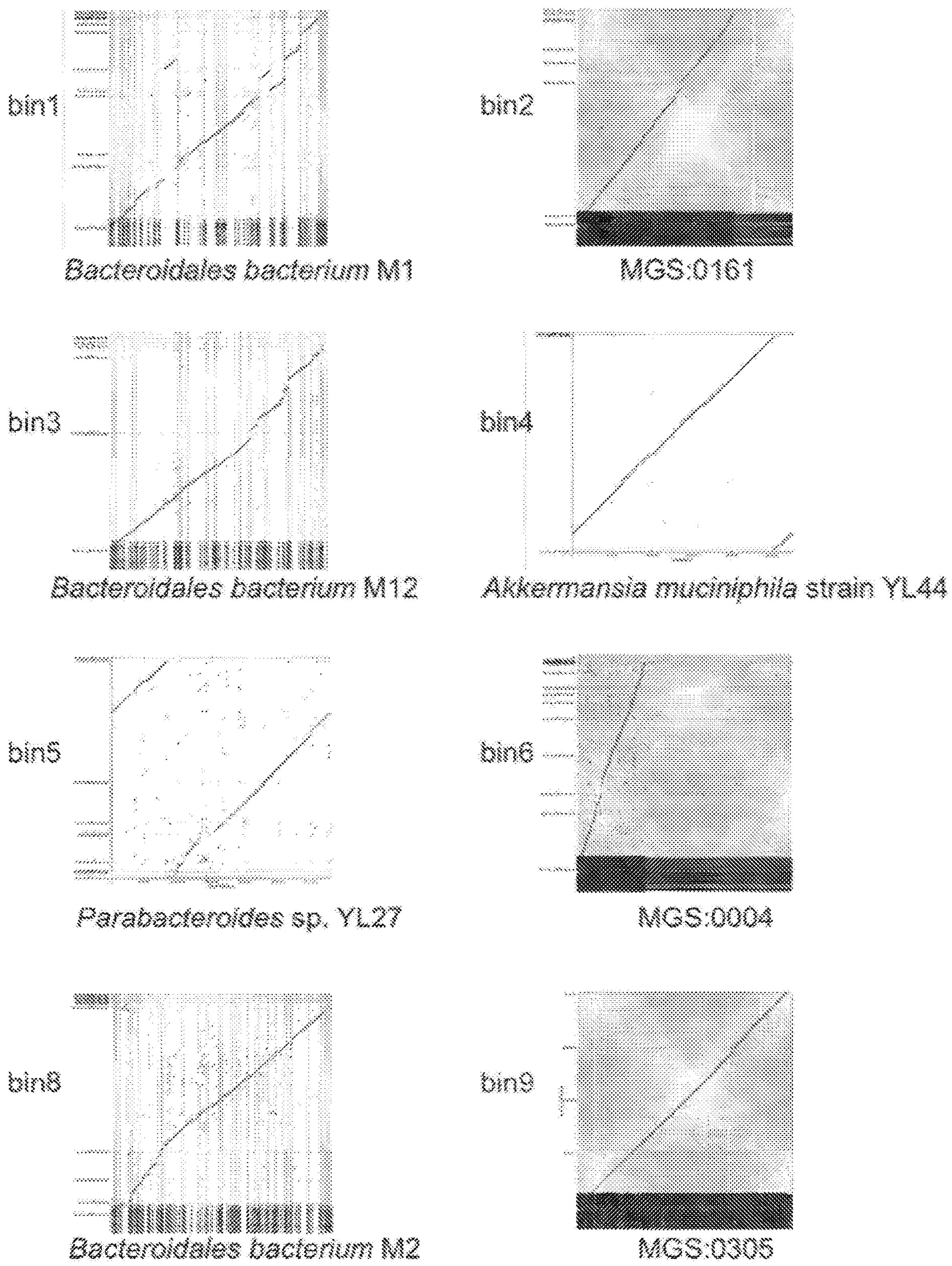
FIG. 9 depicts dot plot visualizations created using mummerplot that show the top reference alignment for bins isolated from the mouse gut microbiome metagenomic assembly using only methylation profiles. See FIG. 10 for details of these alignments and the matching reference sequences.

Querying the contig sequences in each bin against a manually curated set of 591 publicly available mouse gut microbial references revealed significant reference hits with eight of the nine bins (FIG. 9; Table 6, below), providing further support that the bins identified using methylation profiles represent the genomes of distinct organisms.

TABLE 6

Annotation details for the nine bins identified from the mouse gut using methylation profiles. Reference sequences from Ormerod et al. and Xiao et al. are highly fragmented assemblies. See Examples for description of alignment procedures.

| Bin | Top reference match | Coverage of binned sequence (%) | Accession | Source |
|---|---|---|---|---|
| 1 | *Bacteroidales bacterium* M1 | 64.60 | GCA_001689425.1 | Ormerod et al. |
| 2 | MGS: 0161 | 47.78 | N/A | Xiao et al. |
| 3 | *Bacteroidales bacterium* M12 | 62.01 | GCA_001689575.1 | Ormerod et al. |
| 4 | *Akkermansia muciniphila* strain YL44 | 91.31 | CP015409.2 | Uchimura et al. |
| 5 | *Parabacteroides* sp. YL27 | 77.31 | CP015402.2 | Uchimura et al. |
| 6 | MGS: 0004 | 37.92 | N/A | Xiao et al. |
| 7 | N/A | N/A | N/A | N/A |
| 8 | *Bacteroidales bacterium* M2 | 64.10 | GCA_001689415.1 | Ormerod et al. |
| 9 | MGS: 0305 | 44.55 | N/A | Xiao et al. |

Bin4 and bin5 have high-quality, nearly full-length matches with the finished genomes for *Akkermansia mucinophilia* YL-44 (average nucleotide identity (ANI)=98.94%) and Parabacteroides sp. YL-27 (ANI=98.43%), respectively. The remaining six bins have high-quality matches with genome assemblies of species that have been identified in the mouse gut in other studies but lack finished reference sequences. Three of these six bins have full-length matches with three draft assemblies of uncultured members of the Bacteroidales S24-7 family: bin1 matches Bacteroidales bacterium M1 (ANI=98.63%), bin3 matches Bacteroidales bacterium M12 (ANI=98.45%), and bin8 matches Bacteroidales bacterium M2 (ANI=98.24%). The final three bins have high-quality matches with three unidentified metagenomic species (MGS) previously binned in a large study of mouse gut microbiomes: bin2 matches MGS: 0161 (ANI=99.41%), bin8 matches MGS: 0004 (ANI=99.38%), and bin9 matches MGS: 0305 (ANI=99.96%). The seven Bacteroidales bins all share high ANI with each other (81-91% ANI), but at values suggesting inter-rather than intraspecies relationships (Table 7).

TABLE 7

Average nucleotide identity (ANI) values for contigs contained in each of the nine methylation bins from the mouse gut microbiome.

| Bin | Taxonomic annotation (order) | 1 | 2 | 3 | 4 | 5 | 6 | 7 | 8 | 9 |
|---|---|---|---|---|---|---|---|---|---|---|
| 1 | *Bacteroidales* | 1 | | | | | | | | |
| 2 | *Bacteroidales* | 88.16% | 1 | | | | | | | |
| 3 | *Bacteroidales* | 83.72% | 84.87% | 1 | | | | | | |
| 4 | *Verrucomicrobiales* | <75% | <75% | <75% | 1 | | | | | |
| 5 | *Bacteroidales* | 87.70% | 81.51% | 82.73% | <75% | 1 | | | | |
| 6 | *Bacteroidales* | 89.08% | 82.24% | 89.82% | <75% | 88.56% | 1 | | | |
| 7 | *Bacteroidales* | 89.83% | 81.69% | 90.46% | <75% | 91.27% | 86.30% | 1 | | |
| 8 | *Bacteroidales* | 80.35% | 79.46% | 85.32% | <75% | 83.58% | 85.70% | 87.08% | 1 | |
| 9 | *Clostridiales* | <75% | <75% | <75% | <75% | <75% | <75% | <75% | <75% | 1 |

Because the only other family of Bacteroidales identified in the sample by 16S sequencing was the family Rikenellaceae at 2.12% abundance, it is likely that these seven highly contiguous genome bins all belong to the poorly characterized S24-7 family of Bacteroidales that dominated the 16S abundance profile for the sample (FIG. 2D). Quality alignment of the bin5 contigs to the reference for Parabacteroides sp. YL-27 was observed, which is classified as belonging to the closely related Bacteroidales family Tannerellaceae, but there is some apparent divergence in the alignment that raises doubts about it being an exact match (FIG. 9). Collectively, these comprehensive evaluations demonstrate that the nine bins isolated using methylation profiles represent highly contiguous draft assemblies for organisms that were previously uncharacterized or only represented by fragmented WGS assemblies.

Figure 11:
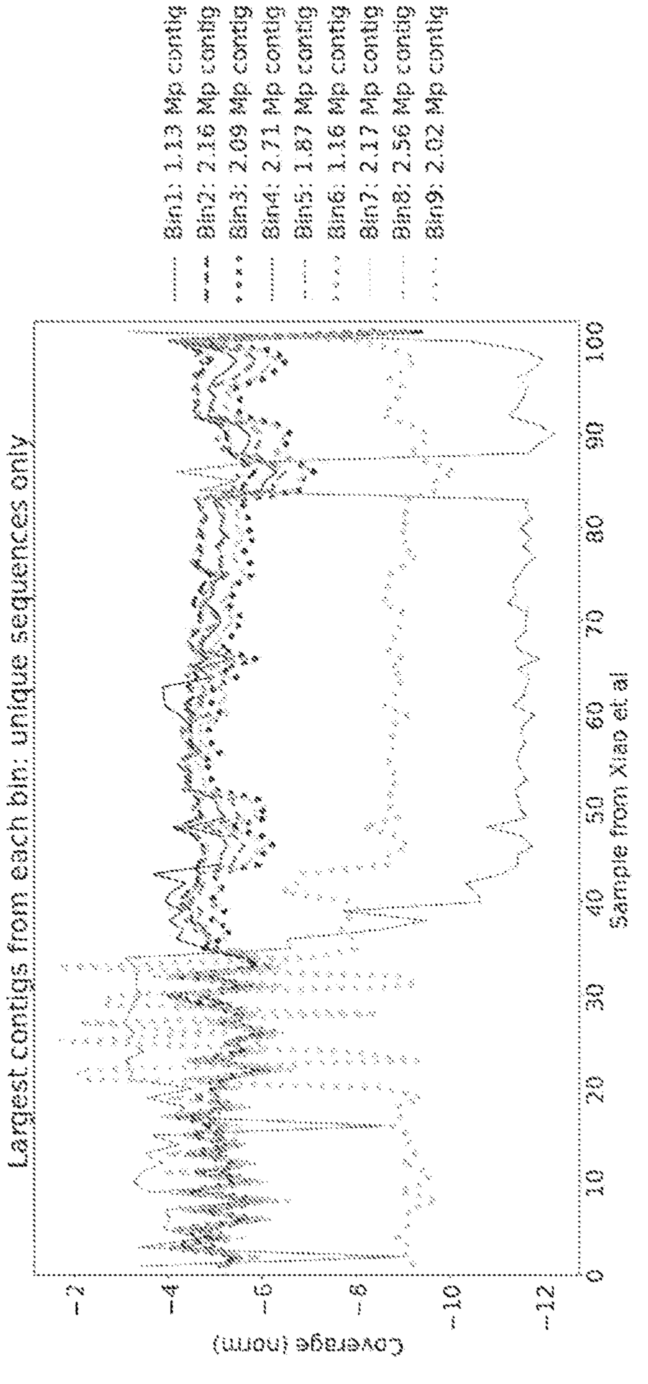
FIG. 11 depicts coverage profiles across 100 publicly available mouse gut microbiome samples from Xiao et al [Xiao et al. Nature Biotechnology, 2015]. Each line represents the coverage for the largest contig in each of the nine bins isolated from the mouse gut microbiome metagenomic assembly. Coverage values are calculated from only unique sequences in order to avoid ambiguous mappings and errant coverage values (see Examples).

Next, the mouse gut microbiome community was explored by leveraging the complementarity of methylation-based binning with existing methods that utilize differential coverage and sequence composition, such as CONCOCT, GroopM, and MetaBAT, which have been demonstrated to be powerful methods for isolating genomes in complex metagenomic samples. Illumina WGS data from 100 publicly available mouse gut samples was aligned to the assembled contigs in order to generate coverage values for each sample. CONCOCT was then applied, which combines contig 4-mer frequency profiles with the coverage profiles to call genome bins. This analysis generated high-quality bins of near-complete genomes for several organisms, including members of the order Clostridiales (mapped to MGS: 0305), Verrucomicrobiales (mapped to *A. mucinophilia* YL-44), and two organisms that do not have methylation bins, Burkholderiales and Lactobacillales (FIG. 10; Table 8, below). However, CONCOCT assigned multiple Bacteroidales genomes to a single bin containing 28 Mbp of sequence. A further analysis showed that the co-binning of several Bacteroidales genomes by CONCOCT is due to the high similarity in their abundance profiles across microbiome samples, even after excluding genomic regions where sequence similarity might cause reads to map to multiple Bacteroidales genomes (FIG. 11 and Examples). Therefore, although differential coverage binning proved very effective for binning many organisms in the sample, it did not effectively handle organisms with similar coverage covariance profiles.

TABLE 8

CONCOCT binning results for the mouse gut microbiome metagenomic assembly. Assembly validation done using CheckM and methylation motifs discovered by using the mBin pipeline to discover bin-level motifs based on the CONCOCT binning assignments.

| | Binning statistics | | | | Assembly validation | | | Methylation summary | |
|---|---|---|---|---|---|---|---|---|---|
| Bin | Num. contigs | Assembly size (bp) | Largest contig (bp) | Contig N50 (bp) | Taxonomic annotation (order) | Completeness (%) | Contamination (%) | Significant motifs | Bin-level methylation |
| 0 | 145 | 501120 | 75317 | 4031 | None | 2.08 | 0.00 | | |
| 1 | 5 | 9850 | 2381 | 2225 | None | 0.00 | 0.00 | | |
| 2 | 187 | 3944862 | 1689676 | 540544 | *Bacteria* (kingdom) | 91.07 | 59.44 | | |
| 3 | 734 | 4134275 | 153653 | 10779 | *Proteobacteria* (phylum) | 76.65 | 20.20 | GATCNNNNNWMT (SEQ ID NO: 20)<br>GATCNNNNNNWSA (SEQ ID NO: 21) | 2.11<br>2.095 |
| 4 | 61 | 1868872 | 294300 | 63780 | *Lactobacillus* (genus) | 94.46 | 1.55 | | |
| 5 | 35 | 493926 | 48225 | 23089 | None | 0.00 | 0.00 | | |
| 6 | 86 | 297988 | 9894 | 4628 | *Bacteria* (kingdom) | 6.17 | 0.00 | | |
| 7 | 1 | 1560 | 1560 | 1560 | None | 0.00 | 0.00 | | |
| 8 | 1 | 4249 | 4249 | 4249 | None | 0.00 | 0.00 | | |
| 9 | 1 | 1870 | 1870 | 1870 | None | 0.00 | 0.00 | | |
| 10 | 188 | 2096122 | 58458 | 19418 | *Bacteroidales* (order) | 68.54 | 0.38 | GAATTC | 2.689 |
| 11 | 152 | 946318 | 23218 | 9777 | *Bacteroidetes* (phylum) | 37.38 | 2.57 | GAAGAG | 2.138 |
| 12 | 2 | 3418 | 2294 | 2294 | None | 0.00 | 0.00 | | |
| 13 | 223 | 28112527 | 2565370 | 1128400 | None | 100.00 | 566.11 | | |
| 14 | 1 | 4486 | 4486 | 4486 | None | 0.00 | 0.00 | | |
| 15 | 1 | 6685 | 6685 | 6685 | None | 0.00 | 0.00 | | |
| 16 | 204 | 1184289 | 36417 | 9072 | *Bacteria* (kingdom) | 18.10 | 0.00 | | |
| 17 | 64 | 268751 | 70729 | 5465 | *Bacteria* (kingdom) | 10.53 | 0.00 | | |

TABLE 8-continued

CONCOCT binning results for the mouse gut microbiome metagenomic assembly. Assembly validation done using CheckM and methylation motifs discovered by using the mBin pipeline to discover bin-level motifs based on the CONCOCT binning assignments.

| | Binning statistics | | | | Assembly validation | | | Methylation summary | |
|---|---|---|---|---|---|---|---|---|---|
| Bin | Num. contigs | Assembly size (bp) | Largest contig (bp) | Contig N50 (bp) | Taxonomic annotation (order) | Completeness (%) | Contamination (%) | Significant motifs | Bin-level methylation |
| 18 | 51 | 147804 | 7503 | 3224 | None | 0.00 | 0.00 | | |
| 19 | 151 | 875211 | 25211 | 9411 | *Clostridiales* (order) | 36.98 | 0.00 | CAAATC | 2.178 |
| 20 | 4 | 2109367 | 2021078 | 2021078 | *Actinobacteria* (phylum) | 99.19 | 0.00 | ACCATC<br>TGMAGG<br>CGAAG | 2.076<br>2.424<br>2.425 |
| 21 | 145 | 588131 | 17914 | 6380 | *Clostridiales* (order) | 20.11 | 0.00 | | |
| 22 | 169 | 594449 | 12355 | 4432 | *Bacteria* (kingdom) | 10.40 | 0.00 | | |
| 23 | 301 | 1538261 | 377571 | 6958 | *Bacteria* (kingdom) | 17.24 | 0.00 | | |
| 24 | 4 | 6854 | 2695 | 1741 | None | 0.00 | 0.00 | | |
| 25 | 216 | 3624628 | 1873721 | 1873721 | *Bacteria* (kingdom) | 79.31 | 29.45 | | |
| 26 | 180 | 1591856 | 50182 | 14209 | *Lactobacillales* (order) | 53.09 | 1.05 | | |
| 27 | 58 | 3374016 | 2712836 | 2712836 | *Bacteria* (kingdom) | 97.96 | 5.10 | ACTNNNNNNA ATC (SEQ ID NO: 22)<br>GAAATC<br>ACCANNNNNA ATC (SEQ ID NO: 23)<br>GAATTC | 2.214<br>2.017<br>2.028<br>2.059 |
| 28 | 104 | 460003 | 17088 | 6433 | *Bacteria* (kingdom) | 15.52 | 0.00 | TTTAAA | 2.35 |

Collectively, the above analyses highlight the great discriminative power of methylation-based binning and its complementarity with existing methods for improving binning resolution in complex microbiome samples. In recognition of this, the present analysis pipeline was extended to assess methylation profiles at the level of reads, contigs and bins, where the binning assignments can come from various differential coverage binning software. This approach allowed to discover eight additional motifs at the bin level that were not detectable by focusing on individual contigs (Table 8, above).

An analysis of an infant gut microbiome was also performed to illustrate additional ways in which methylation profiles can be integrated with sequence composition features (see Example 1).

Linking MGEs to their Host Species Using Methylation Profiles

Bacterial communities often contain a significant extra-chromosomal genetic potential in the form of mobile genetic elements (MGEs). MGEs may include, without limitation, plasmids, transposons (including class I or retrotransposons, class II or DNA transposons, and insertion sequences), bacteriophages (including bacteriophage elements such as Mu), and introns (including group I introns and group II introns).

Transposons (transposable elements, or TEs) are DNA sequences that can change their position within a genome, sometimes creating or reversing mutations and altering the cell's genetic identity and genome size. It has been shown that transposons are important in genome function and evolution. Transposons are also useful to researchers as a means to alter DNA inside a living organism. There are at least two classes of TEs: Class I TEs or retrotransposons generally function via reverse transcription, while Class II TEs or DNA transposons encode the protein transposase, which they require for insertion and excision, and some of these TEs also encode other proteins.

Bacteriophages (phages) are viruses that infect and replicate within a bacterium. Bacteriophages are composed of proteins that encapsulate a DNA or RNA genome, and may have relatively simple or elaborate structures. Their genomes may encode as few as four genes, and as many as hundreds of genes. Phages replicate within the bacterium following the injection of their genome into its cytoplasm.

Bacteriophages are ubiquitous viruses, found wherever bacteria exist. It's estimated there are more than 1031 bacteriophages on the planet.

Plasmids are small (typically 1-200 kbp), circular, and highly mobile DNA elements can be transferred among host bacteria during conjugation events or through natural transformation of extracellular plasmids into competent cells, making them an important mediator of HGT in bacteria. The genes encoded by plasmids can confer antibiotic resistance, encode virulence factors or provide specific metabolic functions that allow the host cell to survive under conditions that would otherwise be hostile. If a plasmid has a broad range of acceptable host species, the genes encoded by that plasmid, for instance those conferring antibiotic resistance, can be added to the genetic repertoire of a large number of species. It is therefore critically important to determine the host species of plasmids in microbiomes, as this information not only reflect the full genetic catalog of the host, but can also be used to track the transmission of antibiotic resistance elements across different members of a bacterial community.

Figure 3A:
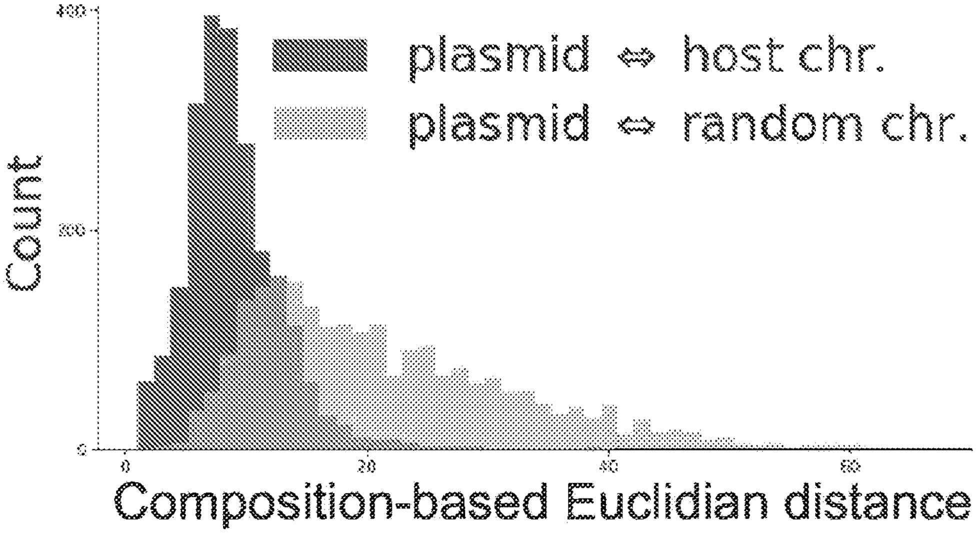
FIGS. 3A-3E depict methylation profile-based mapping between plasmids and the chromosomal DNA of their host species in a microbiome sample.

MGE replication can be independent of chromosomal replication, meaning that the sequenced coverage of, e.g., a plasmid will likely differ significantly from the sequenced coverage of the chromosomal contigs of its host. Furthermore, empirical evidence supports the hypothesis that sequence composition alone is often not capable of mapping a plasmid to its host in a metagenomic setting. By examining the WGS sequencing data from 2,278 plasmids and the chromosomes of their host species in the REBASE database, it was observed that the plasmid sequence composition profile (i.e. the vector of 5-mer frequencies) can differ significantly from that of the host chromosome (FIG. 3A). While the majority of Euclidian distances (d) between plasmid composition profiles and those of their host chromosome fell between 5 and 10, many greatly exceeded that distance and fell under the empirical distribution created by calculating sequence distance between plasmids and randomly sampled chromosomes (see Examples). Highly dissimilar composition between host and plasmid might suggest a recent HGT event where the plasmid was acquired from a distant donor species. However, even in cases of moderate dissimilarity between host chromosome and plasmid sequence composition, there is not a clear strategy for determining which organism might be host to a particular plasmid.

Figure 3B:
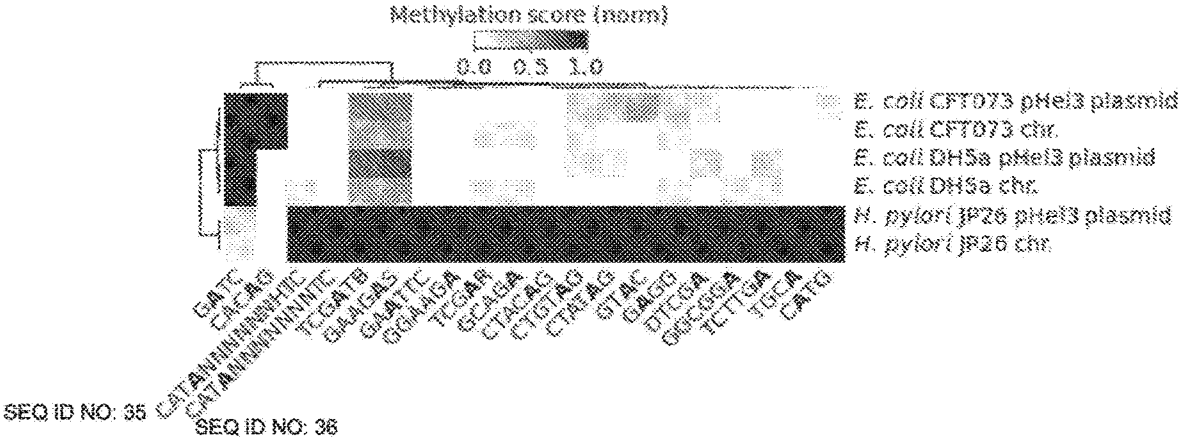

Due to the difficulty of resolving complex repeats and mobile genetic elements, assembling complete plasmid sequences using short-read technologies has proved challenging. While SMRT sequencing is capable of generating high-quality, closed plasmid assemblies from clinical isolates, little work has been done to generate whole plasmid sequences from a metagenomic sample and associate the plasmids to their host bacterial species in the community. To do this, the present invention takes advantage of the fact that plasmid DNA and the chromosomal DNA of the bacterial host are both methylated by the same set of MTases. The result is that the methylation profiles of the plasmids match the methylation profile of its host bacterium. This phenomenon is demonstrated by transforming the 5.5 kbp plasmid pHel3 from *Escherichia coli* DH5α into *E. coli* CFT073 and *Helicobacter pylori* JP26. In each case, SMRT sequencing was used (Table 9, below) to show that the methylation profile of pHel3 inherits that of its new host strain (FIG. 3B).

TABLE 9

SMRT sequencing details for *H. pylori* JP26, *E. coli* DH5a, and *E. coli* CFT073 chromosomal and plasmid DNA samples.

| Strain/DNA source | NCBI reference sequence | # SMRT cells | # sequenced bases | # reads | Avg. read length (bp) | Avg. subread length (bp) | Genome coverage |
|---|---|---|---|---|---|---|---|
| *E. coli* DH5a/ chromosomal | CP017100.1 | 1 | 1,212,827,005 | 47,318 | 25,631 | 1,334 | 142.6 |
| *E. coli* CFT073/ chromosomal | AE014075.1 | 2 | 154,178,427 | 52,598 | 2,931 | 1,383 | 8.74 |
| *H. pylori* JP26/ chromosomal | NC_000915.1 | 1 | 1,694,920,047 | 75,231 | 22,529 | 1,588 | 592.89 |
| *E. coli* DH5a/ pHel3 | N/A | 1 | 1,626,506,858 | 70,100 | 23,202 | 1,323 | 171,275.55 |
| *E. coli* CFT073/ pHel3 | N/A | 1 | 230,674 | 262 | 880 | 958 | 26.21 |
| *H. pylori* JP26/ pHel3 | N/A | 1 | 2,147,318,370 | 94,140 | 22,809 | 2,070 | 3,114.98 |

Figure 3C:
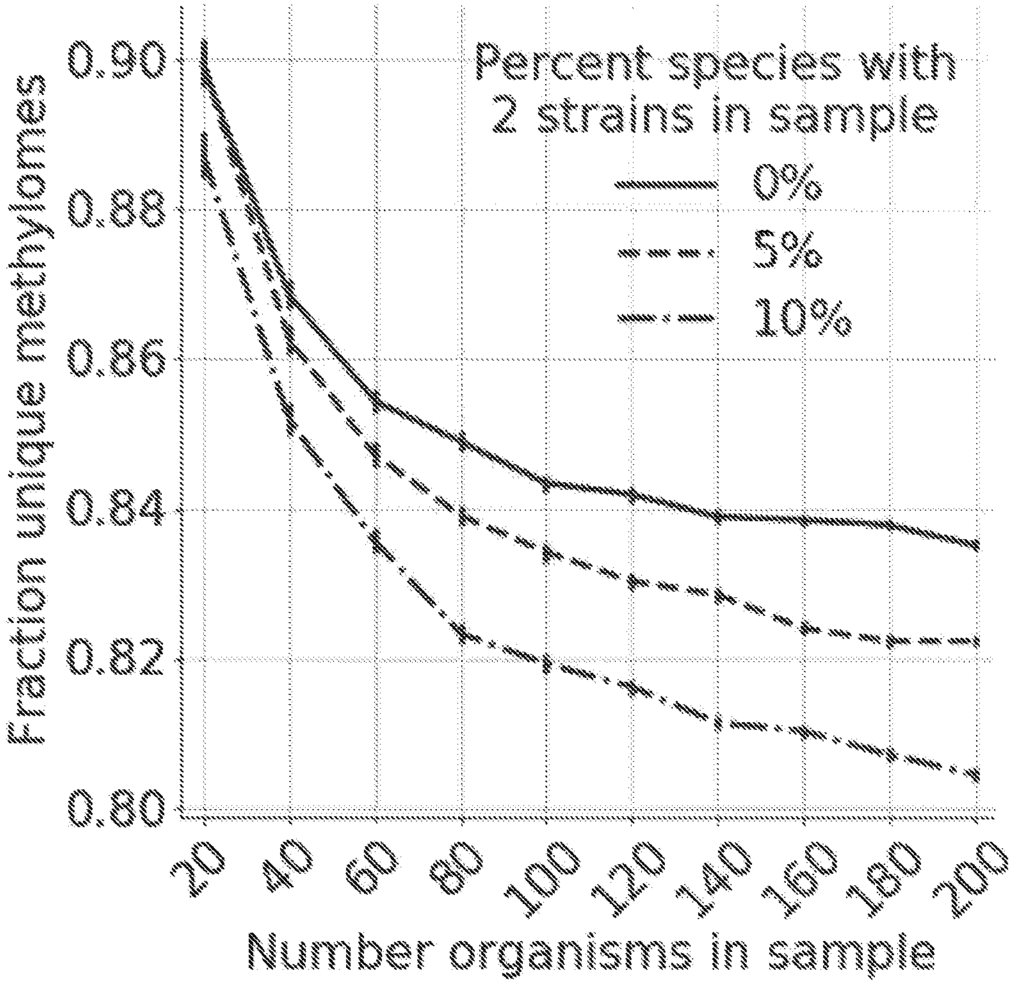
Figure 3D:
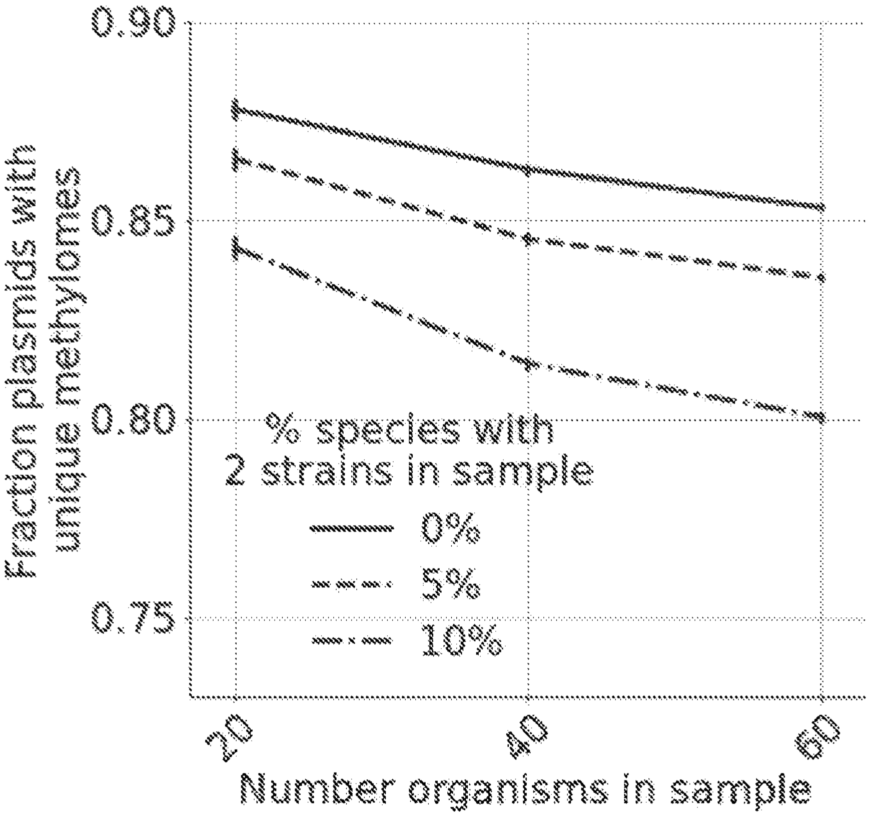

In order to evaluate the general potential of using methylation profiles for mapping plasmids in a community, the wealth of publicly available SMRT sequenced bacteria in the REBASE database was next surveyed, which consists of the assembled sequences and the observed methylated motifs for 878 genomes and 232 plasmids. Because successful mapping of a plasmid to its host requires a sufficient diversity of methylated motifs within a specific community, communities of different sizes were simulated by randomly selecting entries in the REBASE database and assessed the methylome diversity in each mock community. As the number of organisms in a community increases, the number of organisms with unique methylomes, expressed as a fraction of the community size, decreases but still remains fairly high even in communities consisting of 100 species (FIG. 3C). As expected, the decrease is more pronounced when multiple strains of a species are added to a community. Similar values of methylome uniqueness are observed when surveying only organisms in REBASE that have at least one known plasmid (FIG. 3D).

Figure 3E:
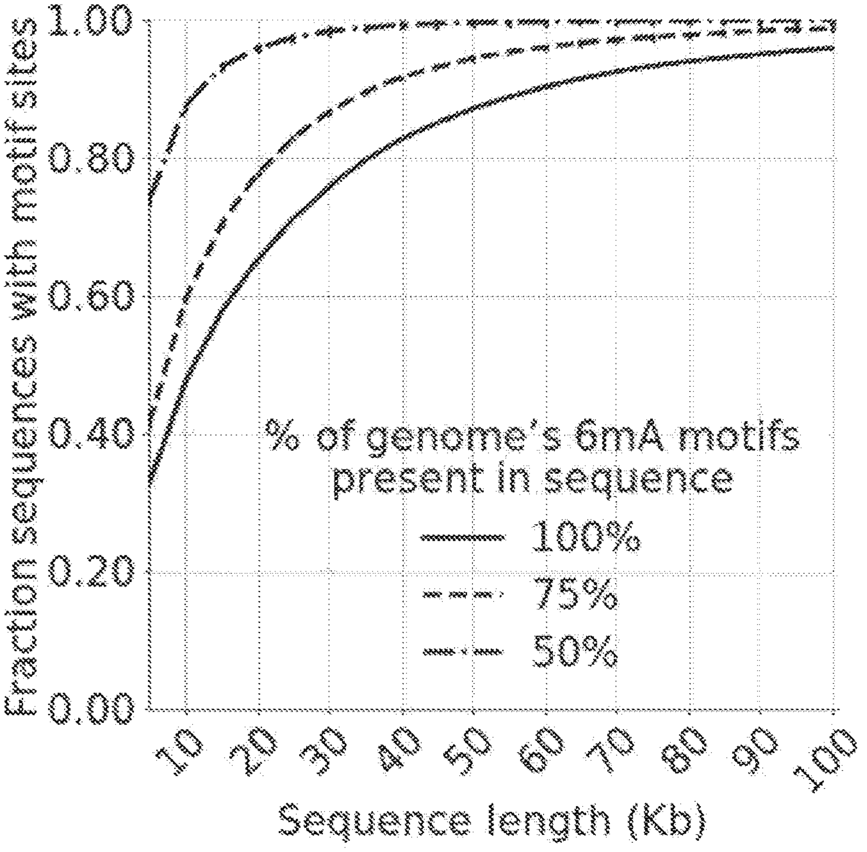

Plasmid size is another consideration for methylation-based host mapping, as shorter plasmids are less likely to possess instances of the full suite of methylated motifs that can help conclusively demonstrate a matching methylation profile with that of a host genome. Sequences of different lengths were simulated from the REBASE genomes and assessed how frequently these sequences contained the full set of the methylated motifs from the source genome (FIG. 3E). It was found that, on average, 90% of 35 kbp sequences will contain instances of at least three quarters of the 6 mA motifs, while 90% of 60 kbp sequences will capture instances of all the 6 mA motifs. Therefore, the rich methylation profiles required for mapping to a host genome are more likely to occur with larger, rather than smaller, plasmids. However, a partially complete methylation profile (i.e. lacking one or more methylated motifs) might be sufficient to unambiguously map the plasmid to its host if the methylated motifs included in the plasmid sequence are uniquely methylated by the host bacteria in a specific microbiome sample. Additional analysis of methylation motifs in an outbreak strain of *Klebsiella pneumoniae* underscores how methylation profiling could help identify the host of a 362 kb plasmid carrying thirteen antibiotic resistance genes in a metagenomic sample (see Example 2).

Building on the important considerations learned from the above analysis, the methylation-based plasmid-host mapping procedure was first applied using the mock community of eight bacterial species, where the true mappings are known. Six closed circular sequences are identified from the SMRT contigs assembled from the mock community by HGAP3 (see Examples). A confident mapping of a plasmid to a host is defined if contigs accounting for >75% of the host genome contain (1) the same methylated motifs (i.e. motifs with methylation score ≥1.6 calculated from ≥10 IPD values) that are found on the plasmid, and (2) no additional methylated motifs. Using this approach, the correct host was recovered using methylation profiles in four of the six circular contigs (67%), including the only known plasmid in the group, *B. thetaiotaomicron* plasmid p5482 (GenBank accession AY171301.1). The remaining two circular contigs were not mapped to the wrong host, but were just too short (<10 kbp) to contain sufficient motif sites for a conclusively mapping, consistent with the estimations from the above simulation analysis (FIG. 3E).

Next, the methylation-based plasmid-host mapping procedure was applied to the adult mouse gut microbiome sample. 19 contigs between 7-132 kbp were identified, of which eleven are fully circularized and nine are conjugative transposon elements (encoding at least five genes annotated as conjugative transposon-related). Thirteen of these mobile genetic elements (MGE) did not assemble using the original complex metagenomic reads, but were only discovered by isolating the reads that map to contigs in each methylation bin and re-assembling them in a single genome setting (see Examples). Using the same methylation-based criteria defined above, eight of the 19 discovered MGEs were confidently mapped to distinct methylation bins containing genomes from the order Bacteroidales (Table 5, above). These eight mapped MGEs include five highly likely plasmids (<50 kb circular contigs containing origins of replication) and three conjugative transposons. Conjugative transposons are known to play an important role in HGT and the spread of antibiotics in Bacteroidales, and they have been implicated in sequence sharing between multiple Bacteroidales species in the human gut. Collectively, these analyses demonstrate that DNA methylation can be exploited as a novel discriminative feature for MGE-host (e.g., plasmid-host) mapping in complex microbiome samples.

Binning Single-Molecule Long Reads Using Composition and Methylation

Highly variable organism abundances in metagenomic samples often present significant challenges to de novo assembly tools, especially for the low abundance species. Because it can be expected that some community members will not be represented among the assembled contigs, a more complete representation of the community might be achieved by binning unassembled metagenomic sequencing reads alongside the assembled contigs. Multiple tools use unsupervised binning of metagenomic short reads, but the insufficient sequence information content in short reads limits their accuracy and practical applicability outside of very low-complexity metagenomic samples. While third generation sequencing platforms produce amplification-free reads with much longer read lengths, the raw reads are confounded by a high single-pass error rate (typically ~13% for SMRT sequencing). Although it has been shown that longer contig sequences result in greater segregation using 5-mer frequency vectors and t-SNE, it remained a fundamental question whether this would also apply to high-error unaligned SMRT reads.

To evaluate the ability of 5-mer frequency metrics to bin unassembled SMRT reads and assembled contigs together, a synthetic microbiome (mixed DNA from the 20-member Mock Community B) created as part of the Human Microbiome Project (HMP) was first analyzed. The original mock community contained each member in roughly equal proportion, making it an unrealistic mixture. The reads were therefore downsampled (see Examples) to create a distribution of relative abundances that follows a log curve, where the most predominant species, *Streptococcus mutans* (294× coverage), is present at 147 times the abundance of the most minor species, *Rhodobacter sphaeroides* (2× coverage) (FIG. 12; Table 10).

TABLE 10

SMRT sequencing details of the Human Microbiome Project Mock Community B sample, which was selectively downsampled so that the species relative abundances follow a log-curve (see FIG. 9 and Examples).

| Species | NCBI reference sequence | # SMRT cells | # sequenced bases | # reads | Avg. read length (bp) | Genome coverage |
|---|---|---|---|---|---|---|
| *Acinetobacter baumannii*, strain 5377 | CP000521.1 | N/A | 96887253 | 15044 | 6440 | 24 |
| *Actinomyces odontolyticus*, strain 1A.21 | NZ_AAYI02000000 | N/A | 147584210 | 28459 | 5186 | 62 |
| *Bacillus cereus*, strain NRS 248 | NC_003909 | N/A | 38036711 | 5665 | 6714 | 7 |
| *Bacteroides vulgatus*, strain NCTC 11154 | NC_009614 | N/A | 268245610 | 47313 | 5670 | 52 |

TABLE 10-continued

SMRT sequencing details of the Human Microbiome Project Mock Community B sample, which was selectively downsampled so that the species relative abundances follow a log-curve (see FIG. 9 and Examples).

| Species | NCBI reference sequence | # SMRT cells | # sequenced bases | # reads | Avg. read length (bp) | Genome coverage |
|---|---|---|---|---|---|---|
| *Clostridium beijerinckii*, strain NCIMB 8052 | NC_009617 | N/A | 76338075 | 11220 | 6804 | 13 |
| *Deinococcus radiodurans*, strain R1 (smooth) | NC_001263, NC_001264 | N/A | 208383373 | 36878 | 5651 | 68 |
| *Enterococcus faecalls*, strain OG1RF | NC_017316 | N/A | 124121589 | 21448 | 5787 | 45 |
| *Escherichia coli*, strain K12, substrain MG1655 | NC_000913 | N/A | 175026090 | 26997 | 6483 | 38 |
| *Helicobacter pylori*, strain 26695 | NC_000915 | N/A | 138069515 | 19947 | 6922 | 83 |
| *Lactobacillus gasseri*, strain 63 AM | NC_008530 | N/A | 298835744 | 53689 | 5566 | 158 |
| *Listeria monocytogenes*, strain EGDe | NC_003210 | N/A | 676222959 | 122246 | 5532 | 230 |
| *Neisseria meningitides*, strain MC58 | NC_003112 | N/A | 234631294 | 40773 | 5755 | 103 |
| *Propionibacterium acnes*, strain KPA171202 | NC_006085 | N/A | 354143297 | 65801 | 5382 | 138 |
| *Pseudomonas aeruginosa*, strain PAO1-LAC | NC_002516 | N/A | 574069909 | 98693 | 5817 | 92 |
| *Rhodobacter sphaeroides*, strain ATH 2.4.1 | NC_007493, NC_007494 | N/A | 8667736 | 1386 | 6254 | 2 |
| *Staphylococcus aureus*, strain TCH1516 | NC_010079 | N/A | 357417069 | 62396 | 5728 | 124 |
| *Staphylococcus epidermidis*, FDA strain PCI 1200 | NC_004461 | N/A | 455117801 | 81469 | 5586 | 182 |
| *Streptococcus agalactiae*, strain 2603 V/R | NC_004116 | N/A | 67037320 | 10757 | 6232 | 31 |
| *Streptococcus mutans*, strain UA159 | NC_004350 | N/A | 597042303 | 113445 | 5263 | 294 |
| *Streptococcus pneumoniae*, strain TIGR4 | NC_003028 | N/A | 28782378 | 4989 | 5769 | 13 |
| Total | N/A | 49 | 4924660236 | 868615 | 5670 | N/A |

Figure 4A:
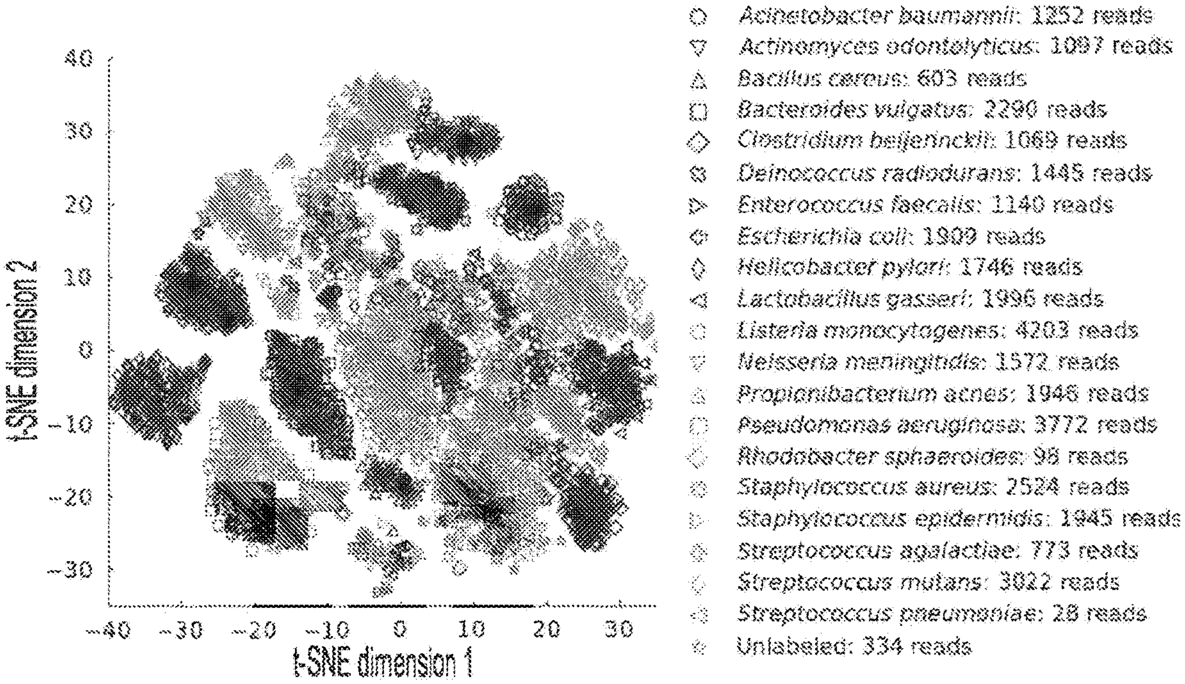
FIGS. 4A-4H depict single molecule read-level binning using composition and DNA methylation profiles.
Figure 4B:
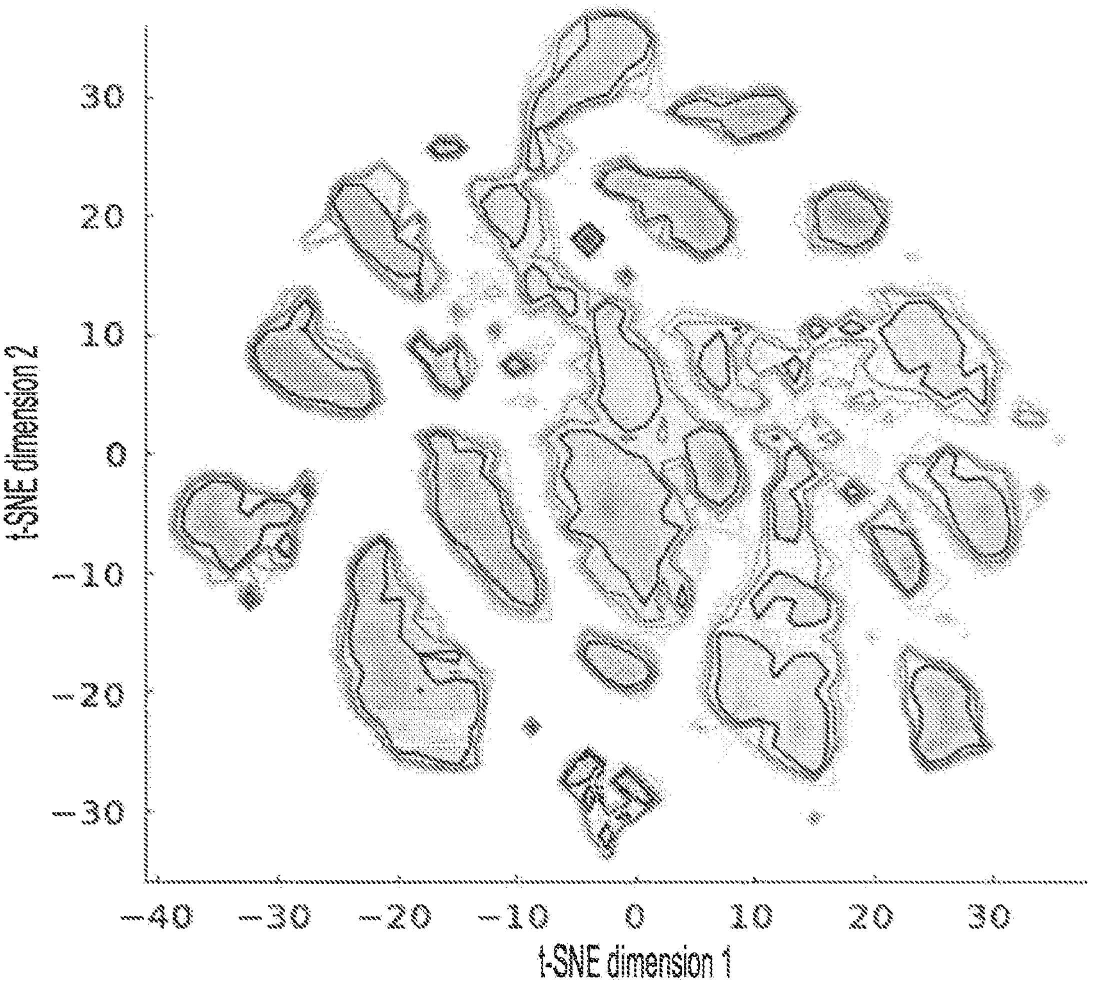
Figure 13:
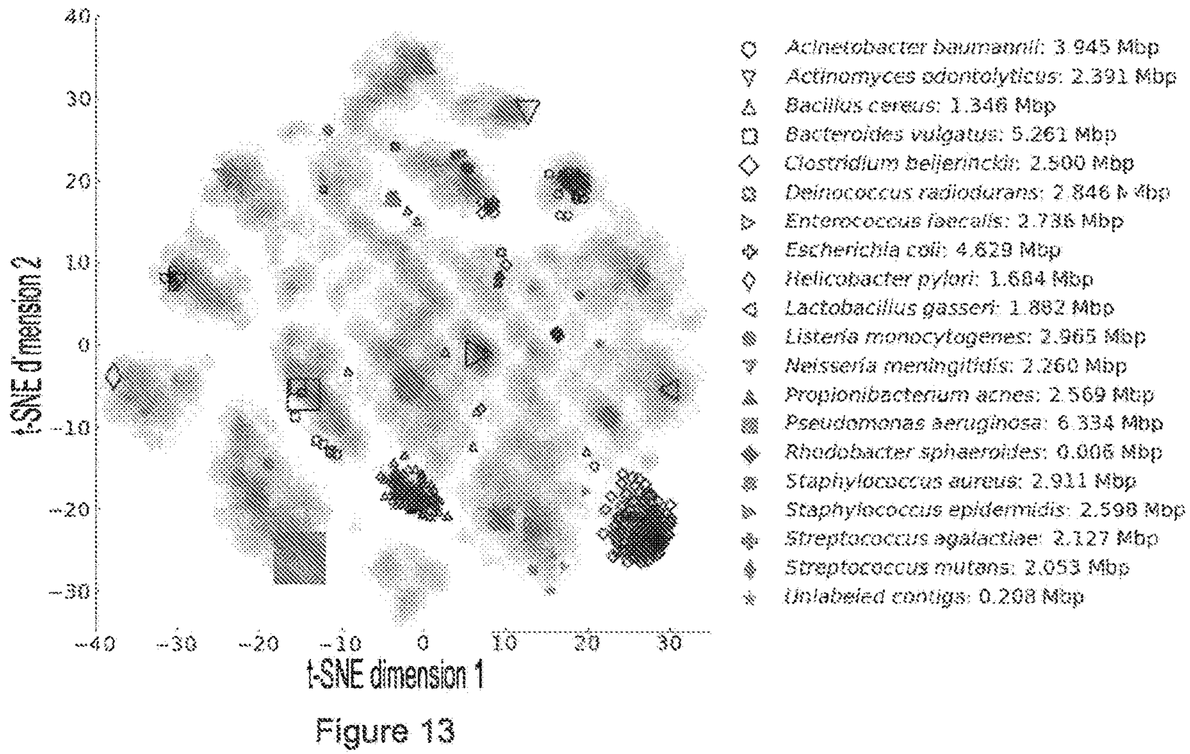
FIG. 13 depicts 5-mer frequency-based binning of assembled contigs and raw reads (length >15 kb) from the log-abundance HMP mock community. Only the contigs are labeled (raw reads represented underneath contigs by density map) and the sum of assembled bases for each Kraken-annotated species is included in the legend.
Figure 14:
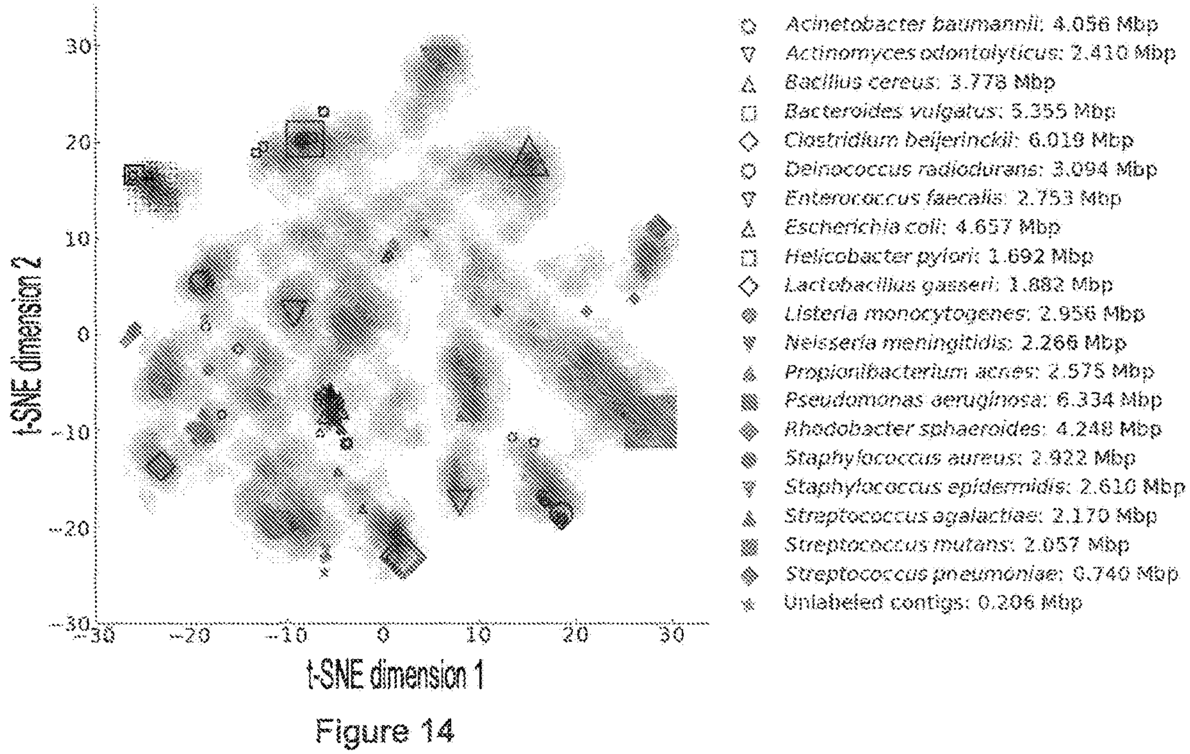
FIG. 14 depicts 5-mer frequency-based binning of assembled contigs and raw reads (length >15 kb) from the even-abundance HMP mock community. Only the contigs are labeled (raw reads represented underneath contigs by density map) and the sum of assembled bases for each Kraken-annotated species is included in the legend.
Figure 15:
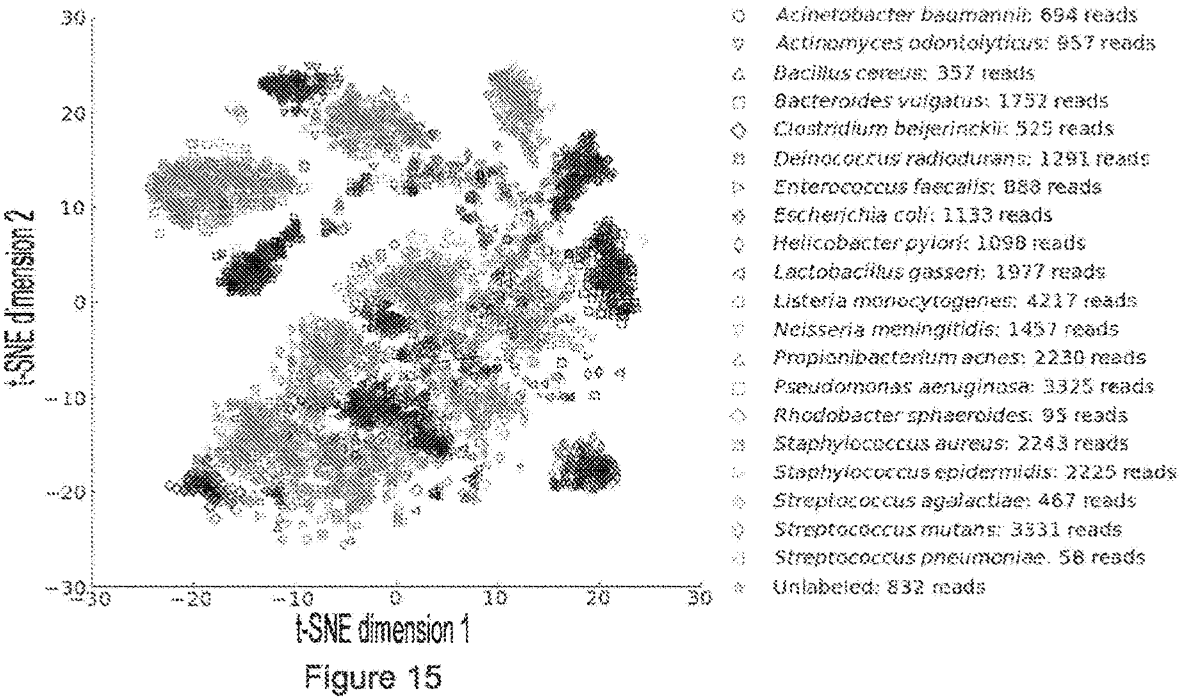
FIG. 15 depicts 5-mer frequency-based binning of unaligned reads (5 kb<length<10 kb) from the log-abundance HMP mock community. The shorter read lengths result in more diffuse and overlapping clusters due to the increased variation in 5-mer frequency metrics on these shorter reads.
Figure 16:
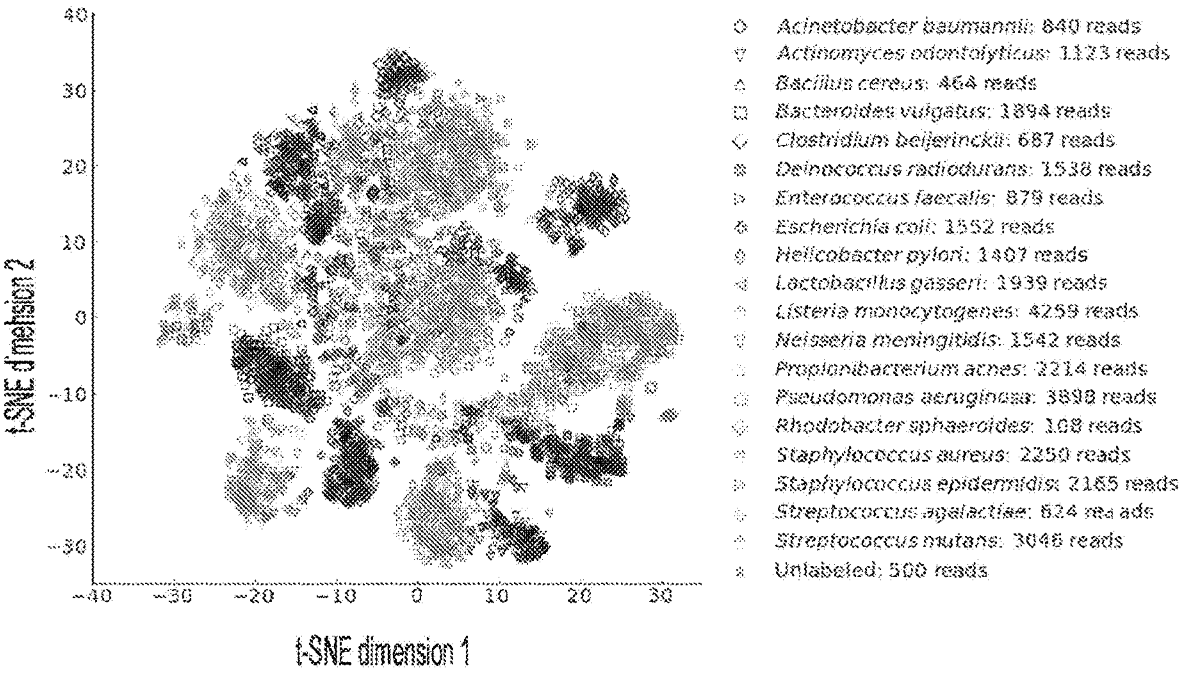
FIG. 16 depicts 5-mer frequency-based binning of unaligned reads (10 kb<length<15 kb) from the log-abundance HMP mock community. The shorter read lengths result in more diffuse and overlapping clusters due to the increased variation in 5-mer frequency metrics on these shorter reads.

5-mer frequency metrics for all HMP mock community sequences (unassembled SMRT reads and assembled contigs) were subjected to t-SNE. In the resulting 2D map, only the contigs were first visualized and annotated using Kraken, revealing a clean separation of contigs from species for which there is a significant number of assembled bases (FIG. 13). To ensure that the contig separation in the 2D map was not biased due to poor assembly results of the low-abundance members of the downsampled community, these findings were confirmed using the even abundance community, finding consistent results (FIG. 14). Next, binning quality of the unassembled SMRT long reads was assessed. Notably, the 5-mer frequency profiles are resilient to the random error in the long reads; the clusters of unassembled reads are highly species-specific. *R. sphaeroides*, while poorly represented in the set of assembled contigs (FIG. 13), is clearly present as a distinct cluster of unassembled reads (FIG. 4A), highlighting the benefit of including unassembled reads in the composition-based binning to reveal the presence of very low-abundance species that are not captured by metagenomic assembly. The additional sequence information in longer reads provides more stable 5-mer frequency profiles and tighter clusters compared to clustering of shorter reads (FIGS. 15 and 16). Furthermore, a 2D histogram provides an overview of global community complexity even absent any sequence annotation (FIG. 4B), making it possible to identify a set of novel sequences from a particular taxon and investigate them further. This analysis highlights the feasibility of direct binning of single molecule long reads even though the raw error rate is high, and the promise of joint binning of unassembled long reads and assembled contigs for more complete representation of a microbiome with low abundance species.

Next, single molecule long reads from third generation sequencing were also binned using their read-level methylation profiles. This can help avoid or resolve chimeric contigs, which occur when multiple strains in a mixture are assembled into contigs built from reads originating from different strains. The significant challenges associated with chimeric contigs affect coverage- and k-mer-based binning methods, hinder strain-specific variant calling and, in the case of single-molecule long-read sequencing, confound the identification of strain-specific methylation on each contig. Importantly, because MTases often transmit across species and strains by HGT, closely related strains with high sequence similarity often encode different MTases that target unique combinations of methylation motifs and provide a novel opportunity to de-convolve co-existing strains in a microbiome sample. A measure of read-level methylation that was developed for the study of epigenetic heterogeneity in single organisms was built on and extended to assess read-level epigenetic heterogeneity in a metagenomic setting (see Examples).

To demonstrate how this can improve multi-strain assemblies, two synthetic mixtures of reads were constructed (see Examples) from (1) two strains of *H. pylori* (Table 11) and (2) three strains of *E. coli* (Table 12).

TABLE 11

SMRT sequencing details of the synthetic mixture of *Helicobacter pylori* strains J99 and 26695.

| Strain | NCBI reference sequence | # SMRT cells | # sequenced bases | # reads | Avg. read length (bp) | Genome coverage |
|---|---|---|---|---|---|---|
| *Helicobacter pylori* 26695 | NC_000915 | 1 | 238512856 | 35093 | 6797 | 150x |
| *Helicobacter pylori* J99 | NC_000921 | 1 | 254757292 | 30043 | 8480 | 150x |

TABLE 12

SMRT sequencing details of the three strains of *E. coli* that were purchased from ATCC.

| *E. coli* strain | # SMRT cells | # sequenced bases | # reads | Avg. read length (bp) | Avg. subread length (bp) | Genome coverage |
|---|---|---|---|---|---|---|
| BAA-2196 O26:H11 | 1 | 1,074,966,617 | 77041 | 13953 | 7266 | 120 |
| BAA-2215 O103:H11 | 1 | 1,013,198,580 | 78201 | 12956 | 6660 | 128 |
| BAA-2440 O111 | 1 | 1,030,411,871 | 78311 | 13157 | 6573 | 146 |

Despite the high sequence similarity of the strains in each mixture (Tables 13 and 14), they encode different MTases that result in different sets of methylated motifs.

TABLE 13

| Average nucleotide identity (ANI) for the two strains of *H. pylori* (str. J99 and 26695). | | | |
|---|---|---|---|
| Organism | NCBI reference sequence | *Helicobacter pylori* str. J99 | *Helicobacter pylori* str. 26695 |
| *Helicobacter pylori* str. J99 | NC_000921 | 1 | |
| *Helicobacter pylori* str. 26695 | NC_000915 | 93.65% | 1 |

TABLE 14

| Average nucleotide identity (ANI) for the three strains of *E. coli*. | | | | |
|---|---|---|---|---|
| Organism | Serotype | BAA-2196 | BAA-2215 | BAA-2440 |
| *Escherichia coli* strain ATCC BAA-2196 | O26:H11 | 1 | | |
| *Escherichia coli* strain ATCC BAA-2215 | O103:H11 | 99.88% | 1 | |
| *Escherichia coli* strain ATCC BAA-440 | O111 | 99.62% | 99.67% | 1 |

Figure 4C:
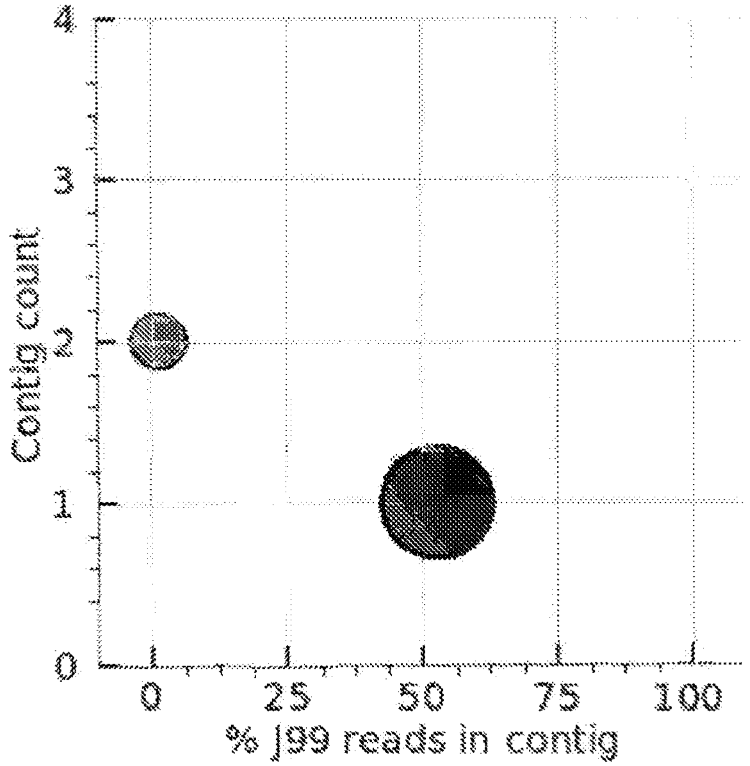

The first mixture contained reads from the *H. pylori* strains J99 and 26695 that assembled together into one small contig from strain 26695 and another large, highly chimeric contig (FIG. 4C). To reduce the chimerism in the assembly, a pre-assembly binning strategy was adopted analogous to that described by Cleary et al., but instead of using k-mer co-abundance for binning reads, single-molecule long reads were separated into bins based on their methylation profiles and subsequently assembled each bin. A small set of four high-density motifs (GATC, GAGG, TGCA, CATG) are sufficient to differentiate these two *H. pylori* strains (Table 15) and were selected to generate methylation profiles for individual single molecule reads.

TABLE 15

| Methylation motifs in the two strains of *H. pylori*. While some motifs are shared between the two strains, many are unique to one or the other strain (highlighted in bold). | | |
|---|---|---|
| Motif | *H. pylori* 26695 | *H. pylori* J99 |
| **GANTC** | No | Yes |
| **GATC** | No | Yes |
| CATG | Yes | Yes |
| **AAGNNNNNCTT** (SEQ ID NO: 24) | No | Yes |
| GAGG | Yes | Yes |
| **GAGHNNNNNCTT** (SEQ ID NO: 25) | No | Yes |
| **CYANNNNNNTGA** (SEQ ID NO: 26) | No | Yes |
| **TCANNNNNNTRG** (SEQ ID NO: 27) | No | Yes |
| **AAGNNNNNCTC** (SEQ ID NO: 28) | No | Yes |
| **GCCTA** | No | Yes |

TABLE 15-continued

| Methylation motifs in the two strains of *H. pylori*. While some motifs are shared between the two strains, many are unique to one or the other strain (highlighted in bold). | | |
|---|---|---|
| Motif | *H. pylori* 26695 | *H. pylori* J99 |
| TCNNGA | Yes | Yes |
| CCGG | Yes | Yes |
| **CCNNGG** | No | Yes |
| **CGBBV** | No | Yes |
| **TCGA** | Yes | No |
| **TGCA** | Yes | No |
| **CRTANNNNNNNTC** (SEQ ID NO: 29) | Yes | No |
| **GANNNNNNNTAYG** (SEQ ID NO: 30) | Yes | No |
| **GGWTGA** | Yes | No |
| **CTRYAG** | Yes | No |
| **CYANNNNNNTTC** (SEQ ID NO: 31) | Yes | No |
| **GAANNNNNNTRG** (SEQ ID NO: 32) | Yes | No |
| **GMRGA** | Yes | No |
| **ATTAAT** | Yes | No |
| **TCTTC** | Yes | No |

Figure 4D:
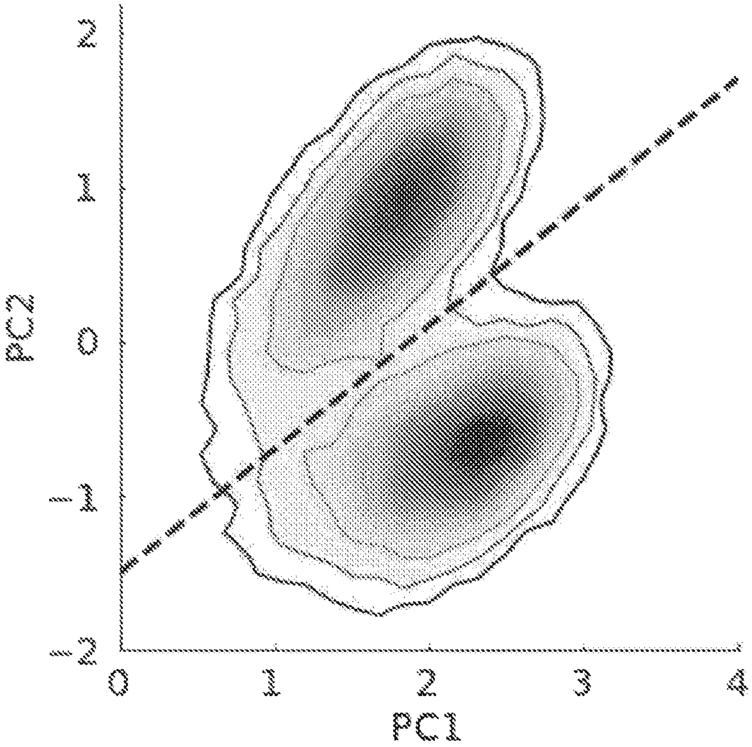
Figure 4E:
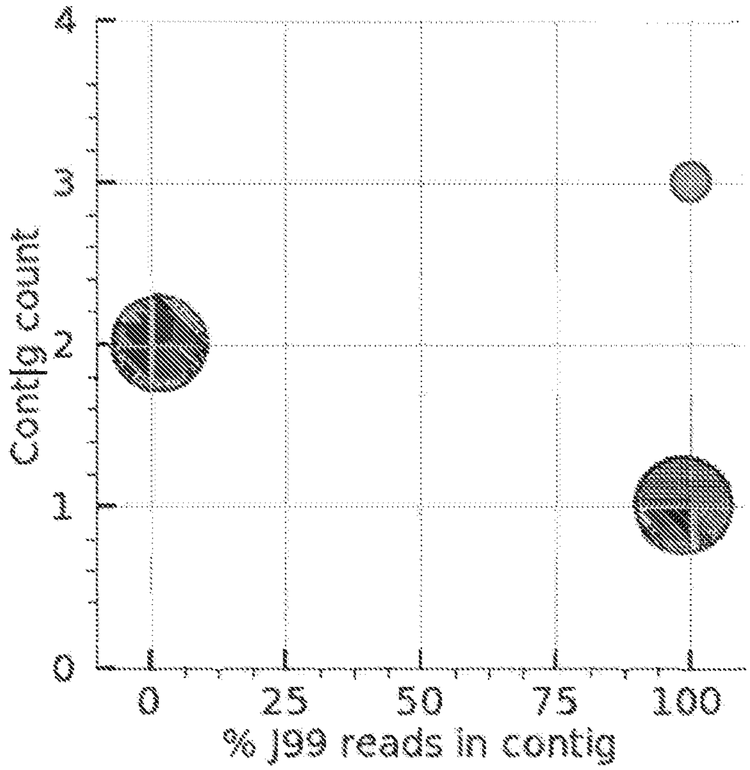
Figure 17:
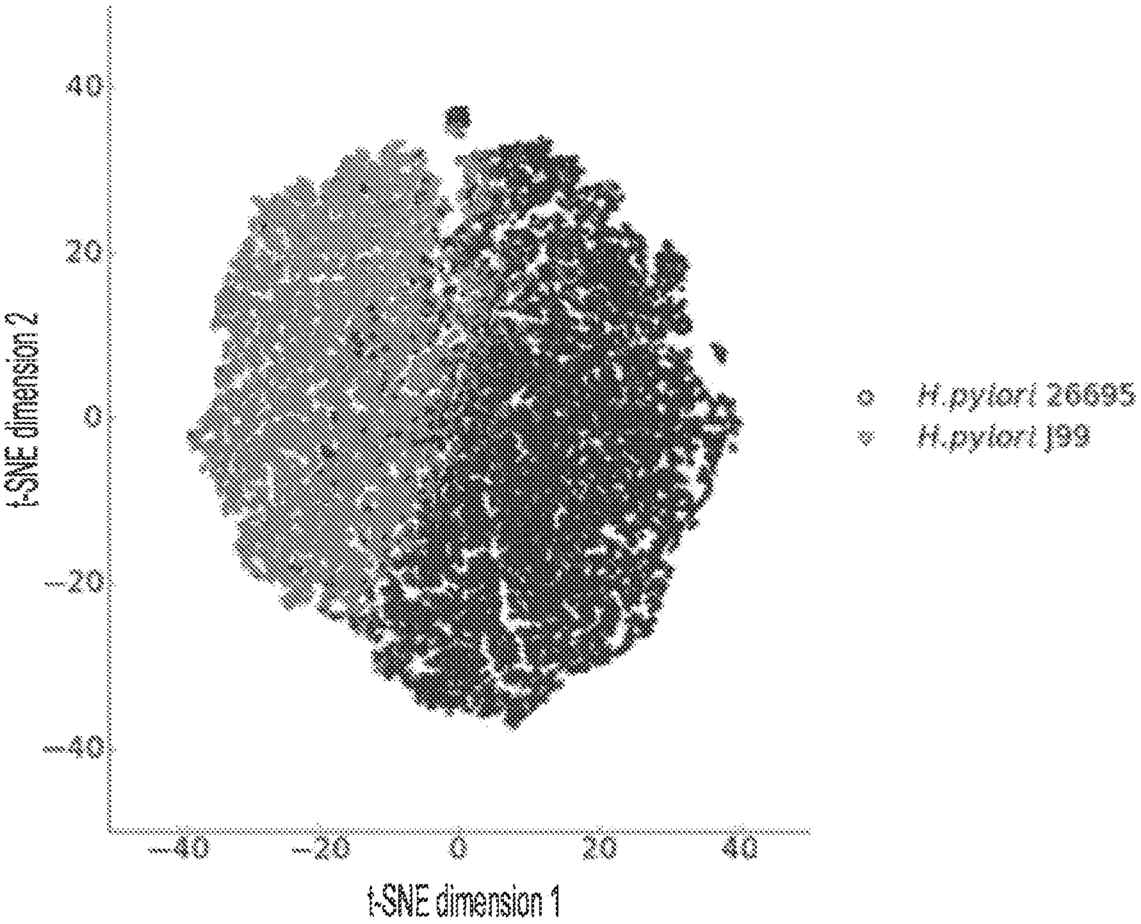
FIG. 17 depicts a 2D map of reads from each of the *H. pylori* strains, 26695 and J99, analyzed in the multi-strain synthetic mixture. 2D map generated using t-SNE, where the only features used in dimensionality reduction are methylation profiles of the reads.

Principal component analysis (PCA) was then used for the dimensionality reduction step to generate a 2D plot of each mixture, revealing a bimodal concentration of reads organized solely by their methylation profiles (FIG. 4D). Dimensionality reduction using t-SNE also revealed two strain-specific clusters, but the resulting clusters did not follow a Gaussian distribution, making delineation of them less straightforward than with PCA (FIG. 17). Because the number of features is small (i.e. four motifs), PCA provides cleaner separation of Gaussian subpopulations in this application than does t-SNE; this also suggests that different dimensionality reduction methods may complement each other in different applications. Finally, the epigenetically binned reads were assembled separately using HGAP3 with the same parameters used for the mixed assembly, resulting in separately assembled contigs with improved contiguity, including chromosome-scale contigs for both strains, and minimal chimerism (FIG. 4E).

Figure 4F:
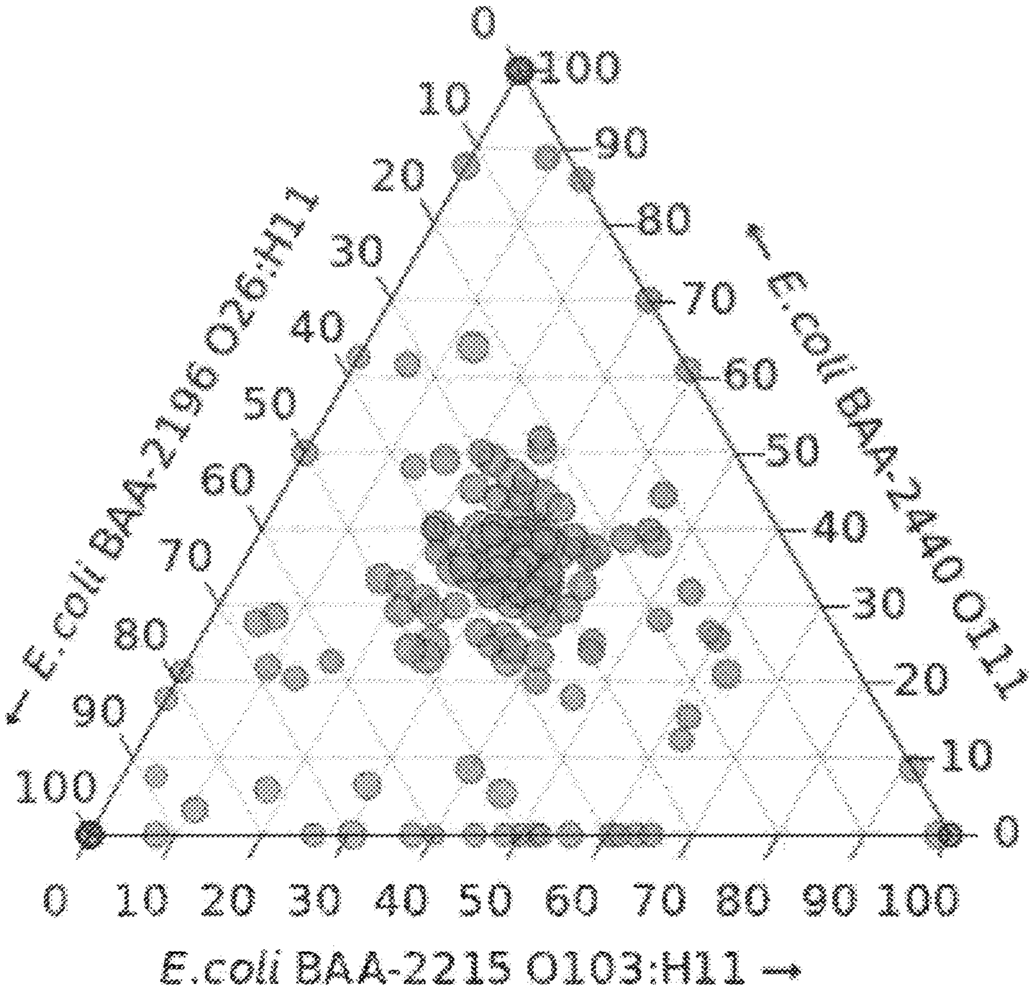

The read-level methylation binning procedure was next applied to another data set consisting of SMRT reads from three strains of *E. coli* from distinct serotypes: O26:H11, O103:H11, and O111 (see Examples). An assembly of these mixed reads results in many highly chimeric contigs and very few contigs that are specific to a strain (FIG. 4F). The motifs that differentiate these strains, AGCACY, CRARCAG, GGTNACC, and CTGCAG, are longer (Table 16), which are more likely to be disrupted by the random nature of the sequencing errors in unaligned single molecule long reads, causing incorrect IPD values for each long motif.

TABLE 16

Methylation motifs in the three strains of *E. coli* that were used to construct read-level methylation profiles.

| Motif | *E. coli* BAA-2196 O26:H11 | *E. coli* BAA-2215 O103:H11 | *E. coli* BAA-2440 O111 |
|---|---|---|---|
| **AGCACY** | No | Yes | No |
| **CRARCAG** | No | No | Yes |
| **GGTNACC** | No | No | Yes |
| **CTGCAG** | Yes | No | No |
| **GATC** | Yes | Yes | Yes |
| **TACNNNNNNNRTRTC** (SEQ ID NO: 33) | Yes | Yes | No |
| **GAYAYNNNNNNNGTA** (SEQ ID NO: 34) | Yes | Yes | No |

Figure 4G:
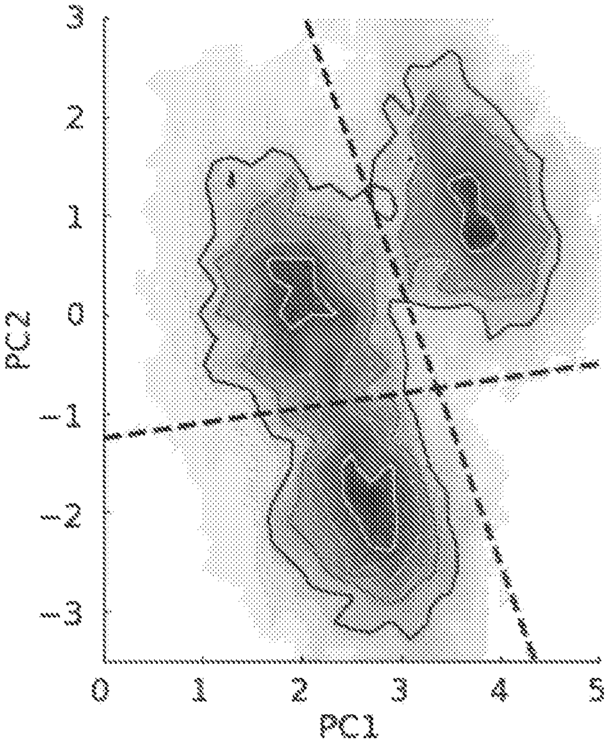
Figure 4H:
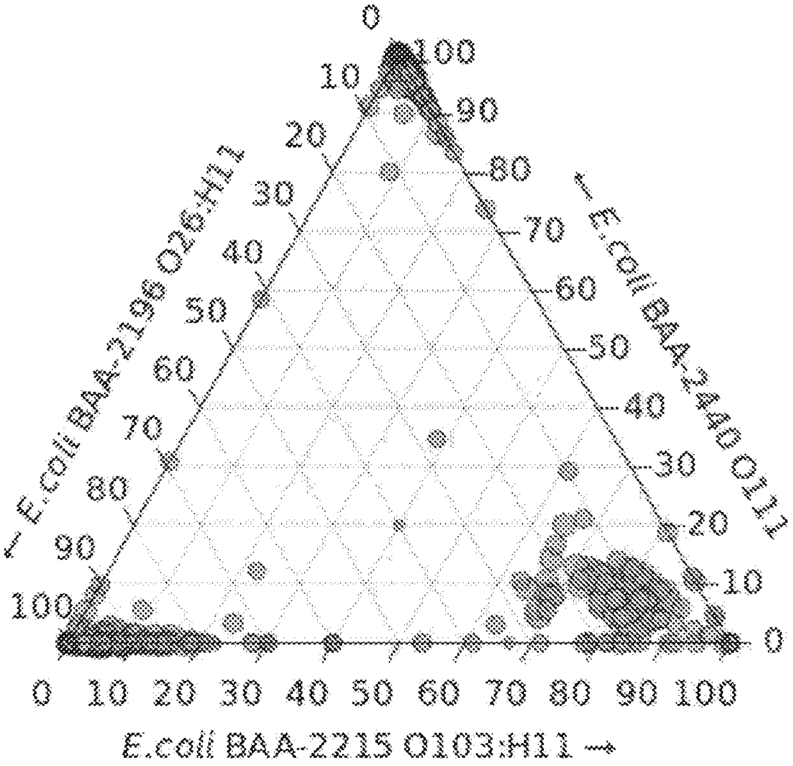

Addressing this required an additional alignment step to error correct the reads prior to calculating the scores for the methylation profiles. Specifically, the reads from each strain were aligned to the standard *E. coli* K12 MG1655 reference sequence (RefSeq accession NC_000913.3) then calculated read-level methylation scores for each motif. Methylation profiles were again visualized using PCA and reads were binned based on visible subpopulations (FIG. 4G). Finally, isolated assembly of reads from each bin resulted in a substantial reduction of contig chimerism and an increase in contigs containing sequence specific to each *E. coli* strain (FIG. 4H).

Comparison with Metagenomic Sequencing Using Synthetic Long Reads

Recent advances in library preparation protocols for Illumina sequencing have made it possible to generate synthetic long reads of several kilobases in length. The read lengths of synthetic long reads can approach those generated by SMRT sequencing, yet important differences between the technologies have implications for their specific applications in metagenomics and therefore warrant a detailed investigation. Because the capability to infer methylation events is a unique strength of SMRT sequencing as studied above, other aspects of the two techniques and their potential complementarity are emphasized here.

The read lengths and high accuracy of synthetic reads have enabled researchers to phase substrain-level bacterial haplotypes in metagenomic samples. By aligning synthetic long reads to contigs generated through de novo metagenomic assembly, the study revealed the presence of multiple genotypes within the same strain. A prerequisite for substrain haplotyping with synthetic long reads is a metagenomic assembly that serves as a reference for the read alignment. Kuleshov et al. acknowledge that SMRT reads are more likely to result in large draft assemblies, and indeed point out that contigs assembled from SMRT reads are significantly larger than those assembled using synthetic long reads, even when the latter was supplemented by traditional short reads.

Given the multi-kb read lengths and high accuracy of synthetic long reads, it was sought to understand why they resulted in more fragmented and less comprehensive assemblies than did SMRT reads. To this end, both the synthetic long reads sequenced from the 20-member HMP Mock Community B (staggered abundance; HM-277D) and the SMRT reads from the same community were aligned to their reference genomes. Because the SMRT reads were sequenced from a different version of the HMP Mock Community B (even abundance; HM-276D), the aligned reads were downsampled so that total numbers of aligned bases for each organism were roughly equal for both sequencing technologies (see Examples; Table 10, above).

Figure 5A:
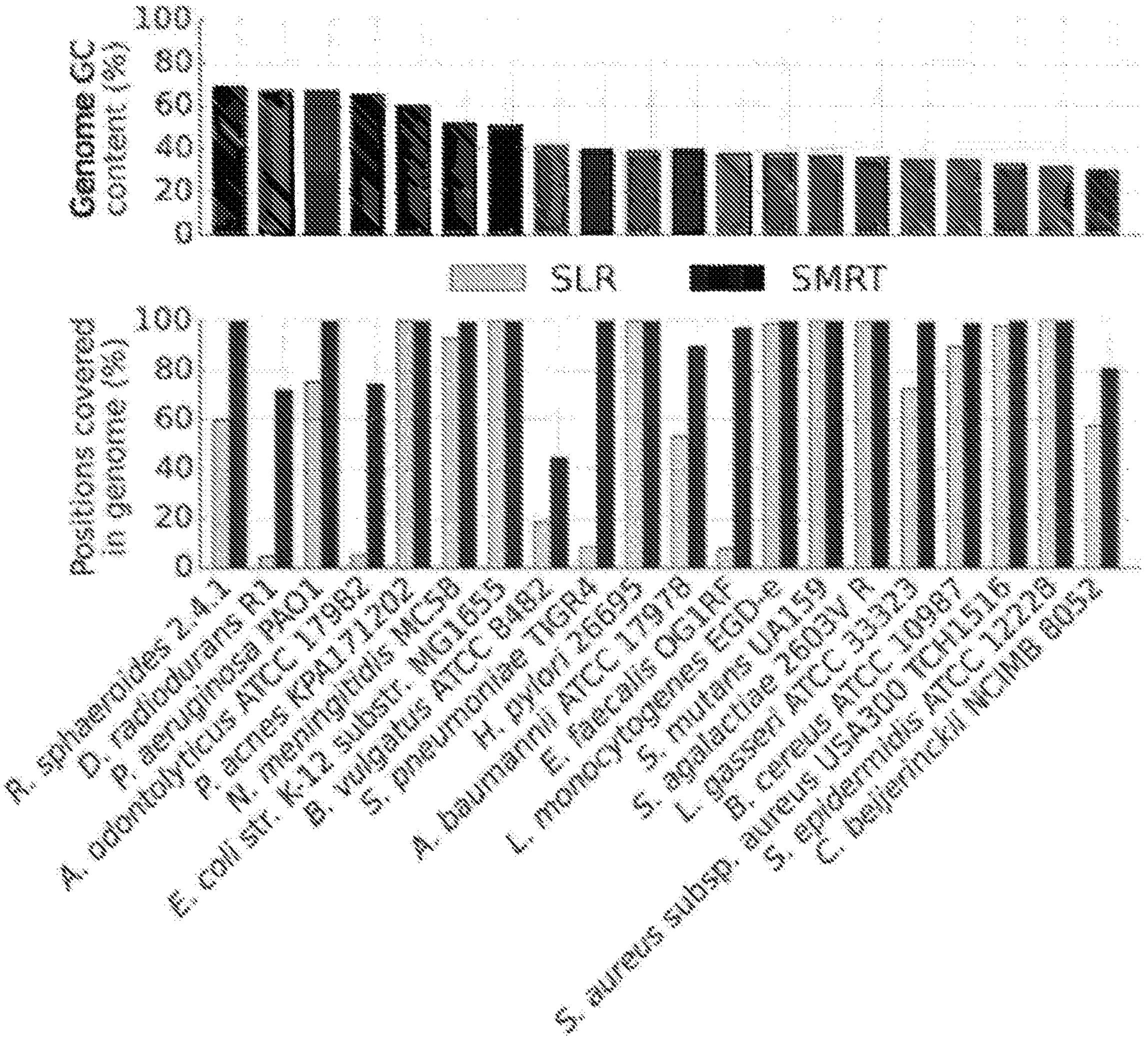
FIGS. 5A-5D depicts a comparison between synthetic long reads and SMRT long reads.

Despite considering approximately the same number of aligned bases for each technology, SMRT reads covered a higher percentage of genome positions in 17 of the 20 species and matched the percentage of genome positions covered by synthetic long reads in the remaining three species (FIG. 5A; Table 17).

TABLE 17

Summary of the reference alignments used to compare synthetic long read (SLR) and SMRT sequencing of the Human Microbiome Project Mock Community B. For comparison purposes, downsampling of alignments was done to make the total number of aligned bases approximately equal for both SLR and SMRT reads (see Examples).

| Species | NCBI reference sequence | SLR aligned bases | SMRT aligned bases | SLR (% genome covered) | SMRT (% genome covered) |
|---|---|---|---|---|---|
| *Acinetobacter baumannii*, strain 5377 | CP000521.1 | 10894845 | 10248371* | 53.08 | 89.73 |
| *Actinomyces odontolyticus*, strain 1A.21 | NZ_AAYI02000000 | 3730113 | 3724483* | 5.19 | 74.36 |

TABLE 17-continued

Summary of the reference alignments used to compare synthetic long read (SLR) and SMRT sequencing of the Human Microbiome Project Mock Community B. For comparison purposes, downsampling of alignments was done to make the total number of aligned bases approximately equal for both SLR and SMRT reads (see Examples).

| Species | NCBI reference sequence | SLR aligned bases | SMRT aligned bases | SLR (% genome covered) | SMRT (% genome covered) |
|---|---|---|---|---|---|
| *Bacillus cereus*, strain NRS 248 | NC_003909 | 26483461 | 26892969* | 89.47 | 98.82 |
| *Bacteroides vulgatus*, strain NCTC 11154 | NC_009614 | 3579005 | 3526600* | 18.72 | 44.76 |
| *Clostridium beijerinckii*, strain NCIMB 8052 | NC_009617 | 11135316 | 11234921* | 57.73 | 80.62 |
| *Deinococcus radiodurans*, strain R1 (smooth) | NC_001263, NC_001264 | 3983663 | 3901421* | 4.70 | 71.83 |
| *Enterococcus faecalis*, strain OG1RF | NC_017316 | 11270120 | 11718812* | 7.60 | 97.25 |
| *Escherichia coli*, strain K12, substrain MG1655 | NC_000913 | 608247402* | 607875898 | 99.93 | 100.00 |
| *Helicobacter pylori*, strain 26695 | NC_000915 | 26015813 | 25668905* | 99.81 | 99.81 |
| *Lactobacillus gasseri*, strain 63 AM | NC_008530 | 10760149 | 10435924* | 72.62 | 99.10 |
| *Listeria monocytogenes*, strain EGDe | NC_003210 | 24364014 | 24505316* | 98.75 | 99.92 |
| *Neisseria meningitides*, strain MC58 | NC_003112 | 15910092 | 16261924* | 92.98 | 99.11 |
| *Propionibacterium acnes*, strain KPA171202 | NC_006085 | 26717866 | 27116796* | 99.82 | 100.00 |
| *Pseudomonas aeruginosa*, strain PAO1-LAC | NC_002516 | 170029436 | 170933335* | 75.15 | 100.00 |
| *Rhodobacter sphaeroides*, strain ATH 2.4.1 | NC_007493, NC_007494 | 29901273 | 29525967* | 59.99 | 99.78 |
| *Staphylococcus aureus*, strain TCH1516 | NC_010079 | 61148568 | 61210521* | 97.92 | 100.00 |
| *Staphylococcus epidermidis*, FDA strain PCI 1200 | NC_004461 | 173408151 | 173659048* | 100.00 | 100.00 |
| *Streptococcus agalactiae*, strain 2603 V/R | NC_004116 | 49104157 | 49483720* | 99.37 | 100.00 |
| *Streptococcus mutans*, strain UA159 | NC_004350 | 252711874 | 252259023* | 100.00 | 100.00 |
| *Streptococcus pneumoniae*, strain TIGR4 | NC_003028 | 23107608 | 22947284* | 8.45 | 99.90 |

*Number of total aligned bases reached by downsampling alignments (see Examples)

In several cases, the increases in genome coverage over synthetic long reads were dramatic: SMRT sequencing of *D. radiodurans, A. odontolyticus, E. faecalis*, and *S. pneumoniae* covered an additional 67.1%, 69.2%, 90.0%, and 91.2% of their genomes, respectively. The genomes with the highest GC-content (*R. sphaeroides,* 68.8% GC; *D. radiodurans,* 66.6% GC; *P. aeruginosa,* 66.6% GC; *A. odontolyticus,* 65.4% GC) were among those that saw significant increases in genome coverage with SMRT reads compared to synthetic long reads (Table 17). This observation is consistent with previous studies showing that the PCR amplification of DNA fragments required for synthetic long read sequencing is sensitive to genomic GC-content and can result in significant coverage biases (i.e. highly non-uniform sequence coverage).

Figure 5B:
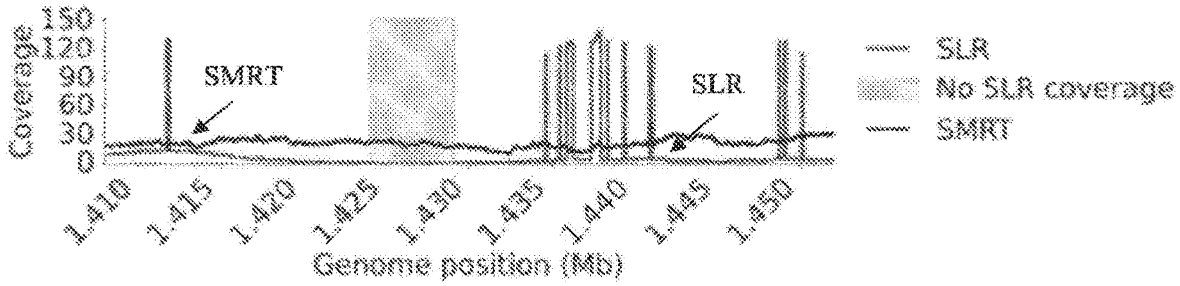
Figure 5C:
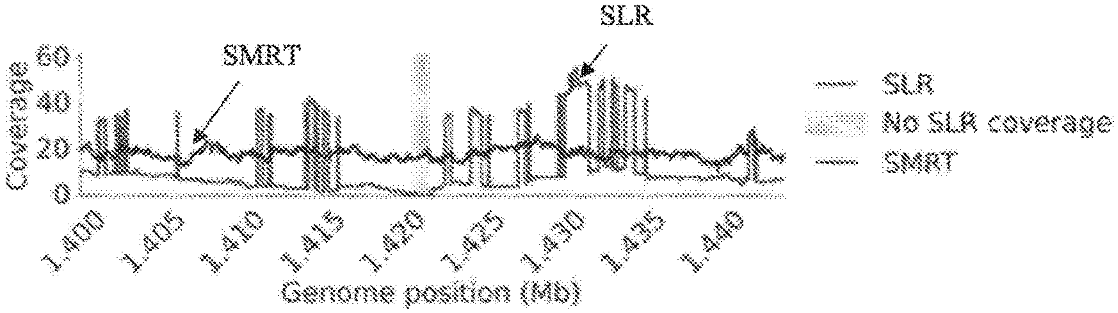
Figure 5D:
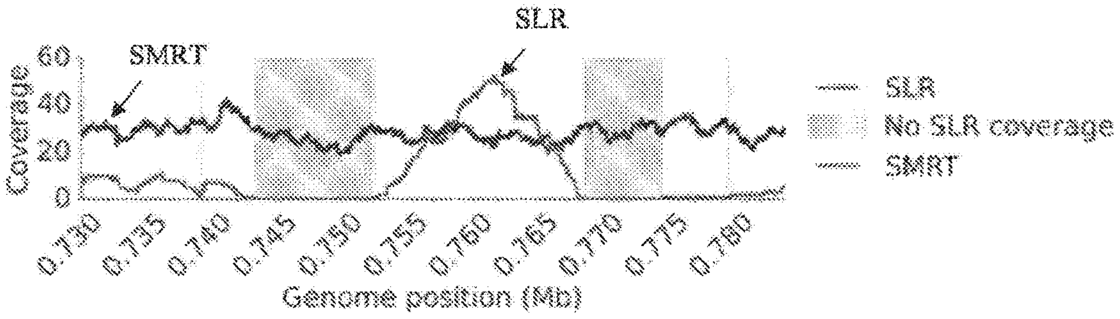
Figure 18:
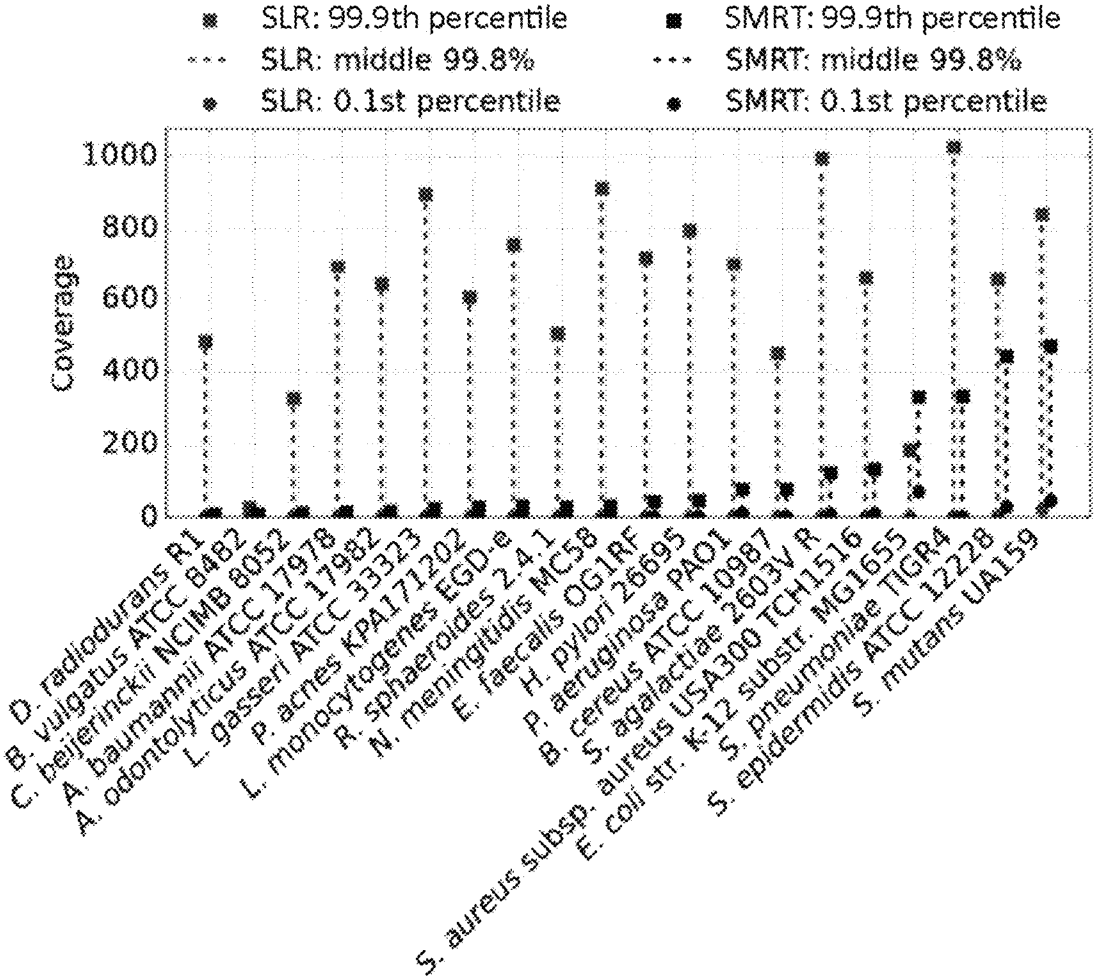
FIG. 18 depicts coverage variation for alignments of abundance-matched SLR and SMRT reads. A significant number of bases in SLRs are aligned in the same regions, creating dramatic peaks in coverage. SMRT reads largely lack these peaks and have a more uniform coverage profile.
Figure 19:
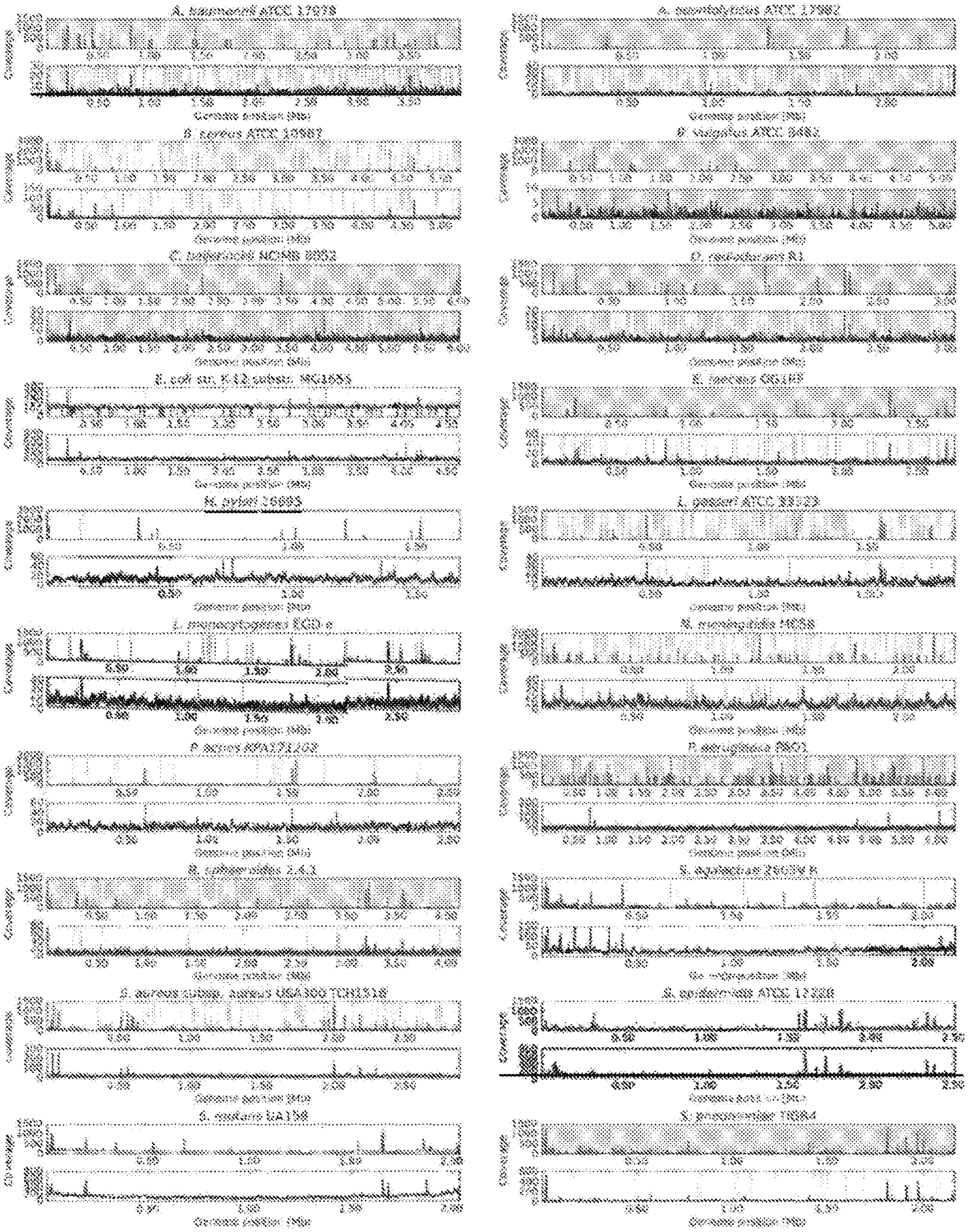
FIG. 19 depicts genome-wide coverage of abundance-matched synthetic long reads (red lines) and SMRT reads. Regions with zero coverage are highlighted for synthetic long reads and SMRT reads.

SMRT sequencing, however, is an amplification-free protocol and is not subject to GC bias, resulting in more uniform coverage profiles across genomes (FIG. 18). Further illustrating this phenomenon are three small regions from the genomes of *S. agalactiae, S. aureus*, and *P. aeruginosa* (FIG. 5B-5D), which are representative of many of the genomes in the mock community (FIG. 19). The synthetic long reads coverage profiles consist of peaks and valleys, representing over- and under-amplified DNA fragments, respectively.

Some of the valleys result in complete coverage dropouts, across which genome assembly becomes impossible. The SMRT sequencing protocol, on the other hand, results in much more uniform coverage profiles and fewer coverage dropouts, making it more amenable to metagenomic assembly and more likely to result in chromosome-scale contigs.

Two additional sources of systematic error in the synthetic long reads, resulting from dilution and sub-assembly steps in the protocol, make it more difficult to assemble high abundance species and regions containing tandem repeats. These steps are unique to synthetic long reads and do not apply to SMRT sequencing, which might further contribute to the superiority of SMRT reads for generating large metagenomic assemblies. The strengths of synthetic long reads, however, lie in their ability to call (and phase) local genomic features, such as single nucleotide variants (SNVs) or short insertions and deletions. Overall, this suggests a complementary strategy for maximizing assembly quality with SMRT sequencing and leveraging synthetic long reads for variant calling and haplotyping.

Methylation binning of contigs alone may, in some instances, to be challenging for organisms that are present at low-abundance in high-complexity samples, as it is difficult to detect methylated motifs from the small contigs that are typically assembled from low-abundance organisms. However, this can be complemented by binning assignments from cross-coverage and composition-based binning tools, such as CONCOCT, because contigs can be phased together according to third-party binning assignments to aid the discovery of methylated motifs, as was demonstrated with the mouse gut microbiome analysis. De novo methylation motif detection is well powered at the levels of contigs or bins, but is challenging at the level of single reads due to the requirement for long read length, especially for large, sparsely distributed motifs. However, read-level binning by methylation profiles can build on a priori knowledge of the methylation motifs in a species of interest for the deconvolution of multiple co-existing strains, as illustrated in this study. Continued increases in read length of third-generation sequencing also raise the prospect of more reliable de novo detection of methylated motifs at the single read-level in the near future.

The choice of SMRT sequencing libraries of long insert size can improve contiguity in a metagenomic assembly, but the size selection procedure may filter out short MGEs like plasmids and phages. The choice of library size would depend on goals specific to the particular research study. When resource allows, combinations of long and short libraries can be integrated to achieve both good assembly contiguity and the good coverage of short MGEs, although challenges currently exist in assembling complex MGEs from shorter reads. Integrating additional sequence data from a rolling circle amplification library might help to highlight plasmids that are excluded from the standard SMRT library or do not fully circularize in the SMRT assembly.

Although the long reads and methylation profiles made possible by SMRT sequencing (and other third-generation sequencing technologies) hold great promise for studying microbial communities, they currently require more input DNA than second generation sequencing technologies. However, this requirement has decreased recently as the SMRT technology has matured and further reductions are anticipated in the future, given the active development and pace of technological improvement.

EXAMPLES

The following examples illustrate specific aspects of the instant description. The examples should not be construed as limiting, as the examples merely provide specific understanding and practice of the embodiments and their various aspects.

Using metagenomic sequencing data from several synthetic and real microbiome samples, comprehensive evaluations of the proposed approach were performed and it was demonstrated that DNA methylation is a novel and rich feature that provides significant discriminative power capable of complementing existing methods for high-resolution metagenomic binning.

Code availability. The software supporting all proposed methods is implemented in Python and is available with full documentation on the GitHub website.

Example 1: Integrating Methylation and Composition to Bin Contigs by Strains Epigenetic information was used to segregate contigs assembled from highly similar strains that would be otherwise indistinguishable using k-mer frequency-based methods. Two sets of infant gut microbiota obtained from stool samples of children who were selected for sequencing based on a high genetic risk for development of T1D were examined.

Interestingly, it has been observed that the particular species of *Bacteroides* that dominates the composition of both samples, *Bacteroides* dorei, often spikes in relative abundance prior to onset of T1D in children, making it an important species to understand and potentially monitor during early adolescence. 16S sequencing showed that the two samples contained two distinct strains of *B. dorei*: Sample A consisted of 63.7% *B. dorei* str. 105 (CP007619), while Sample B contained 47.9% *B. dorei* str. 439 (CP008741). Despite a high sequence similarity between the two *B. dorei* strains (Table 18), each strain has a unique set of methylated sequence motifs and therefore a unique methylation profile.

TABLE 18

Average nucleotide identity (ANI) for the two strains of *Bacteroides dorei* found in the infant gut microbiome samples A (str. 105) and B (str. 439).

| Organism | NCBI reference sequence | *Bacteroides dorei* str. 105 | *Bacteroides dorei* str. 439 |
|---|---|---|---|
| *Bacteroides dorei* str. 105 | CP007619 | 1 | |
| *Bacteroides dorei* str. 439 | CP008741 | 99.43% | 1 |

SMRT sequencing data were collected for the two microbiome samples from a previous study (Table 19) and performed a metagenomic de novo assembly using a combination of both gut samples to generate a mixture of contigs from both *B. dorei* strains in the output set of metagenomic contigs. Lacking any labeling for these contigs, the sequence annotation tool Kraken was applied for labeling of all non-*B. dorei* contigs and an alignment-based labeling approach for distinguishing the two *B. dorei* strains (See Examples).

TABLE 19

SMRT sequencing details of two infant gut microbiome samples.

| Sample | # SMRT cells | # sequenced bases | # reads | Avg. read length (bp) |
|---|---|---|---|---|
| A | 10 | 2600873639 | 434396 | 5987 |
| B | 13 | 2984063756 | 472788 | 6312 |
| A + B | 23 | 5584937395 | 907184 | 6156 |

Figure 20:
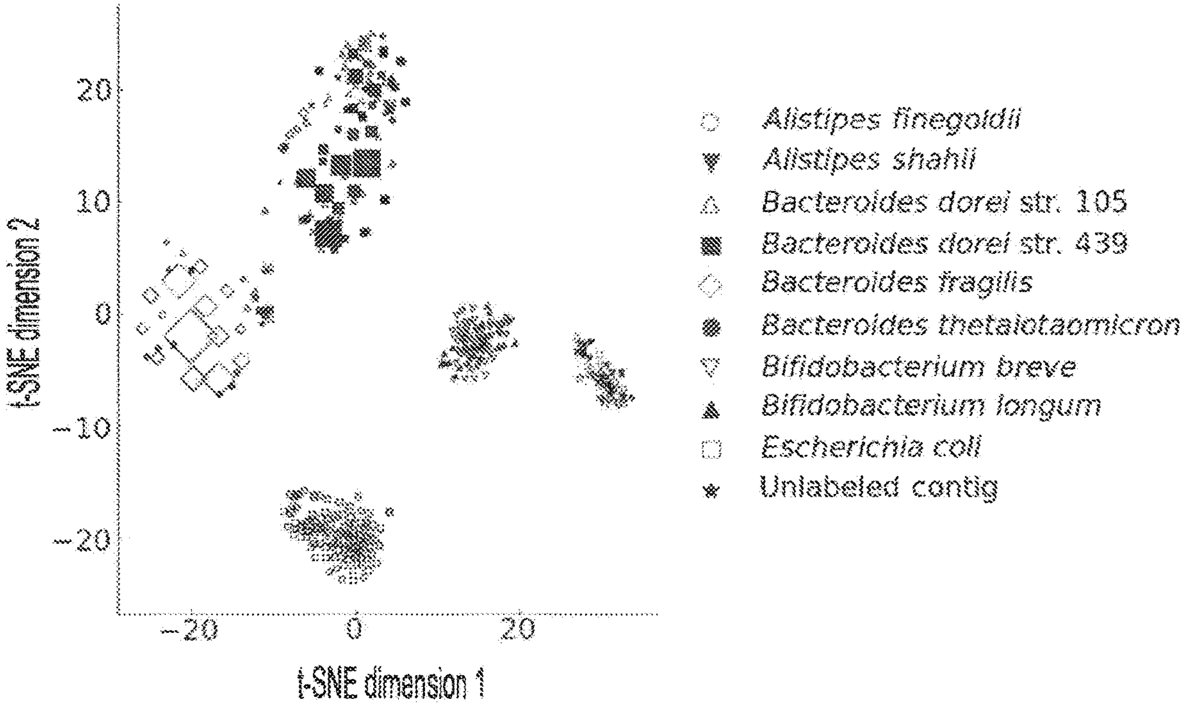
FIG. 20 depicts 5-mer frequency-based binning of contigs assembled from a mixture of two infant microbiome samples. Several clusters contain a mixture of species from the same genus. Kraken-based annotation relies on an existing reference database and is therefore incomplete; contigs not generating a database hit are marked Unlabeled.

Composition-based binning was first conducted using 5-mer frequency profiles, followed by t-SNE dimensionality reduction (FIG. 20). The map has five distinct clusters of contigs, four of which consist primarily of a combination of contigs from multiple species or strains. This suggests that composition-based binning is insufficient to segregate the two strains of *B. dorei* due to their high sequence similarity. Notably, composition-based binning also fails to segregate *Bacteroides fragilis* from *Bacteroides thetaiotaomicron, Bifidobacterium breve* from *Bifidobacterium longum*, and *Alistipes finegoldii* from *Alistipes shahii.*

Figure 21:
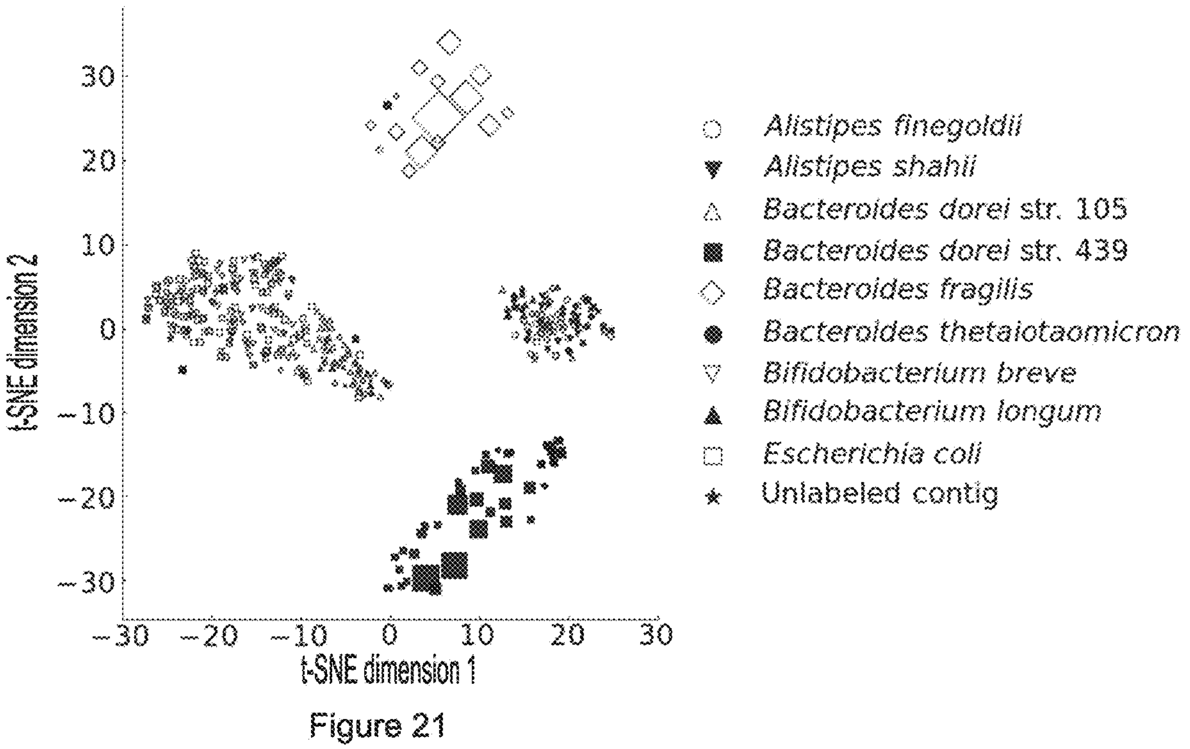
FIG. 21 depicts t-SNE map of infant gut microbiome (combination of samples A and B) assembled contigs. Methylation scores for motifs (selected from the motif filtering method) were the only feature used for dimensionality reduction. Kraken-based annotation relies on an existing reference database and is therefore incomplete; contigs not generating a database hit are marked Unlabeled.
Figure 22:
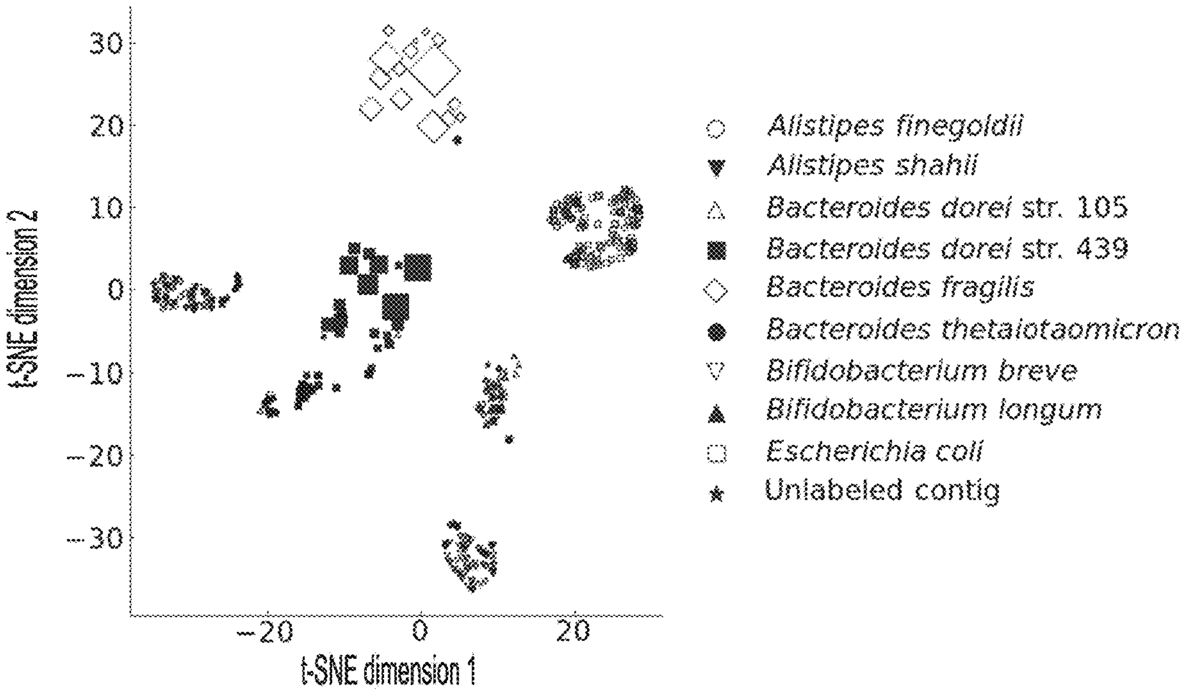
FIG. 22 depicts t-SNE map of infant gut microbiome (combination of samples A and B) assembled contigs binned by both 5-mer frequency and methylation profiles, which resolve the contigs into mostly species-specific clusters. Kraken-based annotation relies on an existing reference database and is therefore incomplete; contigs not generating a database hit are marked Unlabeled.

Motif filtering identified seven motifs with significant methylation scores on at least one contig in the assembly: GG$\underline{\text{A}}$TCA, G$\vec{\text{A}}$TCA, TTCGA$\vec{\text{A}}$, G$\vec{\text{A}}$TC, CTC$\vec{\text{A}}$T, GA$\vec{\text{A}}$TC, and GG$\vec{\text{A}}$TC. The resulting t-SNE map constructed using methylation profiles alone (FIG. 21) resolves the contigs into four clusters. In contrast to the k-mer frequency-based map and as a consequence of their unique methylation profiles, the two strains of *B. dorei* are very well segregated in the methylation-based binning analysis. However, methylation-based binning alone did not fully segregate all other species due to an insufficient diversity of methylated motifs among them. This suggests that both methylation-based and composition-based binning methods can complement each other to compensate for the shortcomings of each approach. By combining k-mer frequency and methylation profiles, both reduced separately by t-SNE to 2D, into a single matrix with four columns, t-SNE was again used to reduce the matrix and generate a 2D scatter plot (FIG. 22). This approach succeeds in separating the two strains of *B. dorei* from each other, *B. fragilis* from *B. thetaiotaomicron*, and *B. breve* from *B. longum*. Only the two species from the *Alistipes* genus remain convoluted in the combined map, due to high sequence similarity and likely identical methylomes. Again using a silhouette coefficient to assess the contig clustering, it was found that while composition-based binning alone results in a silhouette coefficient of 0.03, the integration with methylation-based binning increases the coefficient to 0.41, demonstrating that contig methylation profile can help deconvolute contigs with high sequence similarity.

Example 2: Methylome Analysis of Virulent *Klebsiella pneumoniae* Strain

To assess the methylome diversity across strains of a clinically relevant bacterial species, the 878 bacterial strains in the REBASE database for which methylated motifs have been identified through SMRT sequencing were analyzed. Among these was a virulent and antibiotic-resistant strain of *Klebsiella pneumoniae* (strain 234-12) isolated from a patient during a 2011 outbreak in Germany. A single 362 kb plasmid (pKpn23412-362) hosted by this strain contained thirteen antibiotic-resistance genes, including the bla (TX-M-15 (Kpn23412_5431) gene responsible for conferring the extended spectrum β-lactamase (ESBL) phenotype of the bacteria. The plasmid also contained multiple replicons, which helps to expand the range of organisms in which the plasmid can successfully replicate.

Figure 23:
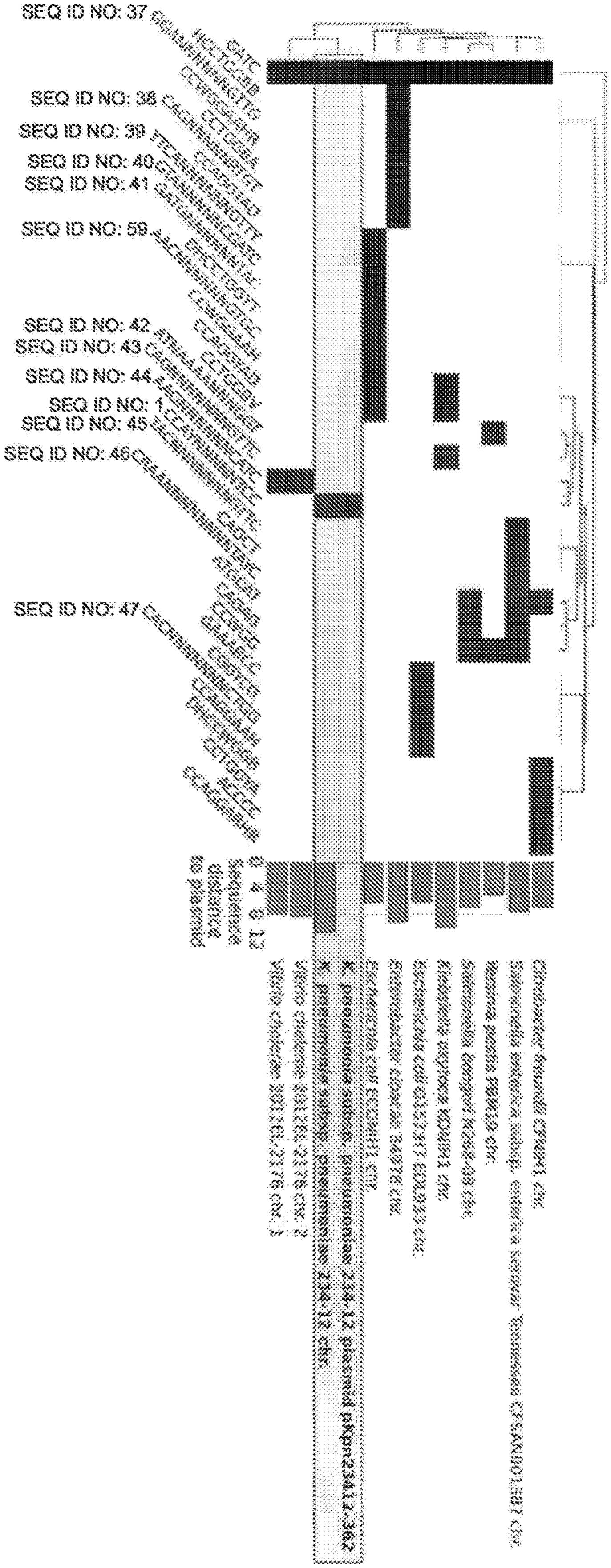
FIG. 23 depicts a heatmap showing hierarchical clustering of all known methylated motifs in REBASE for *K. pneumoniae* strain 234-12 and nine other species whose chromosomes have smaller sequence distance to the *K. pneumonia* strain 234-12 plasmid (horizontal bars) than its own host chromosome.
Figure 24:
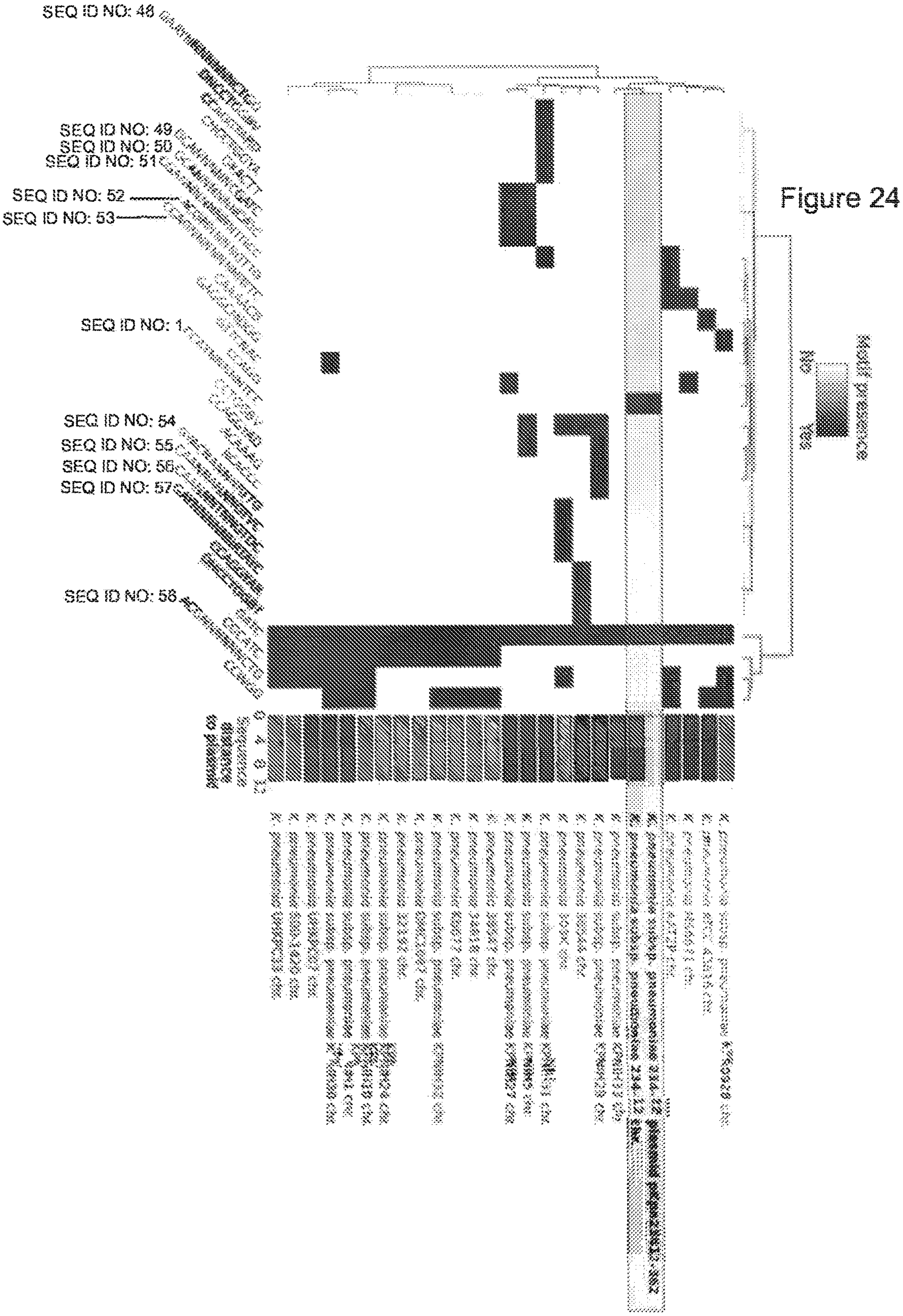
FIG. 24 depicts Heatmap showing hierarchical clustering of all motifs in REBASE for 25 strains of *K. pneumoniae*. The strains contain 17 unique methylation motifs, including CCAYNNNNNTCC (SEQ ID NO: 1) that is observed solely in *K. pneumoniae* strain 234-12.

The sequence composition profiles of this plasmid and the *K. pneumoniae* chromosome differed to an extent (Euclidian distance, d=10.6) that would prohibit any sequence-based mapping of plasmid to host in a metagenomic sample. However, the methylated motifs, including GATC and CCAYNNNNNTCC (SEQ ID NO: 1), present an opportunity for linking the plasmid and host epigenetically. To demonstrate this, the methylated motifs of nine other species contained in the REBASE database were examined, all of which had chromosome sequence composition profiles closer to *K. pneumoniae* plasmid pKpn23412-362 (d<10.6) than did the true host chromosome. Although some of the composition profiles are relatively similar to the plasmid, the methylation profiles are diverse, making it possible to match plasmid pKpn23412-362 to its *K. pneumoniae* host (FIG. 23). Finally, all 25 strains of *K. pneumoniae* contained in the Rebase database were examined, and it was found that the sequence of plasmid pKpn23412-362 was roughly the same Euclidian distance from the chromosomes of each strain (FIG. 24). However, these 25 strains include 17 distinct methylation profiles (i.e. different combinations of methylation motifs), one of which is found only in strain 234-12. This means that if multiple *K. pneumoniae* strains were present in the same metagenomic sample, DNA methylation profiles may be able to help map plasmid pKpn23412-362 to its true host strain directly from metagenomic data. This epigenetic plasmid-host mapping approach highlights the broad range of applications in which epigenetic profiles can be exploited to address difficult challenges in a variety of clinically relevant situations.

Example 3: Culture Conditions for Bacteria from Eight-Species Mixture and Purification

*Bacteroides* caccae ATCC 43185, *Bacteroides ovatus* ATCC 8483, *Bacteroides thetaiotaomicron* VPI-5482, *Bacteroides vulgatus* ATCC 8492, *Collinsella aerofaciens* ATCC 25986, *Clostridium boltede* ATCC BAA-613, and *Ruminococcus gnavus* ATCC 29149 were grown individually in 10 ml of supplemented Brain-heart infusion broth in an anaerobic chamber from Coy Laboratory Products. *Escherichia coli* MG1655 was grown aerobically in 5 ml of LB broth. Construction of the 10 kb DNA libraries for SMRT sequencing was performed according to the manufacturer's instructions.

Example 4: Mouse Gut Microbiome DNA Purification and Library Preparation

A male 6-week-old NOD/shiltj mouse (no. 001976, Jackson Labs) was housed in a Specific Pathogen Free (SPF) room at New York University Langone Medical Center (NYUMC). At the week 12 of life, the mouse was placed into a clean plastic container in a fume hood, and its fresh fecal pellets were collected in sterilized microcentrifuge tubes and frozen at −80° C. Fecal DNA was extracted using PowerSoil DNA isolation kit (MoBio Labs, Carlsbad, CA). 10 kb library preparation for SMRT sequencing was performed according to the manufacturer's instructions. The bacterial 16S rRNA gene V4 regions were amplified and libraries constructed as previously described by Livanos et al.

Example 5: PHel3 Plasmid Transformation into Three Species

The *E. coli-H. pylori* shuttle plasmid pHel3 was electroporated from *E. coli* strain DH5α to strain CFT073 using MicroPulser following procedures recommended by the manufacturer (Bio-Rad Lab., Hercules, CA). The same plasmid was also introduced from *E. coli* strain DH5α into *H. pylori* strain JP26 by natural transformation as previously described. *E. coli* DH5α carrying pHel3 and CFT073 carrying pHel3 were grown in Luria-Bertani (LB) medium with kanamycin (Km; 50 µg/ml) at 37° C. for 24 hours. *H. pylori* JP26 carrying pHel3 were grown in *Brucella* broth (BB) medium supplemented with 10% newborn calf serum (NBCS) and Km (10 µg/ml) at 37° C. in microaerophilic condition for 48 hours. Bacterial cell pellets of *E. coli* or *H. pylori* cultures were collected by centrifugation, genomic DNA of each culture was purified using Wizard Genomic DNA Purification Kit (Promega, Madison, WI), and plasmid DNA of each culture was purified using QIAprep Spin Miniprep Kit (QIAgen, Valencia, CA). 2 kb library preparation for SMRT sequencing genomic and plasmid DNA for each culture was performed according to the manufacturer's instructions.

Example 6: Three *E. coli* Strains for Synthetic Mixture

Genomic DNA for the three strains of *E. coli*, BAA-2196, BAA-2215, and BAA-2440, were purchased from ATCC and construction of the 10 kb DNA libraries for SMRT sequencing was performed according to the manufacturer's instructions.

Example 7: SMRT Sequencing

Primer was annealed to the size-selected SMRTbell with the full-length libraries (80° C. for 2 minute 30 seconds followed by decreasing the temperature by 0.1° C. to 25° C.). The polymerase-template complex was then bound to the P6 enzyme using a ratio of 10:1 polymerase to SMRTbell at 0.5 nM for 4 hours at 30° C. and then held at 4° C. until ready for magnetic bead loading, prior to sequencing. The magnetic bead-loading step was conducted at 4° C. for 60-minutes per manufacturer's guidelines. The magnetic bead-loaded, polymerase-bound, SMRTbell libraries were placed onto the RSII machine at a sequencing concentration of 125-175 pM and configured for a 240-minute continuous sequencing run.

Example 8: 16s rRNA Sequencing

Sequencing of the 16S V4 region was performed using the Illumina MiSeq platform as previously described by Livanos et al.

Example 9: Sequence Composition-Based Clustering

All k-mer frequency metrics in this study used a k-mer size of 5. Counts of pairs of pentamers that are reverse complements of each other were combined, resulting in a set of 512 5-mers as composition features for each sequence (contig or single-molecule read). Following the procedure described by Alneberg et al., a small pseudo-count was added to each 5-mer count to ensure all counts are non-zero then normalize by the total number of 5-mers in the sequence and log 2-transform the normalized values.

Example 10: Motif methylation scoring

The contig- and read-level polymerase kinetics scores are calculated using the inter-pulse duration (IPD) values provided in the SMRT sequencing reads. Subread normalization, done by log-transforming the ratio of each subread IPD value to the mean of all IPD values in the subread, corrects for any potential slowing of polymerase kinetics over the course of an entire read (which can consists of multiple subreads). Each normalized IPD (nIPD) value in the subread is calculated as follows:

$$nIPD = \ln IPD - \frac{1}{N}\sum_{k=1}^{N} \ln IPD_k$$

where the subread is N bases long and therefore contains N IPD values. To calculate the observed read-level methylation score ($R^o$) for motif i on read j, $$R_{ij}^o,$$

the mean of all nIPD values was taken from all sites of motif i across all subreads of read j:

$$R_{ij}^o = \frac{1}{\sum_{s=1}^{S} M_s}\sum_{s=1}^{S}\sum_{m=1}^{M_s} nIPD_{ms}$$

where each of the S subreads in the read contains $M_s$ motif sites. Longer subreads typically contain more distinct sites of a given motif and generate more reliable methylation scores.

Kinetic variation in the polymerase activity exists even in the absence of methylated bases and is highly correlated with the local nucleotide context surrounding the polymerase as it processes along the template. To account for this baseline variation and remove it from the final methylation score, a corresponding set of control kinetics scores, $$R_i^c$$

was subtracted from the observed kinetics scores, $$R_{ij}^o.$$

These control kinetics scores are motif-matched and calculated similar to $$R_{ij}^o$$

using a sampling of SMRT sequencing unaligned reads (N=20,000) known to be free of any methylation:

$$R_{ij} = R^o_{ij} - R^c_i$$

As no methylated motifs were detected after sequencing an isolate of *Ruminococcus gnavus*, this data served as the non-methylated control set for calculating values of $$R^c_i.$$

These non-methylated control values are used for the motif filtering procedure, but not for the final calculation of methylation profiles. Because the dimensionality reduction with t-SNE calculates a Euclidian distance between two points (i.e. two methylation profiles), the subtraction of a constant (control) vector from both methylation profiles has no effect on their pairwise distances.

Contig-level methylation scores (C) for motif i on contig j, $C_{ij}$, are calculated in a similar manner. The difference is that the scores take into account not just the subreads from a single read, but rather all subreads that align to the contig:

$$C^o_{ij} = \frac{1}{\sum_{s=1}^{S^*} M_s} \sum_{s=1}^{S^*} \sum_{m=1}^{M_s} nIPD_{ms}$$

where each of the S* subreads that align to the contig contain $M_s$ motif sites. Similar to the read-level methylation scores, matching control kinetics scores, $$C^c_i,$$

are generated using a sample of aligned reads (N=20,000) known to be free of methylation and subtracted from the observed kinetics scores, $$C^o_{ij},$$

in order to remove the baseline kinetics variation stemming from local sequence context:

$$C_{ij} = C^o_{ij} - C^c_i$$

As with the read-level methylation scoring, non-methylated control values are used only during the motif filtering procedure but not in the final contig-level methylation scores. Much like the read-level methylation assessment, the reliability of the motif score on a contig increases with the number of motif sites on the contig. Typically, short motifs are present at higher density in the genome than longer, more complex motifs, although exceptions to this rule exist. Therefore, while even the shortest contigs in an assembly are able to return reliable methylation scores for short motifs, longer contigs are usually required to accurately assess the methylation status of more complex motifs. A default methylation score of zero is assigned if no instances of the motif occur on the read or contig.

The optional parameter --cross_cov_bins in the mBin program accepts a file containing contig assignments to bins (in the format contig name, bin id) identified from coverage- and composition-based binning tools. If this parameter is specified, the IPD values used to calculate each contig-level methylation score are aggregated based on binning assignment and bin-level methylation scores are calculated.

Example 11: Motif Filtering for Methylation-Based Clustering

An initial motif-filtering step is necessary to reduce the space of motifs down to only those that have a significant methylation score in the metagenomic mixture. First, due to memory considerations and because a motif could theoretically describe any arbitrary string of bases, the maximum motif length and allowable base configuration of motifs was defined in the initial query space. All possible 4mers, 5mers, and 6mers were considered, for a total of 7,680 contiguous motifs. For bipartite motifs, where a string of non-specific Ns was bookended by sets of specific bases (e.g. CCANNNNNNCAT (SEQ ID NO: 2)), several common configurations often found in prokaryotes were considered. All combinations of the following were considered: 3 or 4 specific bases (beginning), 5 or 6 non-specific Ns (middle), and 3 or 4 specific bases (end). This adds an additional 194,560 possible bipartite motifs to space of motifs to consider for the initial filtering step, for a total of 202,240 motifs. The exact same method can be used to further incorporate 7-mer and 8-mer motifs.

Next, the motif query space was dramatically reduced by randomly sampling a small number of reads (N=20,000) from the mixture and removing from further analysis all motifs that do not return a methylation score above a chosen threshold (1.7) on at least one contig in the assembly (or on at least twenty unaligned reads for read-level binning). Despite choosing a lenient threshold to include many variations of the truly modified motif, this typically reduces the number of motifs to be included in the further analysis by multiple orders of magnitude. A further step searches for multiple specifications representing a single degenerate motif that, if identified, replaces the individual specifications in the final set of motifs. The remaining motifs need not exactly match the most parsimonious versions of the methylated motifs, but they nonetheless will carry some methylation signature that is useful for binning the sequences through subsequent dimensionality reduction analysis. Put another way, the precise number of motifs that remain after filtering is not usually critically important as long as the set of remaining motifs captures the most significant differences between methylation profiles. This property contrasts with existing methods for methylation motif discovery that attempt to identify the single most parsimonious version of a motif.

Example 12: Combined Use of k-Mer Frequency and Methylation Score Matrices

The combination of k-mer frequency and methylation scores used to segregate similar species and strains in the combined infant gut microbiome samples A and B (FIG. 22) was done by z-score transforming both feature matrices after each had been reduced to 2D using t-SNE. The two 2D matrices of z-scores were then combined and the resulting 4D matrix of z-scores was subjected to a second round of t-SNE to get a final 2D matrix.

Example 13: Genome-Genome Similarity

To assess the sequence similarity between two reference genomes, average nucleotide identity (ANI) was calculated using a publicly available web-based tool/.

Example 14: Annotation of Contigs in Methylation Bins

A database of 591 reference genomes isolated from the mouse gut was compiled from four recent studies. Blastn was first run to identify which of the reference sequences had significant matches with the contigs in the nine bins identified using methylation profiles. Significant hits were considered to be alignments >100 bp in length with >97% identity. For each bin, the reference genomes were ranked based on the percentage of the total binned contig sequences that were covered by a significant hit with the reference. The mummer package was then used to align the highest ranked matching references to the contigs in each bin and visualized the alignments (FIG. 9) with the mummer package.

Example 15: Coverage Profiling Unique Regions of Bacteroidales Contigs

After aligning reads from 100 publicly available mouse gut microbiome sequencing data sets to the largest contigs in each of the nine methylation bins, coverage values were normalized according to the standard normalization procedures employed by CONCOCT. To exclude regions where high sequence similarity with other contigs might result in ambiguous mapping and unreliable coverage values, each contig was divided into 10 kb subsequences and excluded any subsequences that displayed any alignments using nucmer. Mean coverage values were calculated for the unique remaining subsequences and these were used to construct the coverage profiles across all 100 samples (FIG. 11).

Example 16: Length-Weighted Processing of Large Contigs

The long reads used in this study often result in a bacterial genome being represented by a small number of very large contigs. The t-SNE dimensionality reduction algorithm places data points in low-dimensional space based on the local similarities in the original high-dimensional space. Species with few large contigs that are represented by only a few points in the high-dimensional space do not contribute significantly to the objective function of the t-SNE algorithm. To adjust for this bias from different contig sizes, a length-weighted representation of all large contigs over 50 kbp in length was use so that each large contig is represented in the matrix of features not by one row, but by N rows, where N is the contig length divided by 50 kbp. The features (column values) for each 50 kbp sub-contig, either k-mer frequency or methylation scores, are the same values that were computed for the original large contig.

Example 17: Power Analysis of Contig Methylation Classification

In order to assess the power of methylation scores to distinguish a contig methylated at a motif sites (case) from a contig that is not methylated at that motif (control), 15,000 normalized IPD (nIPD) values were sampled from GATC sites on each of two large assembled contigs from the mixture of eight bacterial species. The case was the 4.6 Mb contig representing the *E. coli* chromosome, while the second 0.7 Mb contig (control) represents a large assembled portion of the *R. gnavus* genome, which does not contain any methylated motifs based on SMRT sequencing data (see Table 2). The two sets of 15,000 nIPD values were then used as pools from which to sample 2, 4, 6, and 8 values for both the case and control. The nIPD values were used to construct methylation scores for GATC on both the case and control contigs, for each of the four specified nIPD sampling numbers (2, 4, 6, and 8). This process was repeated 10,000 times to create a receiver operating characteristic (ROC) curve (FIG. 2A) showing the effect of the number of nIPD values on creating methylation scores that can distinguish a methylated contig/motif from a non-methylated contig/motif.

Example 18: REBASE Plasmids and Chromosomes Distances

When calculating the Euclidian distance between a plasmid and the chromosome of its host bacterium, the largest chromosome was selected when a bacterium contained more than one chromosome. The empirical distribution of Euclidian distances between the plasmids and randomly selected bacteria was constructed by iterating over all plasmids in REBASE, randomly selecting a bacterium for each plasmid, and computing the distance between the plasmid 5-mer frequency vector and that of the largest chromosome of the selected bacterium.

Example 19: REBASE Survey of Methylome Uniqueness in Simulated Communities

Methylation motifs were gathered for each of the 878 SMRT sequenced bacterial genomes stored in the REBASE database and mock communities of N species were constructed, where N=20, 40, 60, . . . , 200 and each community was created 1,000 times by randomly selecting from the 878 organisms. For each mock community, the methylation motifs for each constituent organism were analyzed and number of organisms with a unique methylome in the community was returned, reported as the fraction of total organisms in the community. Multiple curves in FIG. 3C represent the different results obtained by varying the multi-strain content of the mock communities. The same procedure was again used to analyze only those 155 organisms in REBASE that are known to host at least one plasmid sequence. Mock communities of N species were again constructed, where N=20, 40, 60 and each community was created 1,000 times by randomly selecting from the 155 organisms. Multiple curves in FIG. 3D represent the different results obtained by varying the multi-strain content of the mock communities.

Example 20: REBASE Survey of Methylation Motif Content in Simulated Sequences For each SMRT sequenced genome in the REBASE database, 500 random sequences of length L were simulated, where L=5, 10, 15, . . . , 100 kb. Given the known methylation motifs for each genome, the number of sequences containing the motifs was returned, reported as the fraction of the 500 total simulated sequences. Multiple curves in FIG. 3E represent the different results obtained by varying the percentage of the genome's methylation motifs that are required to be present on each sequence. For instance, the 75% curve represents the number of simulated sequences that contain at least one instance of at least three quarters of the genome's total set of methylation motifs.

Example 21: Re-Assembly of Sequences in Each Methylation Bin

In each methylation bin, the reads aligning to each binned contig were re-assembled with the HGAP3 assembler using a genomeSize parameter modified to reflect the total number of contig bases in each bin.

Example 22: Plasmid Identification in Metagenomic Assembly

A combination of two methods was used to identify circular contigs in metagenomic assemblies: (1) a custom script aligned the 20 kb sequences at the beginning and end of contigs to look for evidence of circularization, and (2) the freely available program Circlator was used with default parameters. Contigs identified as circularized were then manually checked using Gepard to look for visual evidence of circularization, as opposed to signs of mis-assembly.

Example 23: Conjugative Transposon Identification

Small (<200 kb) contigs were classified as conjugative transposons if they contained at least five genes encoding conjugative transposon-related genes. The contigs from each methylation bin (#1-9) were annotated by submission to the RAST server.

Example 24: Synthetic Metagenomic Communities

Eight species synthetic mixture. SMRT reads were obtained separately from eight individual bacterial species (Table 1) and the reads were mixed, without any labeling, by combining one SMRT cell of sequencing from each species to create a synthetic metagenomic mixture at similar relative abundances. Read labels were applied for evaluation purposes only after all binning procedures were completed.

Figure 12:
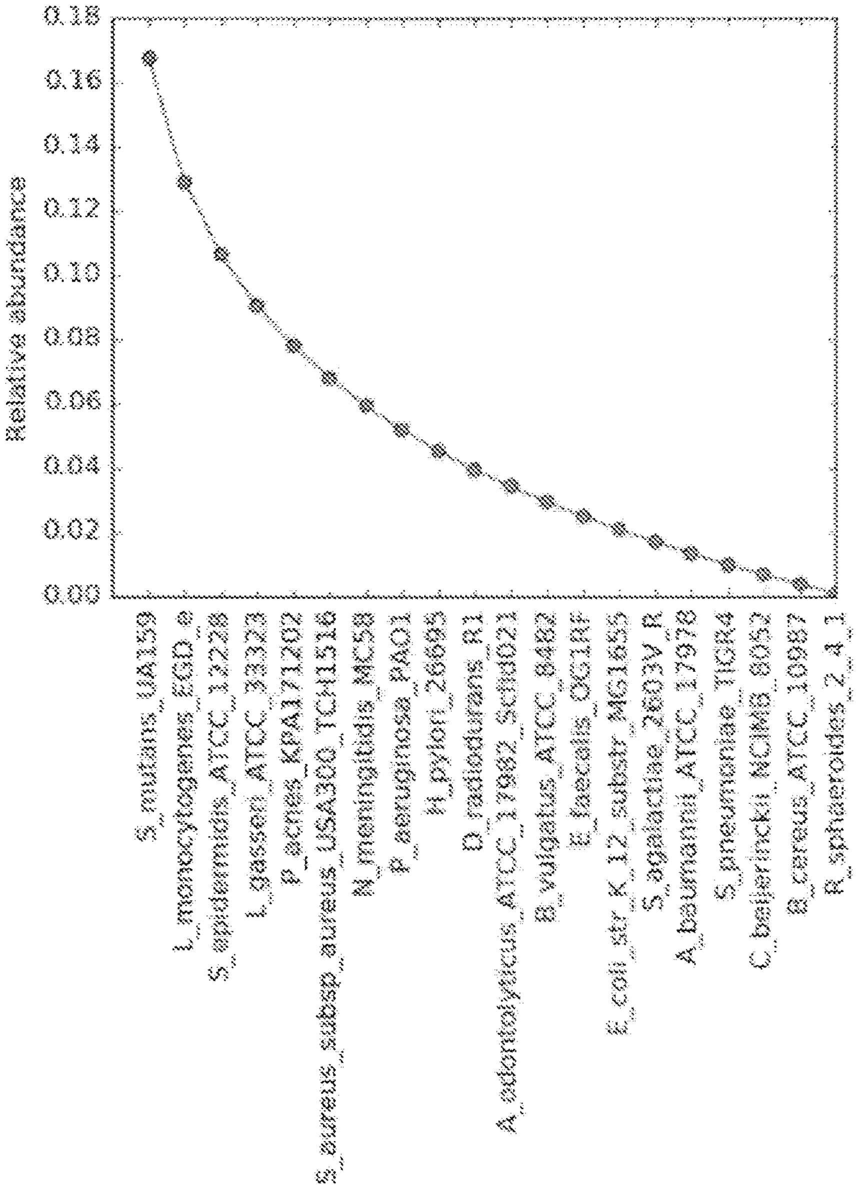
FIG. 12 depicts relative abundances of the 20-species in the Human Microbiome Project Mock Community B modified to follow a log-curve distribution.

Human Microbiome Project Mock Community B. Equimolar amounts of genomic DNA were extracted from twenty different species (Table 10) then combined and sequenced using a Pacific Biosciences RSII instrument. The 49 SMRT cells of reads are publicly available at this the GitHub website. In order to simulate a more realistic mixture with widely varying relative abundances, the raw sequencing reads were downsampled to impose relative species abundances that follow a natural log decay curve (FIG. 12). The species identity for all reads were first determined by aligning the reads to reference assemblies for each of the twenty species. After determining the species mappings for all reads (excluding those with ambiguous alignments), reads from each species were then selected to impose the desired relative abundances. The alignment and labeling procedures were used strictly for data downsampling and were not part of the read-level binning procedure.

Multi-strain mixture of *Helicobacter pylori*. Two strains of *H. pylori*, str. 26695 and str. J99, were sequenced separately using a Pacific Biosciences RSII instrument as part of a previous study. In order to create a multi-strain mixture, reads from one SMRT cell per strain were combined. These strain-specific sets of reads were downsampled using their SMRT cell labels then combined to a mixture containing both strains at 150× coverage (Table 11). Binning procedures did not use any information from the labels.

Multi-strain mixture of *Escherichia coli*. Three strains of *E. coli*, BAA-2196 O26:H11, BAA-2215 O103:H11, and BAA-2440 O111, were sequenced separately using a Pacific Biosciences RSII instrument (see Examples section entitled Three *E. coli* strains for synthetic mixture). The synthetic, multi-strain mixture was created by combining a single SMRT cell from each of these separate sequencing runs (Table 12). Binning procedures did not use any information from the labels.

Example 25: Synthetic Long Read Data

The microbial DNA HM-277D was obtained from BEI Resources and was sequenced in a previous study by Kuleshov et al. using the Illumina TruSeq protocol. These sequencing results were downloaded for the current study using the SRA accession code SRR2822454.

Example 26: SMRT and Synthetic Long Read Alignments

Both synthetic long reads and SMRT reads were aligned to the 20 reference sequences of the genomes contained in the HMP Mock Community B. The synthetic long reads were aligned using the SMRT read aligner blasr with default parameters and "-bestn 1-sam" options. The synthetic long reads were aligned using bwa-mem with default parameters.

Example 27: SMRT and Synthetic Long Read Alignments Downsampling

The *.bam files containing the aligned synthetic long reads and SMRT reads for the 20 species in the HMP Mock Community B were analyzed to count the total number of aligned bases in each. For each reference, the smaller number of aligned bases was chosen as the target number of aligned bases and the file with the larger number of aligned bases was selected for downsampling. The target fraction is calculated by dividing the target number of aligned bases by the original number of bases. The following samtools command was used to generate the downsampled file:

samtools view-s 1.[target_frac]-h-b original.bam>downsampled.bam

The results of this downsampling are summarized in Table 17.

Example 28: Infant Gut Microbiome Samples

DNA was isolated from stool samples taken from two Finnish children. The donor of Sample A (containing *B. dorei* str. 105) was 13.5 months of age, while Sample B (containing *B. dorei* str. 439) was obtained from child at 3.3 months of age. Full details on sample isolation and DNA extraction are provided by Leonard et al. A summary of the SMRT sequencing statistics can be found in Table 19.

Example 29: T-SNE Embedding for Dimensionality Reduction

The high-dimensional matrix of features (e.g. k-mer frequencies, methylation scores, or a combination) for all sequences was subjected to the Barnes-Hut implementation of t-distributed stochastic neighbor embedding (t-SNE). The Barnes-Hut approximation of t-SNE reduces the computational complexity from $O(N^2)$ to $O(N \log N)$, making it feasible to generate 2D maps of hundreds of thousands of metagenomic sequences containing hundreds of features. All runs used the default parameters for perplexity (30) and theta (0.5).

Example 30: Metagenomic Assembly

All metagenomic assemblies in this study used the hierarchical genome-assembly process (HGAP3). With the exception of the parameter specifying the expected genome size to be assembled, all default parameters were used. The expected genome size parameter is used to determine the optimum number of long seed reads and was adjusted based on the expected complexity of the metagenome. Specifically, the genome size was set to 40 Mb for the synthetic mixture of eight bacterial species assembly, 66 Mb for the 20-member HMP assembly, 20 Mb for the combined infant gut microbiome samples A and B assembly, 1.6 Mb for the combined and separate *H. pylori* strain assemblies, and 20 Mb for the infant gut microbiome sample A assembly.

Example 31: Metagenomic Annotations Using Kraken

Kraken version 0.10.5-beta was configured to use two databases. The database used to annotate sequences from the Human Microbiome Project (HMP) Mock Community B consisted of reference sequences for the twenty known species included in the mock community (Table 10). All other Kraken annotations used a database consisting of the RefSeq complete set of bacterial/archaeal genomes (using "--download-library bacteria") and draft assemblies of five *Bacteroides* dorei strains. Database construction from these libraries and all Kraken annotations used default parameters.

Example 32: Labeling *B. dorei* Contigs by Strain

In the infant gut microbiome t-SNE maps showing the combined assemblies of samples A and B (FIG. 20-22), all contigs other than those labeled as belonging to *B. dorei* were annotated using Kraken. The contigs belonging to the two *B. dorei* strains, however, were manually labeled by first aligning the reads from the combined samples to the fully assembled references for each *B. dorei* strain (strain 105: CP007619; strain 439: CP008741). The contig-labeling assignments were determined by examining the reads aligning to the either of the *B. dorei* references and counting how many of these reads aligned to each of the assembled contigs. For example, if the majority of the reads aligning to a contig aligned to the strain 105 reference, the contig was labeled as belonging to strain 105. However, if the majority aligned to the strain 439 reference, the contig was labeled as belonging to strain 439.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

REFERENCES

1 Turnbaugh, P. J. et al. The Human Microbiome Project. Nature 449, 804-810 (2007).
2. Consortium, T. H. M. P. Structure, function and diversity of the healthy human microbiome. Nature 486, 207-214 (2012).
3. Cho, I. & Blaser, M. J. The human microbiome: at the interface of health and disease. Nat. Rev. Genet. 13, 260-270 (2012).
4. Vangay, P., Ward, T., Gerber, J. S. & Knights, D. Antibiotics, pediatric dysbiosis, and disease. Cell Host Microbe 17, 553-564 (2015).
5. Luo, C. et al. ConStrains identifies microbial strains in metagenomic datasets. Nat. Biotechnol. 33, 1045-1052 (2015).
6. Faith, J. J., Colombel, J.-F. & Gordon, J. I. Identifying strains that contribute to complex diseases through the study of microbial inheritance. Proc. Natl. Acad. Sci. U.S.A. 112, 633-40 (2015).
7. Langille, M. G. et al. Predictive functional profiling of microbial communities using 16S rRNA marker gene sequences. Nat. Biotechnol. 31, 814-821 (2013).
8. Greenblum, S., Carr, R. & Borenstein, E. Extensive strain-level copy-number variation across human gut microbiome species. Cell 160, 583-594 (2015).
9. Qin, J. et al. A human gut microbial gene catalogue established by metagenomic sequencing. Nature 464, 59-65 (2010).
10. Li, J. et al. An integrated catalog of reference genes in the human gut microbiome. Nat Biotech 32, 834-41 (2014).
11. Venter, J. C. et al. Environmental genome shotgun sequencing of the Sargasso Sea. Science 304, 66-74 (2004).
12. Tyson, G. W. et al. Community structure and metabolism through reconstruction of microbial genomes from the environment. Nature 428, 37-43 (2004).
13. Modi, S. R., Lee, H. H., Spina, C. S. & Collins, J. J. Antibiotic treatment expands the resistance reservoir and ecological network of the phage metagenome. Nature 499, 219-22 (2013).
14. Cleary, B. et al. Detection of low-abundance bacterial strains in metagenomic datasets by eigengenome partitioning. Nat. Biotechnol. 33, 1053-1060 (2015).
15. Kuleshov, V. et al. Synthetic long-read sequencing reveals intraspecies diversity in the human microbiome. Nat. Biotechnol. 34, 64-69 (2015).
16. Meyer, F., Paarmann, D., D'Souza, M. & Etal. The metagenomics RAST server—a public resource for the automatic phylo-genetic and functional analysis of metagenomes. BMC Bioinformatics 9, 386 (2008).
17. Brady, A. & Salzberg, S. L. Phymm and PhymmBL: metagenomic phylogenetic classification with interpolated Markov models. Nat. Methods 6, 673-6 (2009).
18. Wood, D. E. & Salzberg, S. L. Kraken: ultrafast metagenomic sequence classification using exact alignments. Genome Biol. 15, R46 (2014).
19. Borozan, I. & Ferretti, V. CSSSCL: a python package that uses Combined Sequence Similarity Scores for accurate taxonomic CLassification of long and short sequence reads. Bioinformatics 1-3 (2015). doi: 10.1093/bioinformatics/btv587
20. Sunagawa, S. et al. Metagenomic species profiling using universal phylogenetic marker genes. Nat. Methods 10, 1196-1199 (2013).

21. Bazinet, A. L. & Cummings, M. P. A comparative evaluation of sequence classification programs. BMC Bioinformatics 13, 92 (2012).
22. Segata, N. et al. Metagenomic microbial community profiling using unique clade-specific marker genes. Nat. Methods 9, 811-4 (2012).
23. Truong, D. T. et al. MetaPhlAn2 for enhanced metagenomic taxonomic profiling. Nat. Methods 12, 902-903 (2015).
24. Chatterji, S., Yamazaki, I., Bai, Z. & Eisen, J. a. CompostBin: A DNA composition-based algorithm for binning environmental shotgun reads. Lect. Notes Comput. Sci. (including Subser. Lect. Notes Artif. Intell. Lect. Notes Bioinformatics) 4955 LNBI, 17-28 (2008).
25. Kislyuk, A., Bhatnagar, S., Dushoff, J. & Weitz, J. S. Unsupervised statistical clustering of environmental shotgun sequences. BMC Bioinformatics 10, 316 (2009).
26. Scholz, M. et al. Strain-level microbial epidemiology and population genomics from shotgun metagenomics. Nat. Methods 13, (2016).
27. Saeed, I., Tang, S. L. & Halgamuge, S. K. Unsupervised discovery of microbial population structure within metagenomes using nucleotide base composition. Nucleic Acids Res. 40, (2012).
28. Iverson, V. et al. Untangling genomes from metagenomes: revealing an uncultured class of marine Euryarchaeota. Science 335, 587-90 (2012).
29. Laczny, C., Pinel, N., Vlassis, N. & Wilmes, P. Alignment-free Visualization of Metagenomic Data by Nonlinear Dimension Reduction. Sci. Rep. 1-12 (2014). doi: 10.1038/srep04516
30. Laczny, C. C. et al. VizBin—an application for reference-independent visualization and human-augmented binning of metagenomic data. Microbiome 1-7 (2015). doi: 10.1186/s40168-014-0066-1
31. Gisbrecht, A., Hammer, B., Mokbel, B. & Sczyrba, A. Nonlinear dimensionality reduction for cluster identification in metagenomic samples. Proc. Int. Conf. Inf. Vis. 174-179 (2013). doi: 10.1109/IV.2013.22
32. Carr, R., Shen-Orr, S. S. & Borenstein, E. Reconstructing the Genomic Content of Microbiome Taxa through Shotgun Metagenomic Deconvolution. PLOS Comput. Biol. 9, (2013).
33. Sharon, I. et al. Time series community genomics analysis reveals rapid shifts in bacterial species, strains, and phage during infant gut colonization. Genome Res. 23, 111-20 (2013).
34. Albertsen, M. et al. Genome sequences of rare, uncultured bacteria obtained by differential coverage binning of multiple metagenomes. Nat. Biotechnol. 31, 533-8 (2013).
35. Nielsen, H. B. et al. Identification and assembly of genomes and genetic elements in complex metagenomic samples without using reference genomes. Nat. Biotechnol. 32, (2014).
36. Alneberg, J. et al. Binning metagenomic contigs by coverage and composition. Nat. Methods 11, (2014).
37. Tsai, Y.-C. et al. Resolving the Complexity of Human Skin Metagenomes Using Single-Molecule Sequencing. MBio 7, 1-13 (2016).
38. Marbouty, M. et al. Metagenomic chromosome conformation capture (meta3C) unveils the diversity of chromosome organization in microorganisms. Elife 3, e03318 (2014).
39. Flot, J. F., Marie-Nelly, H. & Koszul, R. Contact genomics: scaffolding and phasing (meta) genomes using chromosome 3D physical signatures. FEBS Lett. 589, 2966-2974 (2015).
40. Burton, J. N., Liachko, I., Dunham, M. J. & Shendure, J. Species-Level Deconvolution of Metagenome Assemblies with Hi-C-Based Contact Probability Maps. G3 (Bethesda). 4, 1339-1346 (2014).
41. Beitel, C. W. et al. Strain- and plasmid-level deconvolution of a synthetic metagenome by sequencing proximity ligation products. PeerJ 2, e415 (2014).
42. Flusberg, B. a et al. Direct detection of DNA methylation during single-molecule, real-time sequencing. Nat. Methods 7, 461-5 (2010).
43. Eid, J. et al. Real-time DNA sequencing from single polymerase molecules. Science (80-.). 323, 133-138 (2009).
44. Casadesus, J. & Low, D. Epigenetic gene regulation in the bacterial world. Microbiol. Mol. Biol. Rev. 70, 830-56 (2006).
45. Blow, M. J. et al. The Epigenomic Landscape of Prokaryotes. PLOS Genet. 12, e1005854 (2016).
46. Kobayashi, I., Nobusato, a, Kobayashi-Takahashi, N. & Uchiyama, I. Shaping the genome-restriction-modification systems as mobile genetic elements. Curr. Opin. Genet. Dev. 9, 649-656 (1999).
47. Conlan, S. et al. Single-molecule sequencing to track plasmid diversity of hospital-associated carbapenemase-producing Enterobacteriaceae. Sci. Transl. Med. 6, 254ra126 (2014).
48. Furuta, Y. et al. Methylome diversification through changes in DNA methyltransferase sequence specificity. PLOS Genet. 10, e1004272 (2014).
49. Fang, G. et al. Genome-wide mapping of methylated adenine residues in pathogenic *Escherichia coli* using single-molecule real-time sequencing. Nat. Biotechnol. 30, 1232-9 (2012).
50. Leonard, M. T. et al. The methylome of the gut microbiome: disparate Dam methylation patterns in intestinal *Bacteroides* dorei. Front. Microbiol. 5, 361 (2014).
51. Schadt, E. E. et al. Modeling kinetic rate variation in third generation DNA sequencing data to detect putative modifications to DNA bases. Genome Res. 23, 129-41 (2013).
52. Beaulaurier, J. et al. Single molecule-level detection and long read-based phasing of epigenetic variations in bacterial methylomes. Nat. Commun. 6, 7438 (2015).
53. Chin, C.-S. et al. Nonhybrid, finished microbial genome assemblies from long-read SMRT sequencing data. Nat. Methods 10, 563-9 (2013).
54. van der Maaten, L. & Hinton, G. Visualizing Data using t-SNE. J. Mach. Learn. Res. 9, 2579-2605 (2008).
55. Van Der Maaten, L. Accelerating t-sne using tree-based algorithms. J. Mach. Learn. Res. 15, 3221-3245 (2014).
56. Rousseeuw, P. J. Silhouettes: A graphical aid to the interpretation and validation of cluster analysis. J. Comput. Appl. Math. 20, 53-65 (1987).
57. Parks, D. H., Imelfort, M., Skennerton, C. T., Hugenholtz, P. & Tyson, G. W. CheckM: assessing the quality of microbial genomes recovered from isolates, single cells, and metagenomes. Genome Res. 25, 1043-55 (2015).
58. Xiao, L. et al. A catalog of the mouse gut metagenome. Nat. Biotechnol. 33, 1103-8 (2015).
59. Ormerod, K. L. et al. Genomic characterization of the uncultured Bacteroidales family S24-7 inhabiting the guts of homeothermic animals. Microbiome 4, 36 (2016).

60. Uchimura, Y. et al. Complete Genome Sequences of 12 Species of Stable Defined Moderately Diverse Mouse Microbiota 2. Genome Announc. 4, 4-5 (2016).
61. Wannemuehler, M. J., Overstreet, A., Ward, D. V & Phillips, J. Draft Genome Sequences of the Altered Schaedler Flora, a Defined Bacterial Community from Gnotobiotic Mice. Genome Announc. 2, 1-2 (2014).
62. Kim, M., Oh, H., Park, S. & Chun, J. Towards a taxonomic coherence between average nucleotide identity and 16S rRNA gene sequence similarity for species demarcation of prokaryotes. Int J Syst Evol Microbiol 64, 346-351 (2014).
63. Imelfort, M. et al. GroopM: An automated tool for the recovery of population genomes from related metagenomes. PeerJ 2, e409v1 (2014).
64. Kang, D. D., Froula, J., Egan, R. & Wang, Z. MetaBAT, an efficient tool for accurately reconstructing single genomes from complex microbial communities. PeerJ 3, e1165 (2015).
65. Slater, F. R., Bailey, M. J., Tett, A. J. & Turner, S. L. Progress towards understanding the fate of plasmids in bacterial communities. FEMS Microbiol. Ecol. 66, 3-13 (2008).
66. Thomas, C. M. & Nielsen, K. M. Mechanisms of, and barriers to, horizontal gene transfer between bacteria. Nat. Rev. Microbiol. 3, 711-721 (2005).
67. Roberts, R. J., Vincze, T., Posfai, J. & Macelis, D. REBASE—a database for DNA restriction and modification: Enzymes, genes and genomes. Nucleic Acids Res. 43, D298-D299 (2015).
68. Norberg, P., Bergstrom, M., Jethava, V., Dubhashi, D. & Hermansson, M. The IncP-1 plasmid backbone adapts to different host bacterial species and evolves through homologous recombination. Nat. Commun. 2, 268 (2011).
69. Heuermann, D. & Haas, R. A stable shuttle vector system for efficient genetic complementation of *Helicobacter pylori* strains by transformation and conjugation. Mol. Gen. Genet. 257, 519-528 (1998).
70. Coyne, M. J. et al. Evidence of Extensive DNA Transfer between Bacteroidales Species within the Human Gut. MBio 5, e01305-14 (2014).
71. Nagarajan, N. & Pop, M. Sequence assembly demystified. Nat. Rev. Genet. 14, 157-67 (2013).
72. Dröge, J. & Mchardy, A. C. Taxonomic binning of metagenome samples generated by next-generation sequencing technologies. Brief. Bioinform. 13, 646-655 (2012).
73. Dutilh, B. E. et al. A highly abundant bacteriophage discovered in the unknown sequences of human faecal metagenomes. Nat. Commun. 5, 1-11 (2014).
74. Krebes, J. et al. The complex methylome of the human gastric pathogen *Helicobacter pylori*. Nucleic Acids Res. 1-18 (2013). doi: 10.1093/nar/gkt1201
75. Kuleshov, V. et al. Whole-genome haplotyping using long reads and statistical methods. Nat. Biotechnol. 32, (2014).
76. McCoy, R. C. et al. Illumina TruSeq synthetic long-reads empower de novo assembly and resolve complex, highly-repetitive transposable elements. PLOS One 9, (2014).
77. Shin, S. C. et al. Advantages of Single-Molecule Real-Time Sequencing in High-GC Content Genomes. PLOS One 8, (2013).
78. Chaisson, M. J. P. et al. Resolving the complexity of the human genome using single-molecule sequencing. Nature 517, 608-611 (2015).
79. Wu, D. et al. A phylogeny-driven genomic encyclopaedia of Bacteria and Archaea. Nature 462, 1056-1060 (2009).
80. Luef, B. et al. Diverse uncultivated ultra-small bacterial cells in groundwater. Nat. Commun. 6, 6372 (2015).
81. Clarke, J. et al. Continuous base identification for single-molecule nanopore DNA sequencing. Nat. Nanotechnol. 4, 265-270 (2009).
82. Manrao, E. a et al. Reading DNA at single-nucleotide resolution with a mutant MspA nanopore and phi29 DNA polymerase. Nat. Biotechnol. 30, 349-53 (2012).
83. Laszlo, A. H. et al. Detection and mapping of 5-methylcytosine and 5-hydroxymethylcytosine with nanopore MspA. Proc. Natl. Acad. Sci. U.S.A. 110, 18904-9 (2013).
84. Lasken, R. S. & McLean, J. S. Recent advances in genomic DNA sequencing of microbial species from single cells. Nat. Rev. Genet. 15, 577-84 (2014).
85. Caporaso, J. G. et al. QIIME allows analysis of high-throughput community sequencing data. Nat. Publ. Gr. 7, 335-336 (2010).
86. Kukko, M. et al. Dynamics of diabetes-associated autoantibodies in young children with human leukocyte antigen-conferred risk of type 1 diabetes recruited from the general population. J. Clin. Endocrinol. Metab. 90, 2712-2717 (2005).
87. Davis-Richardson, A. G. et al. *Bacteroides dorei* dominates gut microbiome prior to autoimmunity in Finnish children at high risk for type 1 diabetes. Front. Microbiol. 5, 1-11 (2014).
88. Becker, L. et al. Complete genome sequence of a CTX-M-15-producing *Klebsiella pneumoniae* outbreak strain from multilocus sequence type 514. Genome Announc. 3, e00742-15 (2015).
89. Villa, L., García-Fernández, A., Fortini, D. & Carattoli, A. Replicon sequence typing of IncF plasmids carrying virulence and resistance determinants. J. Antimicrob. Chemother. 65, 2518-2529 (2010).
90. Sokol, H. et al. *Faecalibacterium prausnitzii* is an anti-inflammatory commensal bacterium identified by gut microbiota analysis of Crohn disease patients. Proc. Natl. Acad. Sci. U.S.A 105, 16731-6 (2008).
91. Livanos, A. E. et al. Antibiotic-mediated gut microbiome perturbation accelerates development of type 1 diabetes in mice. Nat. Microbiol. 1, 16140 (2016).
92. Zhang, X. S. & Blaser, M. J. Natural transformation of an engineered *Helicobacter pylori* strain deficient in type II restriction endonucleases. J. Bacteriol. 194, 3407-3416 (2012).
93. Feng, Z. et al. Detecting DNA modifications from SMRT sequencing data by modeling sequence context dependence of polymerase kinetic. PLOS Comput. Biol. 9, e1002935 (2013).
94. Rodriguez-r, L. M. & Konstantinidis, K. T. The enveomics collection: a toolbox for specialized analyses of microbial genomes and metagenomes microbial genomes and metagenomes. PeerJ Prepr. (2016).
95. Kurtz, S. et al. Versatile and open software for comparing large genomes. Genome Biol. 5, R12 (2004).
96. Hunt, M. et al. Circlator: automated circularization of genome assemblies using long sequencing reads. Genome Biol. 16, 294 (2015).
97. Krumsiek, J., Arnold, R. & Rattei, T. Gepard: A rapid and sensitive tool for creating dotplots on genome scale. Bioinformatics 23, 1026-1028 (2007).

98. Aziz, R. K. et al. The RAST Server: Rapid Annotations using Subsystems Technology. BMC Genomics 9, 75 (2008).

99. Chaisson, M. & Tesler, G. Mapping single molecule sequencing reads using basic local alignment with successive refinement (BLASR): application and theory. BMC Bioinformatics (2012).

100. Li, H. & Durbin, R. Fast and accurate long-read alignment with Burrows-Wheeler transform. Bioinformatics 26, 589-95 (2010).

101. Li, H. et al. The Sequence Alignment/Map format and SAMtools. Bioinformatics 25, 2078-9 (2009).

What is claimed is:

1. A method of deconvoluting genomes of a plurality of unknown prokaryotic organisms in a microbiome sample, said method comprising the steps of:

a) sequencing nucleic acids of the plurality of unknown prokaryotic organisms in the microbiome sample obtained from a subject using single-molecule long reads sequencing technology, wherein two or more of the prokaryotic organisms in the microbiome sample have an average nucleotide identity of greater than about 95%, and wherein the sequencing comprises the step of identifying methylated nucleotides, and at least one of the steps of:
   i) sequencing single molecule reads of the nucleic acids; and
   ii) assembling contigs from single molecule reads of the nucleic acids;

b) assigning a methylation score predicting the likelihood and the extent of methylation of the identified methylated nucleotides for sequence motifs of the nucleic acids based on the assembled contigs of the nucleic acids and/or the single molecule reads of the nucleic acids, wherein a methylation score is assigned to the sequence motifs, the sequence motifs comprising at least: (i) all possible 4mer, 5mer, and 6mer contiguous sequence motifs, and (ii) all bipartite sequence motifs having 5 or 6 non-specific bases bookended by 3 or 4 specific bases;

c) removing sequence motifs via motif filtering that do not return a methylation score above a chosen threshold in at least one contig of the assembled contigs of the nucleic acids or on at least twenty unassigned reads for read-level binning, wherein the motif filtering does not identify the single most parsimonious version of any sequence motif;

d) determining nucleic acid methylation profiles of the assembled contigs of the nucleic acids or the single molecule reads of the nucleic acids in the microbiome sample based on the sequence motifs identified in step (c);

e) separating the assembled contigs of the nucleic acids and/or the single molecule reads of the nucleic acids into bins corresponding to distinct prokaryotic organisms based on the methylation profiles of step (d); and f) assembling the bins of step (e), thereby obtaining assembled genomes of the distinct bacterial organisms in the microbiome sample, thereby deconvoluting genomes of the prokaryotic organisms in a microbiome sample.

2. The method of claim 1, further comprising the step of combining the methylation profiles of step (d) with other sequence features of the nucleic acids of the plurality of unknown prokaryotic organisms in the microbiome sample prior to separating the assembled contigs of the nucleic acids and/or the single molecule reads of the nucleic acids into bins.

3. The method of claim 2, wherein the other sequence features comprise k-mer frequency profiles and coverage profiles across multiple samples.

4. The method of claim 1, further comprising the step of combining contig binning assignments from cross-coverage and composition-based binning tools with methylation scores in each bin, resulting in detection of methylated motifs in each bin and assignment of bin-level methylation scores in the microbiome sample.

5. The method of claim 1, further comprising the step of aligning the single molecule reads of the nucleic acids to the contigs assembled from single molecule reads of the nucleic acids of step (a) prior to the step of assigning a methylation score.

6. The method of claim 1, wherein the methylated nucleotides are selected from N6-methyladenine, N4-methylcytosine, and 5-methylcytosine and combinations thereof.

7. The method of claim 1, wherein the prokaryotic organisms comprise bacterial organisms, archaeal organisms, and combinations thereof.

8. A method of mapping a mobile genetic element to a prokaryotic host organism in a microbiome sample comprising a plurality of unknown prokaryotic organisms, said method comprising the steps of:

a) sequencing nucleic acids of the plurality of unknown prokaryotic organisms in the microbiome sample obtained from a subject using single-molecule long reads sequencing technology, wherein two or more of the prokaryotic organisms in the microbiome sample have an average nucleotide identity of greater than about 95%, and wherein the sequencing comprises the step of identifying methylated nucleotides and at least one of the steps of
   i) sequencing single molecule reads of the nucleic acids; and
   ii) assembling contigs from single molecule reads of the nucleic acids;

b) assigning a methylation score predicting the likelihood and the extent of methylation of the identified methylated nucleotides for sequence motifs of the nucleic acids on the assembled contigs of the nucleic acids and/or the single molecule reads of the nucleic acids, wherein a methylation score is assigned to the sequence motifs, the sequence motifs comprising at least: (i) all possible 4mer, 5mer, and 6mer contiguous sequence motifs, and (ii) all bipartite sequence motifs having 5 or 6 non-specific bases bookended by 3 or 4 specific bases;

c) removing sequence motifs via motif filtering that do not return a methylation score above a chosen threshold in at least one contig of the assembled contigs of the nucleic acids or on at least twenty unassigned reads for read-level binning, wherein the motif filtering does not identify the single most parsimonious version of any sequence motif;

d) determining nucleic acid methylation profiles of the assembled contigs of the nucleic acids or the single molecule reads of the nucleic acids of at least one prokaryotic host organism and at least one mobile genetic element in the microbiome sample based on the sequence motifs identified in step (c);

e) comparing the nucleic acid methylation profiles of the at least one prokaryotic host organism in the microbiome sample and the at least one mobile genetic element in the microbiome sample and determining whether a match exists between said methylation profiles; and f) repeating steps (d) and (e) until a match between the mobile genetic element and the prokaryotic host organism is identified;

thereby mapping the mobile genetic element to the prokaryotic host organism.

9. The method of claim 8, wherein the mobile genetic element is a plasmid, a transposon, or a bacteriophage.

10. The method of claim 8, wherein the mobile genetic element is greater than 10 kbp in length.

11. The method of claim 8, wherein the mobile genetic element: confers antibiotic resistance to the prokaryotic host organism, encodes a virulence factor in the prokaryotic host organism, or provides a metabolic function to the prokaryotic host organism.

12. The method of claim 8, wherein the nucleic acid methylation profile is a DNA methylation profile.

13. The method of claim 8, wherein step (a) comprises sequencing nucleic acids of the prokaryotic host organism and the mobile genetic element using a single-molecule long read real time (SMRT) technology or nanopore sequencing technology.

14. The method of claim 8, wherein the methylated nucleotides are selected from N6-methyladenine, N4-methylcytosine, and 5-methylcytosine and combinations thereof.

15. The method of claim 8, further comprising the step of aligning the single molecule reads of the nucleic acids to the contigs assembled from single molecule reads of the nucleic acids of step (a) prior to the step of assigning a methylation score.

* * * * *

SEQUENCE LISTING

```
<160> NUMBER OF SEQ ID NOS: 64

<210> SEQ ID NO 1
<211> LENGTH: 12
<212> TYPE: DNA
<213> ORGANISM: Klebsiella pneumoniae
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 1

ccaynnnnnt cc                                                    12


<210> SEQ ID NO 2
<211> LENGTH: 12
<212> TYPE: DNA
<213> ORGANISM: Bacteroides thetaiotaomicron
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 2

ccannnnnnc at                                                    12


<210> SEQ ID NO 3
<211> LENGTH: 12
<212> TYPE: DNA
<213> ORGANISM: Bacteroides thetaiotaomicron
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 3

atgnnnnnnt gg                                                    12


<210> SEQ ID NO 4
<211> LENGTH: 11
<212> TYPE: DNA
<213> ORGANISM: Bacteroides sp.
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t
```

<400> SEQUENCE: 4
cagnnnnngg a 11

<210> SEQ ID NO 5
<211> LENGTH: 12
<212> TYPE: DNA
<213> ORGANISM: Bacteroides vulgatus
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 5
tcacnnnnna tg 12

<210> SEQ ID NO 6
<211> LENGTH: 11
<212> TYPE: DNA
<213> ORGANISM: Bacteroides vulgatus
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 6
cacnnnnnat g 11

<210> SEQ ID NO 7
<211> LENGTH: 13
<212> TYPE: DNA
<213> ORGANISM: Escherichia coli
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 7
gcacnnnnnn gtt 13

<210> SEQ ID NO 8
<211> LENGTH: 13
<212> TYPE: DNA
<213> ORGANISM: Escherichia coli
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 8
aacnnnnnng tgc 13

<210> SEQ ID NO 9

```
<211> LENGTH: 14
<212> TYPE: DNA
<213> ORGANISM: Unknown
<220> FEATURE:
<223> OTHER INFORMATION: Description of Unknown: Bacteroidales (order)
      motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 9

ccasnnnnnn atgt                                                         14


<210> SEQ ID NO 10
<211> LENGTH: 13
<212> TYPE: DNA
<213> ORGANISM: Unknown
<220> FEATURE:
<223> OTHER INFORMATION: Description of Unknown: Bacteroidales (order)
      motif
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 10

tcagnnnnnc ctc                                                          13


<210> SEQ ID NO 11
<211> LENGTH: 14
<212> TYPE: DNA
<213> ORGANISM: Unknown
<220> FEATURE:
<223> OTHER INFORMATION: Description of Unknown: Bacteroidales (order)
      motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 11

ccagnnnnnn vtgg                                                         14


<210> SEQ ID NO 12
<211> LENGTH: 14
<212> TYPE: DNA
<213> ORGANISM: Unknown
<220> FEATURE:
<223> OTHER INFORMATION: Description of Unknown: Bacteroidales (order)
      motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 12
```

ccagnnnnnn rtgg 14

<210> SEQ ID NO 13
<211> LENGTH: 13
<212> TYPE: DNA
<213> ORGANISM: Unknown
<220> FEATURE:
<223> OTHER INFORMATION: Description of Unknown: Actinobacteria (phylum) motif
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 13
gattnnnnnc agt 13

<210> SEQ ID NO 14
<211> LENGTH: 13
<212> TYPE: DNA
<213> ORGANISM: Unknown
<220> FEATURE:
<223> OTHER INFORMATION: Description of Unknown: Actinobacteria (phylum) motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 14
gattnnnnnn agt 13

<210> SEQ ID NO 15
<211> LENGTH: 13
<212> TYPE: DNA
<213> ORGANISM: Unknown
<220> FEATURE:
<223> OTHER INFORMATION: Description of Unknown: Bacteroidales (order) motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 15
agcannnnnn rtc 13

<210> SEQ ID NO 16
<211> LENGTH: 13
<212> TYPE: DNA
<213> ORGANISM: Unknown
<220> FEATURE:
<223> OTHER INFORMATION: Description of Unknown: Bacteroidales (order) motif
<220> FEATURE:
<221> NAME/KEY: modified_base
<222> LOCATION: (4)..(9)
<223> OTHER INFORMATION: a, c, t, g, unknown or other
<220> FEATURE:

<221> NAME/KEY: misc_feature
<222> LOCATION: (4)..(9)
<223> OTHER INFORMATION: n is a, c, g, or t

<400> SEQUENCE: 16
gacnnnnnnt gct 13

<210> SEQ ID NO 17
<211> LENGTH: 11
<212> TYPE: DNA
<213> ORGANISM: Unknown
<220> FEATURE:
<223> OTHER INFORMATION: Description of Unknown: Bacteroidales (order) motif
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 17
ccannnnntc g 11

<210> SEQ ID NO 18
<211> LENGTH: 13
<212> TYPE: DNA
<213> ORGANISM: Unknown
<220> FEATURE:
<223> OTHER INFORMATION: Description of Unknown: Bacteria (kingdom) motif
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 18
gaagnnnnna cgt 13

<210> SEQ ID NO 19
<211> LENGTH: 14
<212> TYPE: DNA
<213> ORGANISM: Unknown
<220> FEATURE:
<223> OTHER INFORMATION: Description of Unknown: Bacteria (kingdom) motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 19
cgagnnnnnn cctt 14

<210> SEQ ID NO 20
<211> LENGTH: 12
<212> TYPE: DNA
<213> ORGANISM: Unknown
<220> FEATURE:
<223> OTHER INFORMATION: Description of Unknown: Proteobacteria (phylum) motif

```
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 20

gatcnnnnnw mt                                                12


<210> SEQ ID NO 21
<211> LENGTH: 13
<212> TYPE: DNA
<213> ORGANISM: Unknown
<220> FEATURE:
<223> OTHER INFORMATION: Description of Unknown: Proteobacteria (phylum)
      motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 21

gatcnnnnnn wsa                                               13


<210> SEQ ID NO 22
<211> LENGTH: 13
<212> TYPE: DNA
<213> ORGANISM: Unknown
<220> FEATURE:
<223> OTHER INFORMATION: Description of Unknown: Bacteria (kingdom)
      motif
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 22

actnnnnnna atc                                               13


<210> SEQ ID NO 23
<211> LENGTH: 13
<212> TYPE: DNA
<213> ORGANISM: Unknown
<220> FEATURE:
<223> OTHER INFORMATION: Description of Unknown: Bacteria (kingdom)
      motif
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 23

accannnnna atc                                               13


<210> SEQ ID NO 24
<211> LENGTH: 11
```

<212> TYPE: DNA
<213> ORGANISM: Helicobacter pylori
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 24
aagnnnnnct t 11

<210> SEQ ID NO 25
<211> LENGTH: 12
<212> TYPE: DNA
<213> ORGANISM: Helicobacter pylori
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 25
gaghnnnnnc tt 12

<210> SEQ ID NO 26
<211> LENGTH: 12
<212> TYPE: DNA
<213> ORGANISM: Helicobacter pylori
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 26
cyannnnnnt ga 12

<210> SEQ ID NO 27
<211> LENGTH: 12
<212> TYPE: DNA
<213> ORGANISM: Helicobacter pylori
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 27
tcannnnnnt rg 12

<210> SEQ ID NO 28
<211> LENGTH: 12
<212> TYPE: DNA
<213> ORGANISM: Helicobacter pylori
<220> FEATURE:
<221> NAME/KEY: modified_base
<222> LOCATION: (4)..(9)
<223> OTHER INFORMATION: a, c, t, g, unknown or other
<220> FEATURE:

<221> NAME/KEY: misc_feature
<222> LOCATION: (4)..(9)
<223> OTHER INFORMATION: n is a, c, g, or t

<400> SEQUENCE: 28
aagnnnnnnc tc 12

<210> SEQ ID NO 29
<211> LENGTH: 13
<212> TYPE: DNA
<213> ORGANISM: Helicobacter pylori
<220> FEATURE:
<221> NAME/KEY: modified_base
<222> LOCATION: (5)..(11)
<223> OTHER INFORMATION: a, c, t, g, unknown or other
<220> FEATURE:
<221> NAME/KEY: misc_feature
<222> LOCATION: (5)..(11)
<223> OTHER INFORMATION: n is a, c, g, or t

<400> SEQUENCE: 29
crtannnnnn ntc 13

<210> SEQ ID NO 30
<211> LENGTH: 13
<212> TYPE: DNA
<213> ORGANISM: Helicobacter pylori
<220> FEATURE:
<221> NAME/KEY: modified_base
<222> LOCATION: (3)..(9)
<223> OTHER INFORMATION: a, c, t, g, unknown or other
<220> FEATURE:
<221> NAME/KEY: misc_feature
<222> LOCATION: (3)..(9)
<223> OTHER INFORMATION: n is a, c, g, or t

<400> SEQUENCE: 30
gannnnnnnt ayg 13

<210> SEQ ID NO 31
<211> LENGTH: 12
<212> TYPE: DNA
<213> ORGANISM: Helicobacter pylori
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 31
cyannnnnnt tc 12

<210> SEQ ID NO 32
<211> LENGTH: 12
<212> TYPE: DNA
<213> ORGANISM: Helicobacter pylori
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 32
gaannnnnnt rg 12

<210> SEQ ID NO 33
<211> LENGTH: 15
<212> TYPE: DNA
<213> ORGANISM: Escherichia coli
<220> FEATURE:
<221> NAME/KEY: modified_base
<222> LOCATION: (4)..(10)
<223> OTHER INFORMATION: a, c, t, g, unknown or other
<220> FEATURE:
<221> NAME/KEY: misc_feature
<222> LOCATION: (4)..(10)
<223> OTHER INFORMATION: n is a, c, g, or t

<400> SEQUENCE: 33
tacnnnnnnn rtrtc 15

<210> SEQ ID NO 34
<211> LENGTH: 15
<212> TYPE: DNA
<213> ORGANISM: Escherichia coli
<220> FEATURE:
<221> NAME/KEY: modified_base
<222> LOCATION: (6)..(12)
<223> OTHER INFORMATION: a, c, t, g, unknown or other
<220> FEATURE:
<221> NAME/KEY: misc_feature
<222> LOCATION: (6)..(12)
<223> OTHER INFORMATION: n is a, c, g, or t

<400> SEQUENCE: 34
gayaynnnnn nngta 15

<210> SEQ ID NO 35
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 35
catannnnnn htc 13

<210> SEQ ID NO 36
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(11)
<223> OTHER INFORMATION: a, c, t, g, unknown or other
<220> FEATURE:
<221> NAME/KEY: misc_feature
<222> LOCATION: (5)..(11)
<223> OTHER INFORMATION: n is a, c, g, or t

<400> SEQUENCE: 36
catannnnnn ntc 13

<210> SEQ ID NO 37

```
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 37

ggannnnnng ttg                                                        13


<210> SEQ ID NO 38
<211> LENGTH: 12
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 38

cagnnnnnrt gt                                                         12


<210> SEQ ID NO 39
<211> LENGTH: 14
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 39

ytcannnnnn gtty                                                       14


<210> SEQ ID NO 40
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 40

gtannnnncg atc                                                        13
```

```
<210> SEQ ID NO 41
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 41

gatgnnnnnn tac                                                      13


<210> SEQ ID NO 42
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (8)..(10)
<223> OTHER INFORMATION: a, c, t, g, unknown or other
<220> FEATURE:
<221> NAME/KEY: misc_feature
<222> LOCATION: (8)..(10)
<223> OTHER INFORMATION: n is a, c, g, or t

<400> SEQUENCE: 42

atnaaaannn ggt                                                      13


<210> SEQ ID NO 43
<211> LENGTH: 14
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(10)
<223> OTHER INFORMATION: a, c, t, g, unknown or other
<220> FEATURE:
<221> NAME/KEY: misc_feature
<222> LOCATION: (4)..(10)
<223> OTHER INFORMATION: n is a, c, g, or t

<400> SEQUENCE: 43

cagnnnnnnn gttc                                                     14


<210> SEQ ID NO 44
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(9)
<223> OTHER INFORMATION: a, c, t, g, unknown or other
<220> FEATURE:
```

<221> NAME/KEY: misc_feature
<222> LOCATION: (4)..(9)
<223> OTHER INFORMATION: n is a, c, g, or t

<400> SEQUENCE: 44
aagnnnnnnc atc 13

<210> SEQ ID NO 45
<211> LENGTH: 14
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(10)
<223> OTHER INFORMATION: a, c, t, g, unknown or other
<220> FEATURE:
<221> NAME/KEY: misc_feature
<222> LOCATION: (4)..(10)
<223> OTHER INFORMATION: n is a, c, g, or t

<400> SEQUENCE: 45
tacnnnnnnn gttc 14

<210> SEQ ID NO 46
<211> LENGTH: 16
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(12)
<223> OTHER INFORMATION: a, c, t, g, unknown or other
<220> FEATURE:
<221> NAME/KEY: misc_feature
<222> LOCATION: (5)..(12)
<223> OTHER INFORMATION: n is a, c, g, or t

<400> SEQUENCE: 46
craannnnnn nntayc 16

<210> SEQ ID NO 47
<211> LENGTH: 14
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(10)
<223> OTHER INFORMATION: a, c, t, g, unknown or other
<220> FEATURE:
<221> NAME/KEY: misc_feature
<222> LOCATION: (4)..(10)
<223> OTHER INFORMATION: n is a, c, g, or t

<400> SEQUENCE: 47
cacnnnnnnn ctgg 14

<210> SEQ ID NO 48
<211> LENGTH: 15
<212> TYPE: DNA
<213> ORGANISM: Klebsiella pneumoniae
<220> FEATURE:
<221> NAME/KEY: modified_base
<222> LOCATION: (5)..(11)
<223> OTHER INFORMATION: a, c, t, g, unknown or other
<220> FEATURE:
<221> NAME/KEY: misc_feature
<222> LOCATION: (5)..(11)
<223> OTHER INFORMATION: n is a, c, g, or t

<400> SEQUENCE: 48
gaaynnnnnn nctgg 15

<210> SEQ ID NO 49
<211> LENGTH: 13
<212> TYPE: DNA
<213> ORGANISM: Klebsiella pneumoniae
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 49
gcannnnncg atc 13

<210> SEQ ID NO 50
<211> LENGTH: 13
<212> TYPE: DNA
<213> ORGANISM: Klebsiella pneumoniae
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 50
gcannnnnnc atc 13

<210> SEQ ID NO 51
<211> LENGTH: 15
<212> TYPE: DNA
<213> ORGANISM: Klebsiella pneumoniae
<220> FEATURE:
<221> NAME/KEY: modified_base
<222> LOCATION: (4)..(11)
<223> OTHER INFORMATION: a, c, t, g, unknown or other
<220> FEATURE:
<221> NAME/KEY: misc_feature
<222> LOCATION: (4)..(11)
<223> OTHER INFORMATION: n is a, c, g, or t

<400> SEQUENCE: 51
cgannnnnnn ntgcc 15

<210> SEQ ID NO 52
<211> LENGTH: 12
<212> TYPE: DNA
<213> ORGANISM: Klebsiella pneumoniae
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 52
acgnnnnngt tg 12

<210> SEQ ID NO 53
<211> LENGTH: 15
<212> TYPE: DNA
<213> ORGANISM: Klebsiella pneumoniae
<220> FEATURE:
<221> NAME/KEY: modified_base
<222> LOCATION: (5)..(11)
<223> OTHER INFORMATION: a, c, t, g, unknown or other
<220> FEATURE:
<221> NAME/KEY: misc_feature
<222> LOCATION: (5)..(11)
<223> OTHER INFORMATION: n is a, c, g, or t

<400> SEQUENCE: 53
ccagnnnnnn nrttc 15

<210> SEQ ID NO 54
<211> LENGTH: 13
<212> TYPE: DNA
<213> ORGANISM: Klebsiella pneumoniae
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(9)
<223> OTHER INFORMATION: a, c, t, g, unknown or other
<220> FEATURE:
<221> NAME/KEY: misc_feature
<222> LOCATION: (7)..(9)
<223> OTHER INFORMATION: n is a, c, g, or t

<400> SEQUENCE: 54
gyacnannnr ttg 13

<210> SEQ ID NO 55
<211> LENGTH: 13
<212> TYPE: DNA
<213> ORGANISM: Klebsiella pneumoniae
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (7)..(9)
<223> OTHER INFORMATION: a, c, t, g, unknown or other
<220> FEATURE:
<221> NAME/KEY: misc_feature
<222> LOCATION: (7)..(9)
<223> OTHER INFORMATION: n is a, c, g, or t

<400> SEQUENCE: 55
caannannng tvc 13

<210> SEQ ID NO 56
<211> LENGTH: 13
<212> TYPE: DNA
<213> ORGANISM: Klebsiella pneumoniae
<220> FEATURE:
<221> NAME/KEY: modified_base
<222> LOCATION: (4)..(6)
<223> OTHER INFORMATION: a, c, t, g, unknown or other

```
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: misc_feature
<222> LOCATION: (8)..(9)
<223> OTHER INFORMATION: n is a, c, g, or t

<400> SEQUENCE: 56

caannntnng tdc                                                    13


<210> SEQ ID NO 57
<211> LENGTH: 14
<212> TYPE: DNA
<213> ORGANISM: Klebsiella pneumoniae
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 57

gaynnnnnnr tayc                                                   14


<210> SEQ ID NO 58
<211> LENGTH: 12
<212> TYPE: DNA
<213> ORGANISM: Klebsiella pneumoniae
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 58

acgnnnnnnc tg                                                     12


<210> SEQ ID NO 59
<211> LENGTH: 13
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 59

aacnnnnnng tgc                                                    13


<210> SEQ ID NO 60
<211> LENGTH: 13
<212> TYPE: DNA
<213> ORGANISM: Unknown
<220> FEATURE:
```

<223> OTHER INFORMATION: Description of Unknown: Bacterial contig motif
<220> FEATURE:
<221> NAME/KEY: modified_base
<222> LOCATION: (5)..(10)
<223> OTHER INFORMATION: a, c, t, g, unknown or other
<220> FEATURE:
<221> NAME/KEY: misc_feature
<222> LOCATION: (5)..(10)
<223> OTHER INFORMATION: n is a, c, g, or t

<400> SEQUENCE: 60
gcacnnnnnn gtt 13

<210> SEQ ID NO 61
<211> LENGTH: 12
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (5)..(9)
<223> OTHER INFORMATION: a, c, t, g, unknown or other
<220> FEATURE:
<221> NAME/KEY: misc_feature
<222> LOCATION: (5)..(9)
<223> OTHER INFORMATION: n is a, c, g, or t

<400> SEQUENCE: 61
tcacnnnnna tg 12

<210> SEQ ID NO 62
<211> LENGTH: 11
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: misc_feature
<222> LOCATION: (4)..(8)
<223> OTHER INFORMATION: n is a, c, g, or t

<400> SEQUENCE: 62
cagnnnnngg a 11

<210> SEQ ID NO 63
<211> LENGTH: 12
<212> TYPE: DNA
<213> ORGANISM: Unknown
<220> FEATURE:
<223> OTHER INFORMATION: Description of Unknown: Bacterial contig motif
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 63
atgnnnnnnt gg 12

<210> SEQ ID NO 64
<211> LENGTH: 12
<212> TYPE: DNA
<213> ORGANISM: Unknown

-continued

```
<220> FEATURE:
<223> OTHER INFORMATION: Description of Unknown: Bacterial contig motif
<220> FEATURE:
<221> NAME/KEY: modified_base
<222> LOCATION: (4)..(9)
<223> OTHER INFORMATION: a, c, t, g, unknown or other
<220> FEATURE:
<221> NAME/KEY: misc_feature
<222> LOCATION: (4)..(9)
<223> OTHER INFORMATION: n is a, c, g, or t

<400> SEQUENCE: 64

ccannnnnnc at                                                          12
```